United States Patent
Krieg et al.

(10) Patent No.: US 10,174,315 B2
(45) Date of Patent: Jan. 8, 2019

(54) COMPOSITIONS AND METHODS FOR MODULATING HEMOGLOBIN GENE FAMILY EXPRESSION

(71) Applicants: Translate Bio MA, Inc., Lexington, MA (US); The General Hospital Corporation, Boston, MA (US)

(72) Inventors: Arthur M. Krieg, Cambridge, MA (US); Romesh Subramanian, Framingham, MA (US); James McSwiggen, Arlington, MA (US); Jeannie T. Lee, Boston, MA (US)

(73) Assignees: The General Hospital Corporation, Boston, MA (US); Translate Bio MA, Inc., Lexington, MA (US)

( * ) Notice: Subject to any disclaimer, the term of this patent is extended or adjusted under 35 U.S.C. 154(b) by 31 days.

(21) Appl. No.: 14/401,201

(22) PCT Filed: May 16, 2013

(86) PCT No.: PCT/US2013/041382
§ 371 (c)(1),
(2) Date: Nov. 14, 2014

(87) PCT Pub. No.: WO2013/173599
PCT Pub. Date: Nov. 21, 2013

(65) Prior Publication Data
US 2015/0133528 A1     May 14, 2015

Related U.S. Application Data

(60) Provisional application No. 61/785,956, filed on Mar. 14, 2013, provisional application No. 61/647,901, filed on May 16, 2012.

(51) Int. Cl.
| | |
|---|---|
| C12N 15/113 | (2010.01) |
| A61K 31/7125 | (2006.01) |
| A61K 31/712 | (2006.01) |
| A61K 31/7115 | (2006.01) |
| C07H 21/00 | (2006.01) |
| C07H 21/02 | (2006.01) |
| C07H 21/04 | (2006.01) |
| A61K 31/7088 | (2006.01) |
| A61K 47/28 | (2006.01) |
| A61K 47/64 | (2017.01) |

(52) U.S. Cl.
CPC ........ *C12N 15/113* (2013.01); *A61K 31/7088* (2013.01); *A61K 31/712* (2013.01); *A61K 31/7125* (2013.01); *A61K 47/28* (2013.01); *A61K 47/64* (2017.08); *C07H 21/00* (2013.01); *C07H 21/02* (2013.01); *C07H 21/04* (2013.01); *C12N 2310/11* (2013.01); *C12N 2310/315* (2013.01); *C12N 2310/3231* (2013.01); *C12N 2310/3341* (2013.01); *C12N 2310/341* (2013.01)

(58) Field of Classification Search
None
See application file for complete search history.

(56) References Cited

U.S. PATENT DOCUMENTS

| | | |
|---|---|---|
| 4,725,677 A | 2/1988 | Köster et al. |
| 5,491,133 A | 2/1996 | Walder et al. |
| 5,576,208 A | 11/1996 | Monia et al. |
| 5,623,065 A | 4/1997 | Cook et al. |
| 5,652,355 A | 7/1997 | Metelev et al. |
| 5,661,134 A | 8/1997 | Cook et al. |
| 5,912,332 A | 6/1999 | Agrawal et al. |
| 5,914,396 A | 6/1999 | Cook et al. |
| 5,919,619 A | 7/1999 | Tullis |
| 5,965,722 A | 10/1999 | Ecker et al. |
| 6,015,710 A | 1/2000 | Shay et al. |
| 6,046,307 A | 4/2000 | Shay et al. |
| 6,063,400 A | 5/2000 | Geho et al. |
| 6,107,094 A | 8/2000 | Crooke |
| 6,143,881 A | 11/2000 | Metelev et al. |
| 6,146,829 A | 11/2000 | Cook et al. |
| 6,197,944 B1 | 3/2001 | Walder et al. |
| 6,210,892 B1 | 4/2001 | Bennett et al. |
| 6,294,650 B1 | 9/2001 | Shay et al. |
| 6,326,199 B1 | 12/2001 | Cook et al. |
| 6,346,614 B1 | 2/2002 | Metelev et al. |
| 6,359,124 B1 | 3/2002 | Ecker et al. |
| 6,395,492 B1 | 5/2002 | Manoharan et al. |
| 6,451,991 B1 | 9/2002 | Martin et al. |
| 6,503,754 B1 | 1/2003 | Zhang et al. |
| 6,531,584 B1 | 3/2003 | Cook et al. |
| 6,608,035 B1 | 8/2003 | Agrawal et al. |
| 6,677,445 B1 | 1/2004 | Innis et al. |
| 6,727,355 B2 | 4/2004 | Matsuo et al. |
| 6,753,423 B1 | 6/2004 | Cook et al. |
| 6,831,166 B2 | 12/2004 | Manoharan et al. |

(Continued)

FOREIGN PATENT DOCUMENTS

| | | |
|---|---|---|
| CA | 2805791 A1 | 1/2012 |
| EP | 1 044 987 A2 | 10/2000 |

(Continued)

OTHER PUBLICATIONS

Taylor et al. Drug Discovery Today 1999, vol. 4, pp. 562-567.*

(Continued)

*Primary Examiner* — Tracy Vivlemore
(74) *Attorney, Agent, or Firm* — Wolf, Greenfield & Sacks, P.C.

(57) ABSTRACT

Aspects of the invention provide single stranded oligonucleotides for activating or enhancing expression of hemoglobin genes (HBB, HBD, HBE1, HBG1 or HBG2). Further aspects provide compositions and kits comprising single stranded oligonucleotides for activating or enhancing expression of hemoglobin genes. Methods for modulating expression of hemoglobin genes using the single stranded oligonucleotides are also provided. Further aspects of the invention provide methods for selecting a candidate oligonucleotide for activating or enhancing expression of hemoglobin genes.

31 Claims, No Drawings
Specification includes a Sequence Listing.

(56) References Cited

U.S. PATENT DOCUMENTS

| | | |
|---|---|---|
| 6,919,439 B2 | 7/2005 | Manoharan et al. |
| 7,015,315 B1 | 3/2006 | Cook et al. |
| 7,041,816 B2 | 5/2006 | Ravikumar et al. |
| 7,045,609 B2 | 5/2006 | Metelev et al. |
| 7,226,785 B2* | 6/2007 | Kmiec .................. C12N 15/102 435/440 |
| 7,374,927 B2 | 5/2008 | Palma et al. |
| 7,449,297 B2 | 11/2008 | Freije et al. |
| 7,655,785 B1 | 2/2010 | Bentwich |
| 7,683,036 B2 | 3/2010 | Esau et al. |
| 7,687,616 B1 | 3/2010 | Bentwich et al. |
| 7,687,617 B2 | 3/2010 | Thrue et al. |
| 7,709,456 B2 | 5/2010 | Corey et al. |
| 7,858,592 B2 | 12/2010 | Shames et al. |
| 7,879,992 B2 | 2/2011 | Vickers et al. |
| 7,888,012 B2 | 2/2011 | Iversen et al. |
| 8,092,992 B2 | 1/2012 | Kuwabara et al. |
| 8,129,515 B2 | 3/2012 | Esau et al. |
| 8,153,602 B1 | 4/2012 | Bennett et al. |
| 8,153,606 B2 | 4/2012 | Collard et al. |
| 8,222,221 B2 | 7/2012 | Corey et al. |
| 8,288,354 B2 | 10/2012 | Wahlestedt |
| 8,288,356 B2 | 10/2012 | Obad et al. |
| 8,318,690 B2 | 11/2012 | Collard et al. |
| 8,361,980 B2 | 1/2013 | Kauppinen et al. |
| 8,404,659 B2 | 3/2013 | Kauppinen et al. |
| 8,415,313 B2 | 4/2013 | Mourich et al. |
| 8,846,639 B2 | 9/2014 | Swayze et al. |
| 9,328,346 B2 | 5/2016 | Lee et al. |
| 9,567,581 B2 | 2/2017 | Lee et al. |
| 9,580,708 B2 | 2/2017 | Uhlmann et al. |
| 9,593,330 B2 | 3/2017 | Collard et al. |
| 2002/0160379 A1 | 10/2002 | Cook et al. |
| 2003/0198983 A1 | 10/2003 | Zhou |
| 2003/0208061 A1* | 11/2003 | Manoharan ............ C07H 21/00 536/25.3 |
| 2003/0219770 A1 | 11/2003 | Eshleman et al. |
| 2003/0228690 A1 | 12/2003 | Baker et al. |
| 2003/0235822 A1* | 12/2003 | Lokhov .................. C07H 19/06 435/6.18 |
| 2004/0002153 A1 | 1/2004 | Monia et al. |
| 2004/0038274 A1 | 2/2004 | Cook et al. |
| 2004/0096848 A1 | 5/2004 | Thrue et al. |
| 2004/0241651 A1 | 12/2004 | Olek et al. |
| 2004/0248840 A1 | 12/2004 | Hansen et al. |
| 2005/0003369 A1 | 1/2005 | Christians et al. |
| 2005/0026160 A1* | 2/2005 | Allerson ................ C07H 21/00 435/6.11 |
| 2005/0054836 A1 | 3/2005 | Krainer et al. |
| 2005/0108783 A1 | 5/2005 | Koike |
| 2005/0130924 A1 | 6/2005 | Monia et al. |
| 2005/0164209 A1 | 7/2005 | Bennett et al. |
| 2005/0176025 A1 | 8/2005 | McSwiggen et al. |
| 2005/0203042 A1 | 9/2005 | Frieden et al. |
| 2005/0233455 A1 | 10/2005 | Damha et al. |
| 2005/0244851 A1 | 11/2005 | Blume et al. |
| 2005/0246794 A1 | 11/2005 | Khvorova et al. |
| 2005/0261218 A1 | 11/2005 | Esau et al. |
| 2005/0272080 A1 | 12/2005 | Palma et al. |
| 2006/0003322 A1 | 1/2006 | Bentwich |
| 2006/0046260 A1 | 3/2006 | Kriksunov et al. |
| 2006/0128646 A1 | 6/2006 | Christensen et al. |
| 2006/0270624 A1 | 11/2006 | Cook et al. |
| 2007/0032446 A1 | 2/2007 | Cook et al. |
| 2007/0042380 A1 | 2/2007 | Bentwich et al. |
| 2007/0111963 A1 | 5/2007 | Corey et al. |
| 2007/0123484 A1 | 5/2007 | Bhat et al. |
| 2007/0191294 A1 | 8/2007 | Elmen et al. |
| 2007/0219244 A1 | 9/2007 | Jenssen et al. |
| 2007/0269815 A1 | 11/2007 | Rivory et al. |
| 2008/0015162 A1 | 1/2008 | Bhanot et al. |
| 2008/0176793 A1 | 7/2008 | Simons et al. |
| 2008/0194463 A1 | 8/2008 | Weller et al. |
| 2008/0249039 A1 | 10/2008 | Elmen et al. |
| 2008/0293655 A1 | 11/2008 | Aygun et al. |
| 2008/0318895 A1 | 12/2008 | Lee et al. |
| 2009/0082297 A1 | 3/2009 | Lioy et al. |
| 2009/0092988 A1 | 4/2009 | Schwartz et al. |
| 2009/0099066 A1 | 4/2009 | Moulton et al. |
| 2009/0099109 A1 | 4/2009 | Shames et al. |
| 2009/0143326 A1 | 6/2009 | Obad et al. |
| 2009/0155910 A1 | 6/2009 | McGonigle |
| 2009/0221685 A1 | 9/2009 | Esau et al. |
| 2009/0258925 A1 | 10/2009 | Wahlestedt |
| 2009/0325868 A1 | 12/2009 | Liu et al. |
| 2009/0326051 A1 | 12/2009 | Corey et al. |
| 2010/0004314 A1* | 1/2010 | Dondero ............ A61K 48/0008 514/44 A |
| 2010/0105760 A1 | 4/2010 | Collard et al. |
| 2010/0111982 A1 | 5/2010 | Zang et al. |
| 2010/0112042 A1 | 5/2010 | Polisky et al. |
| 2010/0124547 A1 | 5/2010 | Bramlage et al. |
| 2010/0143359 A1 | 6/2010 | Ebert et al. |
| 2010/0197762 A1 | 8/2010 | Swayze et al. |
| 2010/0210707 A1 | 8/2010 | Li et al. |
| 2010/0210712 A1 | 8/2010 | Hansen et al. |
| 2010/0247543 A1 | 9/2010 | Maes et al. |
| 2010/0280100 A1 | 11/2010 | Collard et al. |
| 2010/0286141 A1 | 11/2010 | Durden et al. |
| 2010/0286234 A1 | 11/2010 | Elmen et al. |
| 2010/0317606 A1 | 12/2010 | Chan et al. |
| 2011/0039910 A1 | 2/2011 | Crooke et al. |
| 2011/0077286 A1 | 3/2011 | Damha et al. |
| 2011/0086833 A1 | 4/2011 | Paushkin et al. |
| 2011/0110860 A1 | 5/2011 | Corey et al. |
| 2011/0150868 A1 | 6/2011 | Yu et al. |
| 2011/0172292 A1 | 7/2011 | Hansen et al. |
| 2011/0191912 A1 | 8/2011 | Alexandrov |
| 2011/0207217 A1 | 8/2011 | Corey et al. |
| 2011/0237606 A1 | 9/2011 | Chai et al. |
| 2011/0237649 A1 | 9/2011 | Collard et al. |
| 2011/0237650 A1 | 9/2011 | Collard et al. |
| 2011/0237651 A1 | 9/2011 | Collard et al. |
| 2011/0251261 A1 | 10/2011 | Burnett et al. |
| 2011/0263687 A1 | 10/2011 | Mattick et al. |
| 2011/0294870 A1 | 12/2011 | Collard et al. |
| 2011/0319283 A1 | 12/2011 | Thompson |
| 2011/0319317 A1 | 12/2011 | Collard et al. |
| 2011/0319475 A1 | 12/2011 | Collard et al. |
| 2011/0319476 A1 | 12/2011 | Collard et al. |
| 2012/0004184 A1 | 1/2012 | Collard et al. |
| 2012/0004278 A1 | 1/2012 | Chang et al. |
| 2012/0010156 A1 | 1/2012 | Collard et al. |
| 2012/0046236 A1 | 2/2012 | Collard et al. |
| 2012/0046344 A1 | 2/2012 | Collard et al. |
| 2012/0046345 A1 | 2/2012 | Collard et al. |
| 2012/0064048 A1 | 3/2012 | Collard et al. |
| 2012/0071418 A1 | 3/2012 | Copeland et al. |
| 2012/0083596 A1 | 4/2012 | Elmen et al. |
| 2012/0088817 A1 | 4/2012 | Collard et al. |
| 2012/0094934 A1 | 4/2012 | Collard et al. |
| 2012/0095079 A1 | 4/2012 | Collard et al. |
| 2012/0095081 A1 | 4/2012 | Collard et al. |
| 2012/0129917 A1 | 5/2012 | Collard et al. |
| 2012/0135941 A1 | 5/2012 | Collard et al. |
| 2012/0142610 A1 | 6/2012 | Collard et al. |
| 2012/0142758 A1 | 6/2012 | Collard et al. |
| 2012/0149759 A1 | 6/2012 | Collard et al. |
| 2012/0157333 A1 | 6/2012 | Kauppinen et al. |
| 2012/0171170 A1 | 7/2012 | Collard et al. |
| 2012/0252869 A1 | 10/2012 | Collard et al. |
| 2012/0264812 A1 | 10/2012 | Collard et al. |
| 2012/0277290 A1 | 11/2012 | Collard et al. |
| 2012/0288869 A1 | 11/2012 | Schwartz et al. |
| 2012/0289581 A1 | 11/2012 | Chang et al. |
| 2012/0289583 A1 | 11/2012 | Collard et al. |
| 2012/0295952 A1 | 11/2012 | Collard et al. |
| 2012/0295953 A1 | 11/2012 | Colalrd et al. |
| 2012/0295954 A1 | 11/2012 | Collard et al. |
| 2012/0295959 A1 | 11/2012 | Collard et al. |
| 2012/0309814 A1 | 12/2012 | Collard et al. |
| 2012/0322851 A1 | 12/2012 | Hardee et al. |
| 2012/0322853 A1 | 12/2012 | Collard et al. |
| 2012/0329727 A1 | 12/2012 | Collard et al. |

(56) References Cited

U.S. PATENT DOCUMENTS

| | | |
|---|---|---|
| 2012/0329855 A1 | 12/2012 | Collar et al. |
| 2013/0035372 A1 | 2/2013 | Collard et al. |
| 2013/0035373 A1 | 2/2013 | Collard et al. |
| 2013/0053428 A1 | 2/2013 | Wahlestedt |
| 2013/0065947 A1 | 3/2013 | Collard et al. |
| 2013/0072421 A1 | 3/2013 | Collard et al. |
| 2013/0072546 A1 | 3/2013 | Collard et al. |
| 2013/0079505 A1 | 3/2013 | Moeller et al. |
| 2013/0085112 A1 | 4/2013 | Collard et al. |
| 2013/0096183 A1 | 4/2013 | Collard et al. |
| 2013/0143946 A1 | 6/2013 | Collard et al. |
| 2013/0164846 A1 | 6/2013 | Saestrom |
| 2013/0184325 A9 | 7/2013 | Collard et al. |
| 2013/0245099 A1 | 9/2013 | Collard et al. |
| 2013/0261065 A1 | 10/2013 | Collard et al. |
| 2013/0289092 A1 | 10/2013 | Rigo et al. |
| 2014/0142160 A1 | 5/2014 | Lee et al. |
| 2014/0187606 A1 | 7/2014 | Collard et al. |
| 2015/0099791 A1 | 4/2015 | Krieg et al. |
| 2015/0133362 A1 | 5/2015 | Krieg et al. |
| 2015/0133529 A1 | 5/2015 | Krieg et al. |
| 2015/0141320 A1 | 5/2015 | Krieg et al. |
| 2015/0152410 A1 | 6/2015 | Krieg et al. |
| 2015/0159160 A1 | 6/2015 | Krieg et al. |
| 2015/0159161 A1 | 6/2015 | Krieg et al. |
| 2015/0191722 A1 | 7/2015 | Krieg et al. |
| 2015/0218560 A1 | 8/2015 | Krieg et al. |
| 2015/0225717 A1 | 8/2015 | Lee et al. |
| 2017/0037396 A1 | 2/2017 | Lee et al. |

FOREIGN PATENT DOCUMENTS

| | | | | |
|---|---|---|---|---|
| EP | 1 752 536 A1 | 5/2005 | | |
| EP | 1 695 979 A2 | 8/2006 | | |
| EP | 1 957 648 B1 | 11/2006 | | |
| EP | 1752536 A1 | 2/2007 | | |
| EP | 1 967 525 A2 | 9/2008 | | |
| EP | 2 021 472 B1 | 6/2011 | | |
| EP | 2 023 940 B1 | 6/2011 | | |
| EP | 2 431 467 A2 | 3/2012 | | |
| EP | 2 431 467 A3 | 5/2012 | | |
| EP | 2 591 797 A1 | 5/2013 | | |
| JP | 04-320700 | 11/1992 | | |
| JP | 2006-522597 | 10/2006 | | |
| JP | 2008-044958 A | 2/2008 | | |
| JP | 2009-536037 | 10/2009 | | |
| JP | 2010-507579 A | 3/2010 | | |
| JP | 2010-516256 | 5/2010 | | |
| JP | 2015-518714 | 7/2015 | | |
| KR | 10-2011-0050134 A | 5/2011 | | |
| WO | WO 89/05358 A1 | 6/1989 | | |
| WO | WO 93/13121 A1 | 7/1993 | | |
| WO | WO 94/02499 A1 | 2/1994 | | |
| WO | WO 94/17093 A1 | 8/1994 | | |
| WO | WO 2001/007662 A1 | 2/2001 | | |
| WO | WO 01/36627 A2 | 5/2001 | | |
| WO | WO 02/103015 A2 | 12/2002 | | |
| WO | WO 2004011613 A2 * | 2/2004 | ........... | C12N 15/113 |
| WO | WO 2004/099382 A2 | 11/2004 | | |
| WO | WO 2004/113867 A2 | 12/2004 | | |
| WO | WO 2005/042018 A2 | 5/2005 | | |
| WO | WO 2005/044981 A2 | 5/2005 | | |
| WO | WO 2005/061710 A1 | 7/2005 | | |
| WO | WO 2005/089169 A2 | 9/2005 | | |
| WO | WO 2005/094370 A2 | 10/2005 | | |
| WO | WO 2006/063356 A1 | 6/2006 | | |
| WO | WO 2006/130201 A1 | 12/2006 | | |
| WO | WO 2007/031091 A2 | 3/2007 | | |
| WO | WO 2007/086990 A2 | 8/2007 | | |
| WO | WO 2007/086990 A3 | 8/2007 | | |
| WO | WO 2007/115578 A1 | 10/2007 | | |
| WO | WO 2007/133812 A2 | 11/2007 | | |
| WO | WO 2008/024499 A2 | 2/2008 | | |
| WO | WO 2008/025069 A1 | 3/2008 | | |
| WO | WO 2008/029619 A1 | 3/2008 | | |
| WO | WO 2008/061537 A2 | 5/2008 | | |
| WO | WO 2008/083931 A1 | 7/2008 | | |
| WO | WO 2008/103761 A2 | 8/2008 | | |
| WO | WO 2008/103763 A2 | 8/2008 | | |
| WO | WO 2008/113832 A2 | 9/2008 | | |
| WO | WO 2008/141282 A2 | 11/2008 | | |
| WO | WO 2009/043353 A2 | 4/2009 | | |
| WO | WO 2009/046397 A2 | 4/2009 | | |
| WO | WO 2009/061851 A2 | 5/2009 | | |
| WO | WO 2009/090182 A1 | 7/2009 | | |
| WO | WO 2009/124341 A1 | 10/2009 | | |
| WO | WO 2009/134710 A2 | 11/2009 | | |
| WO | WO 2009/149182 A1 | 12/2009 | | |
| WO | WO 2010/000665 A1 | 1/2010 | | |
| WO | WO 2010/014592 A1 | 2/2010 | | |
| WO | WO 2010/065671 A2 | 6/2010 | | |
| WO | WO 2010/065787 A2 | 6/2010 | | |
| WO | WO 2010/083615 A1 | 7/2010 | | |
| WO | WO 2010/093860 A2 | 8/2010 | | |
| WO | WO 2010/093904 A2 | 8/2010 | | |
| WO | WO 2010/102058 A2 | 9/2010 | | |
| WO | WO 2010/107733 A2 | 9/2010 | | |
| WO | WO 2010/129746 A2 | 11/2010 | | |
| WO | WO 2010/129861 A2 | 11/2010 | | |
| WO | WO 2010/135329 A2 | 11/2010 | | |
| WO | WO 2010/135695 A2 | 11/2010 | | |
| WO | WO 2010129799 A2 * | 11/2010 | ........... | A61K 31/713 |
| WO | WO 2010/138806 A2 | 12/2010 | | |
| WO | WO 2010/148050 A2 | 12/2010 | | |
| WO | WO 2010/148065 A2 | 12/2010 | | |
| WO | WO 2010/151671 A2 | 12/2010 | | |
| WO | WO 2010/151674 A2 | 12/2010 | | |
| WO | WO 2011/009624 A1 | 1/2011 | | |
| WO | WO 2011/010706 A1 | 1/2011 | | |
| WO | WO 2011/017516 A2 | 2/2011 | | |
| WO | WO 2011/019815 A2 | 2/2011 | | |
| WO | WO 2011/022606 A2 | 2/2011 | | |
| WO | WO 2011/025862 A2 | 3/2011 | | |
| WO | WO 2011/031482 A2 | 3/2011 | | |
| WO | WO 2011/032109 A1 | 3/2011 | | |
| WO | WO 2011/038205 A2 | 3/2011 | | |
| WO | WO 2011/038210 A2 | 3/2011 | | |
| WO | WO 2011/048125 A1 | 4/2011 | | |
| WO | WO 2011/079261 A2 | 6/2011 | | |
| WO | WO 2011/079263 A2 | 6/2011 | | |
| WO | WO 2011/082409 A2 | 7/2011 | | |
| WO | WO 2011/084455 A2 | 7/2011 | | |
| WO | WO 2011/085066 A2 | 7/2011 | | |
| WO | WO 2011/097388 A1 | 8/2011 | | |
| WO | WO 2011/097582 A2 | 8/2011 | | |
| WO | WO 2011/097641 A1 | 8/2011 | | |
| WO | WO 2011/123745 A2 | 10/2011 | | |
| WO | WO 2011/139387 A1 | 11/2011 | | |
| WO | WO 2011/146674 A2 | 11/2011 | | |
| WO | WO 2011/146675 A2 | 11/2011 | | |
| WO | WO 2011/150005 A2 | 12/2011 | | |
| WO | WO 2011/159836 A2 | 12/2011 | | |
| WO | WO 2011/161460 A2 | 12/2011 | | |
| WO | WO 2011/163499 A2 | 12/2011 | | |
| WO | WO 2012/009347 A2 | 1/2012 | | |
| WO | WO 2012/009402 A2 | 1/2012 | | |
| WO | WO 2012/018881 A2 | 2/2012 | | |
| WO | WO 2012/024478 A2 | 2/2012 | | |
| WO | WO 2012/047956 A2 | 4/2012 | | |
| WO | WO 2012/054723 A2 | 4/2012 | | |
| WO | WO 2012/058268 A2 | 5/2012 | | |
| WO | WO 2012/065143 A2 | 5/2012 | | |
| WO | WO 2012/068340 A2 | 5/2012 | | |
| WO | WO 2012/071238 A2 | 5/2012 | | |
| WO | WO 2012/087983 A1 | 6/2012 | | |
| WO | WO 2012/109476 A2 | 8/2012 | | |
| WO | WO 2012/138487 A2 | 10/2012 | | |
| WO | WO 2012/144220 A1 | 10/2012 | | |
| WO | WO 2012/170771 A1 | 12/2012 | | |
| WO | WO 2013/006619 A1 | 1/2013 | | |
| WO | WO 2013/036403 A1 | 3/2013 | | |
| WO | WO 2013/040429 A1 | 3/2013 | | |
| WO | WO 2013/124807 A2 | 8/2013 | | |
| WO | WO 2013/138374 A2 | 9/2013 | | |

(56) References Cited

FOREIGN PATENT DOCUMENTS

| WO | WO 2013/173598 A1 | 11/2013 |
|---|---|---|
| WO | WO 2013/173599 A1 | 11/2013 |
| WO | WO 2013/173601 A1 | 11/2013 |
| WO | WO 2013/173605 A1 | 11/2013 |
| WO | WO 2013/173608 A1 | 11/2013 |
| WO | WO 2013/173635 A1 | 11/2013 |
| WO | WO 2013/173637 A1 | 11/2013 |
| WO | WO 2013/173638 A1 | 11/2013 |
| WO | WO 2013/173645 A1 | 11/2013 |
| WO | WO 2013/173647 A1 | 11/2013 |
| WO | WO 2013/173652 A1 | 11/2013 |
| WO | WO 2014/043544 A1 | 3/2014 |
| WO | WO 2014/076195 A1 | 5/2014 |
| WO | WO 2014/197826 A1 | 12/2014 |
| WO | WO 2015/035476 A1 | 3/2015 |

OTHER PUBLICATIONS

GenBank accession No. AM750048 [online] submitted Jul. 12, 2007 [retrieved on Apr. 25, 2017] Retrieved from the internet: https://www.ncbi.nlm.nih.gov/nuccore/AM750048.*
International Preliminary Report on Patentability for Application No. PCT/US2013/041440 dated Nov. 27, 2014.
International Preliminary Report on Patentability for Application No. PCT/US2013/041452 dated Nov. 27, 2014.
International Search Report and Written Opinion for Application No. PCT/US2013/041382 dated Sep. 5, 2013.
International Preliminary Report on Patentability for Application No. PCT/US2013/041382 dated Nov. 27, 2014.
International Preliminary Report on Patentability for Application No. PCT/US2013/041381 dated Nov. 27, 2014.
International Preliminary Report on Patentability for Application No. PCT/US2013/041455 dated Nov. 27, 2014.
International Preliminary Report on Patentability for Application No. PCT/US2013/041389 dated Nov. 27, 2014.
International Preliminary Report on Patentability for Application No. PCT/US2013/041385 dated Nov. 27, 2014.
International Preliminary Report on Patentability for Application No. PCT/US2013/041394 dated Nov. 27, 2014.
International Preliminary Report on Patentability for Application No. PCT/US2013/041434 dated Nov. 27, 2014.
International Preliminary Report on Patentability for Application No. PCT/US2013/041437 dated Nov. 27, 2014.
International Search Report and Written Opinion for Application No. PCT/US2013/041461 dated Aug. 21, 2013.
International Preliminary Report on Patentability for Application No. PCT/US2013/041461 dated Nov. 27, 2014.
International Search Report and Written Opinion for Application No. PCT/US2014/041345 dated Oct. 14, 2014.
Extended European Search Report for Application No. EP 11840099.3 dated Oct. 7, 2014.
International Search Report and Written Opinion for Application No. PCT/US2011/060493 dated Apr. 18, 2012.
European Search Report for Application No. EP 11852141.8 dated Jan. 19, 2015.
International Search Report and Written Opinion for Application No. PCT/US2011/065939 dated Apr. 20, 2012.
Genbank Submission; NIH/NCBI, Accession No. AA106140. Marra et al., Feb. 4, 1997. 1 page.
Genbank Submission; NIH/NCBI, Accession No. AL137002. Holt, Dec. 13, 2012. 29 pages.
Genbank Submission; NIH/NCBI, Accession No. BX383579. Li et al., Dec. 23, 2010. 1 page.
Genbank Submission; NIH/NCBI, Accession No. NM_001079668. Young et al., Jan. 18, 2014. 4 pages.
Genbank Submission; NIH/NCBI, Accession No. NM_003317. Young et al., Jan. 18, 2014. 4 pages.
Genbank Submission; NIH/NCBI, Accession No. NM_028475. Diez-Roux et al., Feb. 3, 2014. 6 pages.

[No Author Listed], Geneimprint. 2012. http://www.geneimprint.com/site/about-this-site [last accessed May 22, 2015]. 1 page.
[No Author Listed], Imprinted gene. Mosby's Dictionary of Medicine, Nursing and Health Professions. 8th ed. 2009;949.
Ahn et al., Retinoic acid accelerates downregulation of the Xist repressor, Oct. 4, and increases the likelihood of Xist activation when Tsix is deficient. BMC Develop Biol. 2010;10:90. 14 pages.
Astuti et al., Epigenetic alteration at the DLK1-GTL2 imprinted domain in human neoplasia: analysis of neuroblastoma, phaeochromocytoma and Wilms' tumour. Br J Cancer. Apr. 25, 2005;92(8):1574-80.
Beletskii et al., PNA interference mapping demonstrates functional domains in the noncoding RNA Xist. Proc Natl Acad Sci U S A. Jul. 31, 2001;98(16):9215-20.
Bernardi et al., Structure, dynamics and functions of promyelocytic leukaemia nuclear bodies. Nat Rev Mol Cell Biol. Dec. 2007;8(12):1006-16. Review.
Bernstein et al., Mouse polycomb proteins bind differentially to methylated histone H3 and RNA and are enriched in facultative heterochromatin. Mol Cell Biol. Apr. 2006;26(7):2560-9.
Bernstein et al., RNA meets chromatin. Genes Dev. Jul. 15, 2005;19(14):1635-55. Review.
Boyer et al., Polycomb complexes repress developmental regulators in murine embryonic stem cells. Nature. May 18, 2006;441(7091):349-53. Epub Apr. 19, 2006.
Brockdorff et al., The product of the mouse Xist gene is a 15 kb inactive X-specific transcript containing no conserved ORF and located in the nucleus. Cell. Oct. 30, 1992;71(3):515-26.
Brown et al., A gene from the region of the human X inactivation centre is expressed exclusively from the inactive X chromosome. Nature. Jan. 3, 1991;349:38-44.
Brown et al., The Human XIST Gene: Analysis of a 17 kb Inactive X-Specific RNA That Contains Conserved Repeats and Is Highly Localized within the Nucleus. Cell. Oct. 30, 1992;71:527-42.
Carninci et al., the transcriptional landscape of the mammalian genome. Science. Sep. 2, 2005;309(5740):1559-63.
Chahrour et al., MeCP2, a key contributor to neurological disease, activates and represses transcription. Science. May 30, 2008;320(5880):1224-9.
Chen et al., Decoding the function of nuclear long non-coding RNAs. Curr Opin Cell Biol. Jun. 2010;22(3):357-64. doi: 10.1016/j.ceb.2010.03.003. Epub Mar. 29, 2010. Review.
Chow et al., Inducible XIST-dependent X-chromosome inactivation in human somatic cells is reversible. Proc Natl Acad Sci U S A. Jun. 12, 2007;104(24):10104-9. Epub May 30, 2007.
Clark et al., The Reality of Pervasive Transcription. PLOS Bio. Jul. 2011;9(7):e1000625. 6 pages.
Clemson et al., XIST RNA paints the inactive X chromosome at interphase: evidence for a novel RNA involved in nuclear/chromosome structure. J Cell Biol. Feb. 1996;132(3):259-75.
Cohen et al., X-chromosome inactivation and the search for chromosome-wide silencers. Curr Opin Genet Dev. 2002;12:219-24.
Coombes et al., Epigenetic properties and identification of an imprint mark in the Nesp-Gnasxl domain of the mouse Gnas imprinted locus. Mol Cell Biol. Aug. 2003;23(16):5475-88.
Core et al., Nascent RNA sequencing reveals widespread pausing and divergent initiation at human promoters. Science. Dec. 19, 2008;322(5909):1845-8. doi: 10.1126/science.1162228. Epub Dec. 4, 2008.
Costa, Non-coding RNAs: new players in eukaryotic biology. Gene. Sep. 12, 2005;357(2):83-94. Review.
Daughters et al., RNA gain-of-function in spinocerebellar ataxia type 8. PLoS Genet. Aug. 2009;5(8):e1000600. doi: 10.1371/journal.pgen.1000600. Epub Aug. 14, 2009.
Davidson et al., Singles engage the RNA interference pathway. Cell. Aug. 31, 2012;150(5):873-5. doi: 10.1016/j.cell.2012.08.008.
Denisenko et al., Point mutations in the WD40 domain of Eed block its interaction with Ezh2. Mol Cell Biol. Oct. 1998;18(10):5634-42.
Di Certo et al., The artificial gene Jazz, a transcriptional regulator of utrophin, corrects the dystrophic pathology in mdx mice. Hum Mol Genet. Mar. 1, 2010;19(5):752-60. doi: 10.1093/hmg/ddp539. Epub Dec. 4, 2009.

(56) References Cited

OTHER PUBLICATIONS

Dinger et al., NRED: a database of long noncoding RNA expression. Nucleic Acids Res. Jan. 2009;37(Database issue):D122-6. doi: 10.1093/nar/gkn617. Epub Oct. 1, 2008.
Dominski et al., Identification and characterization by antisense oligonucleotides of exon and intron sequences required for splicing. Mol Cell Biol. Nov. 1994; 14(11): 7445-7454.
Dominski et al., Restoration of correct splicing in thalassemic pre-mRNA by antisense oligonucleotides. Proc Natl Acad Sci U S A. Sep. 15, 1993;90(18):8673-7.
Duthie et al., Xist RNA exhibits a banded localization on the inactive X chromosome and is excluded from autosomal material in cis. Hum Mol Genet. Feb. 1999;8(2):195-204.
Edwards et al., Mechanisms regulating imprinted genes in clusters. Curr Opin Cell Biol. Jun. 2007;19(3):281-9. Review.
Engström et al., Complex Loci in human and mouse genomes. PLoS Genet. Apr. 2006;2(4):e47. Epub Apr. 28, 2006.
Faghihi et al., Expression of a noncoding RNA is elevated in Alzheimer's disease and drives rapid feed-forward regulation of [beta]-secretase. Nat Med. Jul. 2008;14(7):723-30. doi:10.1038/nm1784. Epub Feb. 23, 2010. 19 pages.
Francis et al., Reconstitution of a functional core polycomb repressive complex. Mol Cell. Sep. 2001;8(3):545-56.
Frieden et al., Expanding the design horizon of antisense oligonucleotides with alpha-L-LNA, Nucleic Acids Res., Nov. 1, 2003, 31(21):6365-72.
Froberg et al., Guided by RNAs: X-inactivation as a model for lncRNA function. J Mol Biol. Oct. 9, 2013;425(19):3698-706. doi: 10.1016/j.jmb.2013.06.031. Epub Jun. 28, 2013. Review. 15 pages.
Fu et al., Mir-144 selectively regulates embryonic alpha-hemoglobin synthesis during primitive erythropoiesis. Blood. Feb. 5, 2009;113(6):1340-9.
Golding et al., Depletion of Kcnq1ot1 non-coding RNA does not affect imprinting maintenance in stem cells. Development. 2011;138:3667-8. doi:10.1242/dev.057778.
Gontan et al., Long Noncoding RNAs and X Chromosome Inactivation. Prog Mol Subcell Biol. 2011;51:43-64. doi: 10.1007/978-3-642-16502-3_3.
Guo et al., High resolution genome wide binding event finding and motif discovery reveals transcription factor spatial binding constraints. PLoS Comput Biol. 2012;8(8):e1002638. doi: 10.1371/journal.pcbi.1002638. Epub Aug. 9, 2012.
Gupta et al., Long non-coding RNA HOTAIR reprograms chromatin state to promote cancer metastasis. Nature. Apr. 15, 2010;464(7291):1071-6. doi: 10.1038/nature08975. E-pub version.
Guttman et al., Chromatin signature reveals over a thousand highly conserved large non-coding RNAs in mammals. Nature. Mar. 12, 2009;458(7235):223-7. doi: 10.1038/nature07672. Epub Sep. 30, 2009. 13 pages.
Guttman et al., Modular regulatory principles of large non-coding RNAs. Nature. Feb. 15, 2012;482(7385):339-46. Review.
Hendrich et al., Evolutionary conservation of possible functional domains of the human and murine XIST genes. Human Molec Gen. 1993;2(6):663-72.
Horike et al., Targeted disruption of the human LIT1 locus defines a putative imprinting control element playing an essential role in Beckwith-Wiedemann syndrome. Hum Mol Genet. Sep. 1, 2000;9(14):2075-83.
Inesi et al., Studies of Ca2+ ATPase (SERCA) inhibition. J Bioenerg Biomembr. Dec. 2005;37(6):365-8. Review.
Inouye, Antisense RNA: its functions and applications in gene regulation—a review. Gene. Dec. 10, 1988;72(1-2):25-34.
Jeon et al., YY1 tethers Xist RNA to the inactive X nucleation center. Cell. Jul. 8, 2011;146(1):119-33. doi: 10.1016/j.cell.2011.06.026.
Jepsen et al., Locked nucleic acid: a potent nucleic acid analog in therapeutics and biotechnology. Oligonucleotides. 2004;14(2):130-46. Review.
Jia et al., Genome-wide computational identification and manual annotation of human long noncoding RNA genes. RNA. Aug. 2010;16(8):1478-87. doi: 10.1261/rna.1951310. Epub Jun. 29, 2010.
Johansson et al., Target-specific arrest of mRNA translation by antisense 2'-O-alkyloligoribonucleotides. Nucleic Acids Res. Nov. 11, 1994;22(22):4591-8.
Johnson, Long non-coding RNAs in Huntington's disease neurodegeneration. Neurobiol Dis. 2012;46:245-54.
Kanduri et al., The length of the transcript encoded from the Kcnq1ot1 antisense promoter determines the degree of silencing. EMBO J. 2006;25:2096-106.
Kanhere et al., Short RNAs are transcribed from repressed polycomb target genes and interact with polycomb repressive complex-2. Mol Cell. Jun. 11, 2010;38(5):675-88. doi: 10.1016/j.molcel.2010.03.019.
Kapranov et al., Genome-wide transcription and the implications for genomic organization. Nat Rev Genet. Jun. 2007, 8(6):413-23.
Kapranov et al., RNA maps reveal new RNA classes and a possible function for pervasive transcription. Science. Jun. 8, 2007;316(5830):1484-8.
Khalil et al., Many human large intergenic noncoding RNAs associate with chromatin-modifying complexes and affect gene expression. Proc Natl Acad Sci U S A. Jul. 14, 2009;106(28):11667-72.
Kim et al., Identification of clustered YY1 binding sites in imprinting control regions. Genome Res. Jul. 2006;16(7):901-11. Epub Jun. 7, 2006.
Klein et al., Homeostatic regulation of MeCP2 expression by a CREB-induced microRNA. Nat Neurosci. Dec. 2007;10(12):1513-4.
Krützfeldt et al., Silencing of microRNAs in vivo with 'antagomirs'. Nature. Dec. 1, 2005;438(7068):685-9. Epub Oct. 30, 2005.
Ku et al., Genomewide analysis of PRC1 and PRC2 occupancy identifies two classes of bivalent domains. PLoS Genet. Oct. 2008;4(10):e1000242. doi: 10.1371/journal.pgen.1000242. Epub Oct. 31, 2008. 14 pages.
Lee et al., A 450 kb Transgene Displays Properties of the Mammalian X-Inactivation Center. Cell. Jul. 12, 1996;86:83-94.
Lee et al., Control of developmental regulators by Polycomb in human embryonic stem cells. Cell. Apr. 21, 2006;125(2):301-13.
Lee et al., Genetic analysis of the mouse X inactivation center defines an 80-kb multifunction domain. Proc Natl Acad Sci U S A. Mar. 30, 1999;96(7):3836-41.
Lee et al., Targeted Mutagenesis of Tsix Leads to Nonrandom X Inactivation. Cell. Oct. 1, 1999;99:47-57.
Lee et al., Tsix, a gene antisense to Xist at the X-inactivation centre. Nat Genet. Apr. 1999;21:400-4.
Lee, Disruption of Imprinted X Inactivation by Parent-of-Origin Effects at Tsix. Cell. Sep. 29, 2000;103:17-27.
Lee, Epigenetic regulation by long noncoding RNAs. Science. Dec. 14, 2012;338(6113):1435-9. Review.
Lee, Homozygous Tsix mutant mice reveal a sex-ratio distortion and revert to random X-inactivation. Nat Genet. Sep. 2002;32:195-200.
Lee, Lessons from X-chromosome inactivation: long ncRNA as guides and tethers to the epigenome. Genes Dev. Aug. 15, 2009;23(16):1831-42. doi: 10.1101/gad.1811209.
Lee, The X as a Model for RNA's Niche in Epigenomic Regulation. Cold Spring Harb Perspect Biol. 2010;2:A003749. 12 pages.
Li et al., Jarid2 and PRC2, partners in regulating gene expression. Genes Dev. Feb. 15, 2010;24(4):368-80. doi: 10.1101/gad.1886410. Epub Feb. 1, 2010.
Lima et al., Single-stranded siRNAs activate RNAi in animals. Cell. Aug. 31, 2012;150(5):883-94. doi: 10.1016/j.cell.2012.08.014.
Lin et al., An in-depth map of polyadenylation sites in cancer. Nucleic Acids Res. Sep. 1, 2012;40(17):8460-71. Epub Jun. 29, 2012.
Lin et al., Asymmetric regulation of imprinting on the maternal and paternal chromosomes at the Dlk1-Gtl2 imprinted cluster on mouse chromosome 12. Nat Genet. Sep. 2003;35(1):97-102. Epub Aug. 24, 2003.
Lipovich et al., MacroRNA underdogs in a microRNA world: evolutionary, regulatory, and biomedical significance of mammalian long non-protein-coding RNA. Biochim Biophys Acta. Sep. 2010;1799(9):597-615. Review.

(56) References Cited

OTHER PUBLICATIONS

Margueron et al., The Polycomb complex PRC2 and its mark in life. Nature. Jan. 20, 2011;469(7330):343-9. Review.
Mercer et al., Long non-coding RNAs: insights into functions. Nat Rev Genet. Mar. 2009;10(3):155-9. Review.
Mercer et al., Structure and function of long noncoding RNAs in epigenetic regulation. Mar. 5, 2013;20:300-7.
Merienne et al., SCA8 CAG/CTG expansions, a tale of two TOXICities: a unique or common case? PLoS Genet. Aug. 2009;5(8):e1000593. doi: 10.1371/journal.pgen.1000593. Epub Aug. 14, 2009.
Miremadi et al., Cancer genetics of epigenetic genes. Hum Mol Genet. Apr. 15, 2007;16 Spec No. 1:R28-49. Review.
Miura et al., Utrophin upregulation for treating Duchenne or Becker muscular dystrophy: how close are we? Trends Mol Med. Mar. 2006;12(3):122-9. Epub Jan. 27, 2006.
Modarresi et al., Natural Antisense Inhibition Results in Transcriptional De-Repression and Gene Upregulation. Nat Biotechnol. Mar. 25, 2012;30(5):453-9. doi: 10.1038/nbt.2158. 21 pages.
Montgomery et al., The murine polycomb group protein Eed is required for global histone H3 lysine-27 methylation. Curr Biol. May 24, 2005;15(10):942-7.
Morris et al., Small interfering RNA-induced transcriptional gene silencing in human cells. Science. Aug. 27, 2004;305(5688):1289-92. Epub Aug. 5, 2004.
Morris, RNA-mediated transcriptional gene silencing in human cells. Curr Top Microbiol Immunol. 2008;320:211-24. Review.
Munroe, Antisense RNA inhibits splicing of pre-mRNA in vitro. EMBO J. Aug. 1988; 7(8): 2523-32.
Nagano et al., The Air noncoding RNA epigenetically silences transcription by targeting G9a to chromatin. Science. Dec. 12, 2008;322(5908):1717-20.
Nie et al., Long non-coding RNAs: versatile master regulators of gene expression and crucial players in cancer. Am J Transl Res. 2012;4(2):127-50. Epub Apr. 8, 2012.
Numata et al., Comparative analysis of cis-encoded antisense RNAs in eukaryotes. Gene. May 1, 2007;392(1-2):134-41.
Numata et al., Identification of novel endogenous antisense transcripts by DNA microarray analysis targeting complementary strand of annotated genes. BMC Genomics. Aug. 22, 2009;10:392. doi: 10.1186/1471-2164-10-392.
Okada et al., Comparative expression analysis uncovers novel features of endogenous antisense transcription. Hum Mol Genet. Jun. 1, 2008;17(11):1631-40. doi: 10.1093/hmg/ddn051. Epub Feb. 18, 2008.
Ørom et al., LNA-modified oligonucleotides mediate specific inhibition of microRNA function. Gene. May 10, 2006;372:137-41. Epub Feb. 24, 2006.
Ozsolak et al., Comprehensive polyadenylation site maps in yeast and human reveal pervasive alternative polyadenylation. Cell. Dec. 10, 2010;143(6):1018-29. doi: 10.1016/j.cell.2010.11.020.
Pandey et al., Kcnq1ot1 antisense noncoding RNA mediates lineage-specific transcriptional silencing through chromatin-level regulation. Mol Cell. Oct. 24, 2008;32(2):232-46. doi: 10.1016/j.molcel.2008.08.022.
Paro et al., Extending the frontiers of epigenetic regulation. Curr Opin Genet Dev. Apr. 2010;20(2):107-9. doi: 10.1016/j.gde.2010.03.011.
Pasini et al., Suz12 is essential for mouse development and for EZH2 histone methyltransferase activity. EMBO J. Oct. 13, 2004;23(20):4061-71. Sep. 23, 2004.
Peng et al., Jarid2/Jumonji coordinates control of PRC2 enzymatic activity and target gene occupancy in pluripotent cells. Cell. Dec. 24, 2009;139(7):1290-302. doi: 10.1016/j.cell.2009.12.002. Epub Jul. 29, 2010 24 pages.
Penny et al., Requirement for Xist in X chromosome inactivation. Nature. Jan. 11, 1996;379(6561):131-7.
Pereira et al., Ezh2, the histone methyltransferase of PRC2, regulates the balance between self-renewal and differentiation in the cerebral cortex. Proc Natl Acad Sci U S A. Sep. 7, 2010;107(36):15957-62. doi: 10.1073/pnas.1002530107. Epub Aug. 23, 2010.
Petersen et al., LNA: A versatile tool for therapeutics and genomics. Trends Biotech. Feb. 2003;21(2):74-81. Review.
Pietersen et al., Stem cell regulation by polycomb repressors: postponing commitment. Curr Opin Cell Biol. Apr. 2008;20(2):201-7. doi: 10.1016/j.ceb.2008.01.004. Epub Mar. 4, 2008. Review.
Plath et al., Role of Histone H3 Lysine 27 Methylation in X Inactivation. Science. Apr. 4, 2003;300:131-5. doi: 10.1126/science.1084274.
Ponting et al., Evolution and functions of long noncoding RNAs. Cell. Feb. 20, 2009;136(4):62941. doi: 10.1016/j.cell.2009.02.006. Review.
Qi et al., Repurposing CRISPR as an RNA-guided platform for sequence-specific control of gene expression. Cell. Feb. 28, 2013;152(5):1173-83. doi: 10.1016/j.cell.2013.02.022.
Rajasekhar et al., Concise review: roles of polycomb group proteins in development and disease: a stem cell perspective. Stem Cells. Oct. 2007;25(10):2498-510. Epub Jun. 28, 2007. Review.
Redrup et al., The long noncoding RNA Kcnq1ot1 organises a lineage-specific nuclear domain for epigenetic gene silencing. Development. Feb. 2009;136(4):525-30. doi: 10.1242/dev.031328. Epub Jan. 14, 2009. 14 pages.
Ringrose et al., Epigenetic regulation of cellular memory by the Polycomb and Trithorax group proteins. Annu Rev Genet. 2004;38:413-43. Review.
Rinn et al., Functional demarcation of active and silent chromatin domains in human HOX loci by noncoding RNAs. Cell. Jun. 29, 2007;129(7):1311-23.
Rinn et al., Genome Regulation by Long Noncoding RNAs. Annu Rev Biochem. 2012;81:145-66.
Røsok et al., Systematic identification of sense-antisense transcripts in mammalian cells. Nat Biotechnol. Jan. 2004;22(1):104-8. Epub Dec. 14, 2004.
Sankaran et al., MicroRNA-15a and -16-1 act via MYB to elevate fetal hemoglobin expression in human trisomy 13. Proc Natl Acad Sci U S A. Jan. 25, 2011;108(4):1519-24.
Sankaran, Targeted therapeutic strategies for fetal hemoglobin induction. Hematol Am Soc Hematol Educ Program. 2011;2011:459-65.
Sarma et al., Locked nucleic acids (LNAs) reveal sequence requirements and kinetics of Xist RNA localization to the X chromosome. Proc Natl Acad Sci U S A. Dec. 21, 2010;107(51):22196-201. doi: 10.1073/pnas.1009785107. Epub Dec. 6, 2010.
Saxena et al., Long non-coding RNA modifies chromatin. Bioessays. 2011;33:830-9. Review.
Schoeftner et al., Recruitment of PRC1 function at the initiation of X inactivation independent of PRC2 and silencing. EMBO J. Jul. 12, 2006;25(13):3110-22. Epub Jun. 8, 2006.
Schuettengruber et al., Genome regulation by polycomb and trithorax proteins. Cell. Feb. 23, 2007;128(4):735-45.
Schultz et al., Enhancers compete with a long non-coding RNA for regulation of the Kcnq1 domain. Nucl Acids Res. 2015;43(2):745-59.
Schwartz et al., Genome-wide analysis of Polycomb targets in *Drosophila melanogaster*. Nat Genet. Jun. 2006;38(6):700-5.
Schwartz et al., Polycomb complexes and epigenetic states. Curr Opin Cell Biol. 2008;20:266-73. doi: 10.1016/j.ceb.2008.03.002.
Seong et al., Huntingtin facilitates polycomb repressive complex 2. Hum Mol Genet. Feb. 15, 2010;19(4):573-83. doi: 10.1093/hmg/ddp524. Epub Nov. 23, 2009.
Shaver et al., Origin of the polycomb repressive complex 2 and gene silencing by an E(z) homolog in the unicellular alga Chlamydomonas. Epigenetics. May 16, 2010;5(4):301-12. Epub May 24, 2010.
Shen et al,. EZH1 mediates methylation on histone H3 lysine 27 and complements EZH2 in maintaining stem cell identity and executing pluripotency. Mol Cell. Nov. 21, 2008;32(4):491-502. doi: 10.1016/j.molcel.2008.10.016.
Shen et al., Jumonji modulates polycomb activity and self-renewal versus differentiation of stem cells. Cell. Dec. 24, 2009;139(7):1303-14. doi: 10.1016/j.cell.2009.12.003. Epub Jun. 24, 2010. 26 pages.
Shore et al., Pregnancy-induced noncoding RNA (PINC) associates with polycomb repressive complex 2 and regulates mammary epithelial differentiation. PLoS Genet. 2012;8(7):e1002840. doi: 10.1371/journal.pgen.1002840. Epub Jul. 26, 2012.

(56) References Cited

OTHER PUBLICATIONS

Simon et al., High-resolution Xist binding maps reveal two-step spreading during X-chromosome inactivation. Nature. Dec. 19, 2013;504(7480):465-9. doi: 10.1038/nature12719. Epub Oct. 27, 2013.
Simon et al., Roles of the EZH2 histone methyltransferase in cancer epigenetics. Mutat Res. Dec. 1, 2088;647(1-2):21-9. Review.
Sing et al., A vertebrate Polycomb response element governs segmentation of the posterior hindbrain. Cell. Sep. 4, 2009;138(5):885-97. doi: 10.1016/j.cell.2009.08.020.
Sparmann et al., Polycomb silencers control cell fate, development and cancer. Nat Rev Cancer. Nov. 2006;6(11):846-56. Review.
Taft et al., Non-coding RNAs: regulators of disease. J Pathol. Jan. 2010;220(2):126-39. doi: 10.1002/path.2638. Review.
Taft et al., Tiny RNAs associated with transcription start sites in animals. Nat Genet. May 2009;41(5):572-8. doi: 10.1038/ng.312. Epub Apr. 19, 2009. Erratum in: Nat Genet. Jul. 2009;41(7):859.
Takagi et al., Role of Sp1 in transcription of human ATP2A2 gene in keratinocytes. J Invest Dermatol. Jan. 2008;128(1):96-103. Epub Jun. 28, 2007.
Takahashi et al., Deletion of Gtl2, imprinted non-coding RNA, with its differentially methylated region induces lethal parent-origin-dependent defects in mice. Hum Mol Genet. May 15, 2009;18(10):1879-88. doi: 10.1093/hmg/ddp108. Epub Mar. 4, 2009.
Tano et al., MALAT-1 enhances cell motility of lung adenocarcinoma cells by influencing the expression of motility-related genes. FEBS Lett. Nov. 19, 2010;584(22):4575-80. doi: 10.1016/j.febslet.2010.10.008. Epub Oct. 13, 2010.
Thorvaldsen et al., A YY1 bridge for X inactivation. Cell. Jul. 8, 2011;146(1):11-3. doi: 10.1016/j.cell.2011.06.029.
Thorvaldsen et al., SnapShot: imprinted gene clusters. Cell. Sep. 7, 2007;130(5):958.
Tian et al., The long noncoding RNA, Jpx, is a molecular switch for X chromosome inactivation. Cell. Oct. 29, 2010;143(3):390-403. doi: 10.1016/j.cell.2010.09.049. 21 pages.
Tsai et al., Higher order chromatin structure at the X-inactivation center via looping DNA. Dev Biol. Jul. 15, 2008;319(2):416-25. doi: 10.1016/j.ydbio.2008.04.010. Epub Apr. 18, 2008. 22 pages.
Tsai et al., Long noncoding RNA as modular scaffold of histone modification complexes. Science. Aug. 6, 2010;329(5992):689-93. doi: 10.1126/science.1192002. Epub Nov. 2, 2010. 9 pages.
Vickers et al., Fully modified 2' MOE oligonucleotides redirect polyadenylation. Nucleic Acids Res. Mar. 15, 2001;29(6):1293-9.
Wahlestedt, Natural antisense and noncoding RNA transcripts as potential drug targets. Drug Discov Today. Jun. 2006;11(11-12):503-8.
Wahlestedt, Targeting long non-coding RNA to therapeutically upregulate gene expression. Nature Rev Drug Disc. Jun. 2013;12:433-46. Review.
Wan et al., Regulation of imprinting in clusters: noncoding RNAs versus insulators. Adv Genet. 2008;61:207-23. Review.
Wang et al., Long non-coding RNA UCA1a(CUDR) promotes proliferation and tumorigenesis of bladder cancer. Int J Oncol. Jul. 2012;41(1):276-84.
Wang et al., Molecular mechanisms of long noncoding RNAs. Cell Press. Sep. 16, 2011; 43(6):904-14.
Williamson et al., Identification of an imprinting control region affecting the expression of all transcripts in the Gnas cluster. Nat Genet. Mar. 2006;38(3):350-5.
Wilusz et al., A triple helix stabilizes the 3' ends of long noncoding RNAs that lack poly(A) tails. Genes Dev. Nov. 1, 2012;26(21):2392-407. doi: 10.1101/gad.204438.112. Epub Oct. 16, 2012.
Woo et al., A Region of theHuman HOXDCluster that Confers Polycomb-Group Responsiveness. Cell. Jan. 8, 2010;140:99-110.
Wutz et al., A Shift from Reversible to Irreversible X Inactivation Is Triggered during ES Cell Differentiation. Molec Cell. Apr. 2000;5:695-705.

Xiong et al., Polycomb antagonizes p300/CREB-binding protein associated factor to silence FOXP3 in a Kruppel-like factor-dependent manner. J Biol Chem. Oct. 5, 2012;287(41):34372-85. doi: 10.1074/jbc.M111.325332. Epub Aug. 15, 2012.
Yang et al., Long noncoding RNAs: fresh perspectives into the RNA world. Trends Biochem Sci. Jan. 2014;39(1):35-43. doi: 10.1016/j.tibs.2013.10.002. Epub Nov. 27, 2013. Review.
Yap et al., Molecular interplay of the noncoding RNA ANRIL and methylated histone H3 lysine 27 by polycomb CBX7 in transcriptional silencing of INK4a. Mol Cell. Jun. 11, 2010 ;38(5):662-74. doi: 10.1016/j.molcel.2010.03.021. Epub Jun. 11, 2011. 23 pages.
Yatsuki et al., Sequence-based structural features between Kvlqt1 and Tapa1 on mouse chromosome 7F4/F5 corresponding to the Beckwith-Wiedemann syndrome region on human 11p15.5: long-stretches of unusually well conserved intronic sequences of kvlqt1 between mouse and human. DNA Res. Jun. 30, 2000;7(3):195-206.
Yu et al., Single-stranded RNAs use RNAi to potently and allele-selectively inhibit mutant huntingtin expression. Cell. Aug. 31, 2012;150(5):895-908. doi: 10.1016/j.cell.2012.08.002.
Zhang et al., Long noncoding RNA-mediated intrachromosomal interactions promote imprinting at the Kcnq1 locus. J Cell Biol. 2014;204(1):61-75.
Zhang et al., NATsDB: Natural Antisense Transcripts DataBase. Nucleic Acids Res. Jan. 2007;35(Database issue):D156-61. Epub Nov. 1, 2006.
Zhang et al., Perinucleolar Targeting of the Inactive X during S Phase: Evidence for a Role in the Maintenance of Silencing. Cell. May 18, 2007;129:693-706.
Zhao et al., Genome-wide identification of polycomb-associated RNAs by RIP-seq. Mol Cell. Dec. 22, 2010;40(6):939-53.
Zhao et al., Polycomb proteins targeted by a short repeat RNA to the mouse X-chromosome. Science. 2008; 322(5902):750-756. doi:10.1126/science.1163045. E-pub version.
Submission. EBI Accession No. EMBL:GC092872. Palma et al. Aug. 31, 2008.
Genbank Submission; NCBI, Accession No. AM911724.1; Talwar et al. Nov. 26, 2007.
Genbank Submission; NCBI, Accession No. NM_022876.2. Apr. 2010. 5 pages.
[No Author Listed], New England BioLabs 1998/99 Catalog. 121, 284.
[No Author Listed] Catalogue of Parent of Origin Effects, Imprinted Genes and Related Effects, Parental Origins of de novo Mutations, downloaded at http://igc.otago.ac.nz/home.html on May 22, 2015, 2 pgs.
[No Author Listed] Locked Nucleic Acid. Exiqon. 2009. Retrieved from http://www.exiqon.com/ls/documents/scientific/lna_folder.pdf on Jun. 6, 2016.
[No Author Listed] UCSC Genome Browser on Human Feb. 2009 (GRCh37/hg19) Assembly. Retrieved from http://genome.ucsc.edu/cgi-bin/hgTracks?db=hgl 9&position=chr5%3A 702 11 956-7027 1 955&hgsid=452570083 _sxavccF ldzrwhzM3tcNOyMcxbye 7 on Nov. 9, 2015.
Aartsma-Rus et al., Antisense-induced multiexon skipping for Duchenne muscular dystrophy makes more sense. Am J Hum Genet. Jan. 2004;74(1):83-92.
Bauer et al., The quest for mammalian Polycomb response elements: are we there yet? Chromosoma. Jun. 2016;125(3):471-96. doi:10.1007/s00412-015-0539-4.
Buck et al., Design strategies and performance of custom DNA sequencing primers. Biotechniques. Sep. 1999;27(3):528-36.
Crea et al., Pharmacologic disruption of Polycomb Repressive Complex 2 inhibits tumorigenicity and tumor progression in prostate cancer. Mol Cancer. Apr. 18, 2011;10:40. doi: 10.1186/14764598-10-40.
Davidovich et al., Toward a consensus on the binding specificity and promiscuity of PRC2 for RNA. Mol Cell. Feb. 5, 2015;57(3):552-8. doi: 10.1016/j.molcel.2014.12.017. Epub Jan. 15, 2015.
Dheda et al., Validation of housekeeping genes for normalizing RNA expression in real-time PCR. Biotechniques. Jul. 2004;37(1):112-4, 116, 118-9.
Dias et al., Antisense oligonucleotides: basic concepts and mechanisms. Mol Cancer Ther. Mar. 2002;1(5):347-55.

(56) References Cited

OTHER PUBLICATIONS

Ebralidze et al., PU.1 expression is modulated by the balance of functional sense and antisense RNAs regulated by a shared cis-regulatory element. Genes Dev. Aug. 1, 2008;22(15):2085-92. doi:10.1101/gad.1654808. Supplemental Data.
Eddy, Non-coding RNA genes and the modern RNA world. Nat Rev Genet. Dec. 2001;2(12):919-29.
Fish et al., Hypoxia-inducible expression of a natural cis-antisense transcript inhibits endothelial nitric-oxide synthase. J Biol Chem. May 25, 2007;282(21):15652-66. Epub Apr. 2, 2007.
Gajera et al., Molecular and biochemical characterization of Trichoderma isolates inhibiting a phytopathgenic fungi *Asperillus niger* Van Tieghem. Phys Mol Plant Path. 2010;74:274-282.
Hernandez et al., Degradation of nuclease-stabilized RNA oligonucleotides in Mycoplasma-contaminated cell culture media. Nucleic Acid Ther. Feb. 2012;22(1):58-68. doi: 10.1089/nat.2011.0316. Epub Jan. 9, 2012.
Huang, Shoujun et al., Non-encoding RNA and development of animals, Science China Life Science, Dec. 31, 2009; pp. 21-30.
Inoue et al., Synthesis and hybridization studies on two complementary nona(2'-O-methyl)ribonucleotides. Nucleic Acids Res. Aug. 11, 1987;15(15):6131-48.
Jackson et al., Expression profiling reveals off-target gene regulation by RNAi. Nat Biotechnol. Jun. 2003;21(6):635-7. Epub May 18, 2003.
Keil et al., A short antisense oligonucleotide ameliorates symptoms of severe mouse models of spinal muscular atrophy. Mol. Ther Nucleic Acids. Jul. 8, 2014;3:e174. doi: 10.1038/mtna.2014.23.
Kierzek et al., The influence of locked nucleic acid residues on the thermodynamic properties of 2'-O-methyl RNA/RNA heteroduplexes. Nucleic Acids Res. Sep. 9, 2005 ;33(16):5082-93. Print 2005.
Lacerra et al., Restoration of hemoglobin A synthesis in erythroid cells from peripheral blood of thalassemic patients. Proc Natl Acad Sci U S A. Aug. 15, 2000;97(17):9591-6.
Lapointe et al., Gene expression profiling identifies clinically relevant subtypes of prostate cancer. Proc Natl Acad Sci U S A. Jan. 20, 2004;101(3):811-6. Epub Jan. 7, 2004.
Latorra et al., Design considerations and effects of LNA in PCR primers. Mol Cell Probes. Oct. 2003;17(5):253-9.
Lennox et al., Improved Performance of Anti-miRNA Oligonucleotides Using a Novel Non-Nucleotide Modifier. Mol Ther Nucleic Acids. Aug. 27, 2013;2:e117. doi: 10.1038/mtna.2013.46.
Morse et al., Depleting regulatory T cells with arginine-rich, cell-penetrating, peptide-conjugated morpholino oligomer targeting FOXP3 inhibits regulatory T-cell function. Cancer Gene Ther. Jan. 2012;19(1):30-7. doi: 10.1038/cgt.2011.63.
Nishida et al., Synthesis, RNA selective hybridization and high nuclease resistance of an oligonucleotide containing novel bridged nucleic acid with cyclic urea structure. Chem Commun (Camb). Aug. 7, 2010;46(29):5283-5. doi: 10.1039/c0cc00154f. Epub Jun. 22, 2010.
Rozen et al., Primer3 on the WWW for general users and for biologist programmers. Methods Mol Biol. 2000;132:365-86.
Schadt et al., An integrative genomics approach to infer causal associations between gene expression and disease. Nat Genet. Jul. 2005;37(7):710-7. Epub Jun. 19, 2005.
Schwartz et al., Polycomb silencing mechanisms and the management of genomic programmes. Nat Rev Genet. Jan. 2007;8(1):9-22.
Singh et al., A short antisense oligonucleotide masking a unique intronic motif prevents skipping of a critical exon in spinal muscular atrophy. RNA Biol. Jul.-Aug. 2009;6(3):341-50. Epub Jul. 14, 2009
Suwanmanee et al., Restoration of human beta-globin gene expression in murine and human IVS2-654 thalassemic erythroid cells by free uptake of antisense oligonucleotides. Mol Pharmacol. Sep. 2002;62(3):545-53.
Varela et al., Natural Antisense Makes Sense for Gene-specific Activation in Brain. Mol Ther Nucleic Acids. May 15, 2012;1:e24. doi: 10.1038/mtna.2012.17.
Venter et al., The sequence of the human genome. Science. Feb. 16, 2001;291(5507):1304-51. Erratum in: Science Jun. 5, 2001;292(5523):1838.
Whitehead et al., Variation in tissue-specific gene expression among natural populations. Genome Biol. 2005;6(2):R13. Epub Jan. 26, 2005
Wilusz et al., Long noncoding RNAs: functional surprises from the RNA world. Genes Dev. Jul. 1, 2009;23(13):1494-504. doi:10.1101/gad.1800909.
Yang et al., High fidelity PCR with an off/on switch mediated by proofreading polymerases combining with phosphorothioate-modified primer. Biochem Biophys Res Commun. Mar. 4, 2005;328(1):265-72. Erratum in: Biochem Biophys Res Commun. Jun. 3, 2005;331(2):682. Zhang, Jia [removed]; Li, Kai [removed].
Yang et al., The histone code regulating expression of the imprinted mouse Igf2r gene. Endocrinology. Dec. 2003;144(12):5658-70.
[No Author Listed] Designing Antisense Oligonucleotides. Integrated DNA Technologies. 2011. 1-16.
[No Author Listed] ncRNA. 2011;29(11):1716-1721.
Alvarez-Salas, Nucleic acids as therapeutic agents. Curr Top Med Chem. 2008;8(15):1379-404.
Behlke et al., Designing antisense oligonucleotides. Integrated DNA Technologies. 2005. 1-17.
Beltran et al., The interaction of PRC2 with RNA or chromatin is mutually antagonistic. Genome Res. Jul. 2016;26(7):896-907. doi:10.1101/gr.197632.115. Epub May 9, 2016.
Braasch et al., Locked nucleic acid (LNA): fine-tuning the recognition of DNA and RNA. Chem Biol. Jan. 2001:8(1):1-7.
Broderick et al., MicroRNA therapeutics. Gene Ther. Dec. 2011;18(12):1104-10. doi: 10.1038/gt.2011.50. Epub Apr. 28, 2011.
Cantafora et al., Evaluation of RNA messengers involved in lipid trafficking of human intestinal cells by reverse-transcription polymerase chain reaction with competimer technology and microchip electrophoresis. Electrophoresis. Nov. 2003;24(21):3748-54.
Crooke et al., Kinetic characteristics of *Escherichia coil* RNase H1: cleavage of various antisense oligonucleotide-RNA duplexes. Biochem J. Dec. 1, 1995;312 ( Pt 2):599-608.
Cuddapah et al., A novel human polycomb binding site acts as a functional polycomb response element in *Drosophila*. PLoS One. 2012;7(5):e36365. doi: 10.1371/journal.pone.0036365. Epub May 3, 2012.
Cushman et al., Synthesis of the covalent hydrate of the incorrectly assumed structure of aurintricarboxylic acid (ATA). Tetrahedron. 1990;46(5):1491-1498.
Davidovich et al., The recruitment of chromatin modifiers by long noncoding RNAs: lessons from PRC2. RNA. Dec. 2015;21(12):2007-22. doi:10.126/rna.053918.115.
Ganguli et al., Antagomirbase—a putative antagomir database. Bioinformation. 2011;7(1):41-3.
Halley et al., Natural antisense transcripts as therapeutic targets. Drug Discov Today Ther Strateg. 2013 Fall;10(3):e119-e125.
He et al., Polycomb repressive complex 2 regulates normal development of the mouse heart. Circ Res. Feb. 3, 2012;110(3):406-15. doi: 10.1161/CIRCRESAHA.111.252205. Epub Dec. 8, 2011.
Kao et al., Tumor necrosis factor-alpha decreases sarcoplasmic reticulum Ca2+-ATPase expressions via the promoter methylation in cardiomyocytes. Crit Care Med. Jan. 2010;38(1):217-22. doi: 10.1097/CCM.0b013e3181b4a854.
Kiss, Small nucleolar RNA-guided post-transcriptional modification of cellular RNAs. EMBO J. Jul. 16, 2001;20(14):3617-22.
Kutyavin et al., Reduced aggregation and improved specificity of G-rich oligodeoxyribonucleotides containing pyrazolo[3,4-d]pyrimidine guanine bases. Nucleic Acids Res. Nov. 15, 2002;30(22):4952-9.
Li et al., CTCF regulates allelic expression of Igf2 by orchestrating a promoter-polycomb repressive complex 2 intrachromosomal loop. Mol Cell Biol. Oct. 2008;28(20):6473-82. doi: 10.1128/MCB.00204-08. Epub Jul. 28, 2008.
Mencia et al., Mutations in the seed region of human miR-96 are responsible for nonsyndromic progressive hearing loss. Nat Genet. May 2009;41(5):609-13. doi: 10.1038/ng.355. Epub Apr. 12, 2009.

(56) References Cited

OTHER PUBLICATIONS

Mendenhall et al., GC-rich sequence elements recruit PRC2 in mammalian ES cells. PLoS Genet. Dec. 9, 2010;6(12):e1001244. doi: 10.1371/journal.pgen.1001244.

Mirguet et al., From ApoA1 upregulation to BET family bromodomain inhibition:discovery of I-BET151. Bioorg Med Chem Lett. Apr. 15, 2012;22(8):2963-7. doi:10.1016/j.bmcl.2012.01.125. Epub Feb. 8, 2012.

Nakao, Gene Cluster control through epigenetic mechanisms and cytopathology. Uehara memorial life science foundation research report collection. 23;2009:1-4.

Prensner et al., Transcriptome sequencing across a prostate cancer cohort identifies PCAT-1, an unannotated lincRNA implicated in disease progression. Nat Biotechnol. Jul. 31, 2011;29(8):742-9. doi: 10.1038/nbt.1914.

Rader, Molecular regulation of HDL metabolism and function: implications for novel therapies. J Clin Invest. Dec. 2006;116(12):3090-100.

Schlesinger et al., Polycomb-mediated methylation on Lys27 of histone H3 pre-marks genes for de novo methylation in cancer. Nat Genet. Feb. 2007;39(2):232-6. Epub Dec. 31, 2006.

Summerton, Morpholino antisense oligomers: the case for an Rnase H-independent structural type. Biochim Biophys Acta. Dec. 10, 1999;1489(1):141-58.

Sun et al., Evidence for a preferential targeting of 3'-UTRs by cis-encoded natural antisense transcripts. Nucleic Acids Res. Oct. 4, 2005;33(17):5533-43. Print 2005.

Sun et al., SNPs in human miRNA genes affect biogenesis and function. RNA. Sep. 2009;15(9):1640-51. doi: 10.1261/rna.1560209. Epub Jul. 17, 2009.

Tae et al., Bromodomain protein 7 interacts with PRMT5 and PRC2, and is involved in transcriptional repression of their target genes. Nucleic Acids Res. Jul. 2011;39(13):5424-38. doi: 10.1093/nar/gkr170.

Van Peer et al., miRBase Tracker: keeping track of microRNA annotation changes. Database (Oxford). Aug. 25, 2014;2014. pii:bau080. doi: 10.1093/database/bau080. Print 2014.

Woo et al., Gene activation of SMN by selective disruption of lncRNA-mediated recruitment of PRC2 for the treatment of spinal muscular atrophy. Proc Natl Acad Sci U S A. Feb. 21, 2017;114(8):E1509-E1518. doi:10.1073/pnas.1616521114. Epub Feb. 13, 2017.

Wu et al., Binding interactions between long noncoding RNA HOTAIR and PRC2 proteins. Biochemistry. Dec. 31, 2013;52(52):9519-27. doi: 10.1021/bi401085h.

Yakali et al., Supramolecular chirality-sensing DNA-mimicry of a norbornane derivative decorated with isoxazoline and methylpyrrolidine-2,5-dione ring. J Mol Structure. Jun. 10, 2013;1041:164-174.

Zhou et al., Targeting RNA-splicing for SMA treatment. Mol Cells. Mar. 2012;33(3):223-8. doi: 10.1007/s10059-012-0005-6.

Arvey et al., Inflammation-induced repression of chromatin bound by the transcription factor Foxp3 in regulatory T cells. Nat Immunol. Jun. 2014;15(6):580-587. doi: 10.1038/ni.2868. Epub Apr. 13, 2014.

Efthymiou et al., Chemical architecture and applications of nucleic acid derivatives containing 1, 2, 3-triazole functionalities synthesized via click chemistry. Molecules. 2012;17(11):12665-12703.

Gooding et al., Oligonucleotide conjugates-Candidates for gene silencing therapeutics. European J Pharmaceutics Biopharmaceutics. 2016;107:321-340. [Epub.]Aug. 10, 2016.

He et al., Conjugation and Evaluation of Triazole-Linked Single Guide RNA for CRISPR-Cas9 Gene Editing. ChemBioChem, 2016;17:1809-1812.

Jayaprakash et al., Non-nucleoside building blocks for copper-assisted and copper-free click chemistry for the efficient synthesis of RNA conjugates. Organic Letters. 2010;12(23):5410-5413.

Matsuda et al., siRNA conjugates carrying sequentially assembled trivalent N-acetylgalactosamine linked through nucleosides elicit robust gene silencing in vivo in hepatocytes. ACS Chemical Biology. 2015;10:1181-1187.

Nair et al., Multivalent N-acetylgalactosamine-conjugated siRNA localizes in hepatocytes and elicits robust RNAi-mediated gene silencing. J American Chemical Society. 2014;136;16958-16961.

Thomas et al., Development of apolipoprotein B antisense molecules as a therapy for hyperlipidemia. Curr Atheroscler Rep. Jan. 2010;12(1):58-65. doi: 10.1007/s11883-009-0078-7.

\* cited by examiner

COMPOSITIONS AND METHODS FOR MODULATING HEMOGLOBIN GENE FAMILY EXPRESSION

CROSS-REFERENCE TO RELATED APPLICATIONS

This application is a national stage filing under U.S.C. § 371 of PCT International Application PCT/US2013/041382, with an international filing date of May 16, 2013, which claims the benefit under 35 U.S.C. § 119(e) of U.S. Provisional Application No. 61/785,956, entitled "COMPOSITIONS AND METHODS FOR MODULATING HEMOGLOBIN GENE FAMILY EXPRESSION", filed Mar. 14, 2013 and U.S. Provisional Application No. 61/647,901, entitled "COMPOSITIONS AND METHODS FOR MODULATING HEMOGLOBIN GENE FAMILY EXPRESSION", filed May 16, 2012, each of which is incorporated herein by reference in its entirety.

GOVERNMENT SUPPORT

This invention was made with Government support under Grant No. R01-GM-090278 awarded by the National Institutes of Health. The Government has certain rights in the invention.

FIELD OF THE INVENTION

The invention relates to oligonucleotide based compositions, as well as methods of using oligonucleotide based compositions for treating disease.

BACKGROUND OF THE INVENTION

Red blood cells are essential for transporting oxygen throughout the body. Red blood cells are made up of hemoglobin, which is a multi-subunit oxygen-transport metalloprotein. During development, embryonic hemoglobin is composed of epsilon chains (encoded by HBE1) and zeta chains and is produced by the embryonic yolk sac. In human infants, hemoglobin is made up of alpha chains (encoded by HBA1 and HBA2) and gamma chains (encoded by HBG1 and HBG2), with the gamma chains gradually replaced by beta chains over time. The majority of hemoglobin in adults is made up of alpha chains and beta chains (encoded by HBB) with a small percentage (about 3%) made up of alpha and delta chains (encoded by HBD). Several disorders are caused by mutations in hemoglobin subunits and affect red blood cell function or production, resulting in anemia. Two major diseases that affect red blood cells include sickle cell anemia and thalassemia.

Sickle cell anemia is a recessive disorder caused by the absence of a polar amino acid at position six of the beta-globin chain due to a point mutation in HBB. The absence of this amino acid causes aggregation of hemoglobin and results in red blood cells having a stiff, sickle shape. The rigidity of these red blood cells results in vessel occlusion and ischaemia as the cells pass through capillary beds. Anemia is also a symptom, due to the excessive lysis of sickle-shaped red blood cells. Mouse models of sickle cell anemia have shown that expression of other hemoglobin subunits can alleviate symptoms. In adult sickle cell anemia mice, for example, expression of HBE1, which is normally not expressed in adults but serves a similar function as beta-chains during embryonic development, restores the mice to a normal phenotype.

Thalassemia is a group of hereditary blood disorders characterized by a reduced amount of hemoglobin and fewer red blood cells. There are several types of thalassemia, including alpha-thalassemia, beta-thalassemia, delta thalassemia. Alpha-thalassemia is caused by mutations in the HBA1 or HBA2 gene. These mutations cause reduction in alpha-globin production and formation of beta-chain tetramers with altered oxygen profiles and anemia. Delta-thalassemia is caused by a reduction in the synthesis of delta chains of hemoglobin, which is encoded by HBD. Beta-thalassemia, the most severe form of thalassemia, is caused by a reduction in the synthesis of the beta chains of hemoglobin, which is encoded by HBB. Beta-thalassemia is classified into three types, thalassemia minor, thalassemia intermedia, and thalassemia major, depending on the number of mutations and disease severity. Thalassemia minor occurs when only one beta globin allele is mutated and results in microcytic anemia. When more than one allele is mutated, thalassemia intermedia or thalassemia major can occur depending on the severity of the mutation. Patients with thalassemia major require blood transfusions or bone marrow transplantation, otherwise anemia, splenomegaly, and severe bone deformities occur. Patients with thalassemia intermedia may require blood transfusions depending on the severity of the disease.

SUMMARY OF THE INVENTION

Aspects of the invention disclosed herein provide methods and compositions that are useful for upregulating hemoglobin genes (HBB, HBD, HBE1, HBG1, and/or HBG2) in cells. In some embodiments, single stranded oligonucleotides are provided that target a PRC2-associated region of a hemoglobin gene (e.g., human HBB, human HBD, human HBE1, human HBG1, human HBG2) and thereby cause upregulation of the gene. In some embodiments, single stranded oligonucleotides are provided that target a PRC2-associated region of the gene encoding a hemoglobin gene. In some embodiments, these single stranded oligonucleotides activate or enhance expression of a hemoglobin gene by relieving or preventing PRC2 mediated repression of the hemoglobin gene.

Upregulation of hemoglobin subunits is provided as a treatment for anemia, sickle cell anemia and/or thalassemia. Aspects of the invention disclosed herein provide methods and compositions that are useful for upregulating a hemoglobin gene, e.g., HBB, HBD, HBE1, HBG1, and/or HBG2, for the treatment and/or prevention of sickle cell anemia or thalassemia. In certain aspects, the invention provides methods for upregulating HBE1, HBG1, and/or HBG2 for treatment and/or prevention of sickle cell anemia. In other aspects, the invention provides methods for upregulating HBB for treatment and/or prevention of beta-thalassemia. In certain aspects, the invention provides methods for upregulating HBD for treatment and/or prevention of delta-thalassemia.

Further aspects of the invention provide methods for selecting oligonucleotides for activating or enhancing expression of a hemoglobin gene, e.g., HBB, HBD, HBE1, HBG1 or HBG2. In some embodiments, methods are provided for selecting a set of oligonucleotides that is enriched in candidates (e.g., compared with a random selection of oligonucleotides) for activating or enhancing expression of a hemoglobin gene, e.g., HBB, HBD, HBE1, HBG1 or HBG2. Accordingly, the methods may be used to establish sets of clinical candidates that are enriched in oligonucleotides that activate or enhance expression of a hemoglobin gene, e.g., HBB, HBD, HBE1, HBG1 or HBG2. Such libraries may be utilized, for example, to identify lead oligonucleotides for developing therapeutics to treat a disease associated with decreased levels of a hemoglobin gene, e.g., HBB, HBD, HBE1, HBG1 or HBG2. Furthermore, in some embodiments, oligonucleotide chemistries are provided that are useful for controlling the pharmacokinetics, biodistribution, bioavailability and/or efficacy of the single stranded oligonucleotides for activating expression of a hemoglobin gene, e.g., HBB, HBD, HBE1, HBG1 or HBG2.

According to some aspects of the invention single stranded oligonucleotides are provided that have a region of complementarity that is complementarty with (e.g., at least 8 consecutive nucleotides of) a PRC2-associated region of a hemoglobin gene, e.g., a PRC2-associated region of the nucleotide sequence set forth as any one of SEQ ID NOS: 1-10. In some embodiments, the oligonucleotide has at least one of the following features: a) a sequence that is 5'X-Y-Z, in which X is any nucleotide and in which X is at the 5' end of the oligonucleotide, Y is a nucleotide sequence of 6 nucleotides in length that is not a human seed sequence of a microRNA, and Z is a nucleotide sequence of 1 to 23 nucleotides in length; b) a sequence that does not comprise three or more consecutive guanosine nucleotides; c) a sequence that has less than a threshold level of sequence identity with every sequence of nucleotides, of equivalent length to the second nucleotide sequence, that are between 50 kilobases upstream of a 5'-end of an off-target gene and 50 kilobases downstream of a 3'-end of the off-target gene; d) a sequence that is complementary to a PRC2-associated region that encodes an RNA that forms a secondary structure comprising at least two single stranded loops; and e) a sequence that has greater than 60% G-C content. In some embodiments, the single stranded oligonucleotide has at least two of features a), b), c), d), and e), each independently selected. In some embodiments, the single stranded oligonucleotide has at least three of features a), b), c), d), and e), each independently selected. In some embodiments, the single stranded oligonucleotide has at least four of features a), b), c), d), and e), each independently selected. In some embodiments, the single stranded oligonucleotide has each of features a), b), c), d), and e). In certain embodiments, the oligonucleotide has the sequence 5'X-Y-Z, in which the oligonucleotide is 8-50 nucleotides in length.

According to some aspects of the invention, single stranded oligonucleotides are provided that have a sequence X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with a PRC2-associated region of a hemoglobin gene, e.g., a PRC2-associated region of the nucleotide sequence set forth as any one of SEQ ID NOS: 1-10. In some aspects of the invention, single stranded oligonucleotides are provided that have a sequence 5'-X-Y-Z, in which X is any nucleotide, Y is a nucleotide sequence of 6 nucleotides in length that is not a seed sequence of a human microRNA, and Z is a nucleotide sequence of 1 to 23 nucleotides in length, in which the single stranded oligonucleotide is complementary with at least 8 consecutive nucleotides of a PRC2-associated region of a hemoglobin gene, e.g., a PRC2-associated region of the nucleotide sequence set forth as any one of SEQ ID NOS: 1-10. In some embodiments, Y is a sequence selected from Table 1. In some embodiments, the PRC2-associated region is a sequence listed in SEQ ID NO: 17 or 18.

In some embodiments, the single stranded oligonucleotide comprises a nucleotide sequence as set forth in any one of SEQ ID NOS: 19 to 3788 or 3797-3916, or a fragment thereof that is at least 8 nucleotides. In some embodiments, the single stranded oligonucleotide comprises a nucleotide sequence as set forth in any one of SEQ ID NOS: 19 to 3788 or 3797-3916, in which the 5' end of the nucleotide sequence provided is the 5' end of the oligonucleotide. In some embodiments, the region of complementarity (e.g., the at least 8 consecutive nucleotides) is also present within the nucleotide sequence set forth as any one of SEQ ID NOS: 11-16.

In some embodiments, the single stranded oligonucleotide comprises a nucleotide sequence as set forth in any one of SEQ ID NOS: 19 to 3788 or 3797-3916. In some embodiments, the oligonucleotide is up to 50 nucleotides in length. In some embodiments, the single stranded oligonucleotide comprises a fragment of at least 8 nucleotides of a nucleotide sequence as set forth in any one of SEQ ID NOS: 19 to 3788 or 3797-3916.

In some embodiments, the at least 8 consecutive nucleotides are also present within the nucleotide sequence set forth as SEQ ID NO: 11, 13, or 15. In some embodiments, the PRC2-associated region is a sequence listed in SEQ ID NO: 17 or 18. In some embodiments, the single stranded oligonucleotide comprises a nucleotide sequence as set forth in any one of SEQ ID NOS: 19-3788, 3820-3821, 3825-3826, or 3850-3916 or a fragment thereof that is at least 8 nucleotides.

In some embodiments, the at least 8 consecutive nucleotides are present within the nucleotide sequence set forth as SEQ ID NO: 12, 14, or 16. In some embodiments, the single stranded oligonucleotide comprises a nucleotide sequence as set forth in any one of SEQ ID NOS: 3797-3819, 3822-3824, or 3827-3849 or a fragment thereof that is at least 8 nucleotides.

In some embodiments, a single stranded oligonucleotide comprises a nucleotide sequence as set forth in Table 3. In some embodiments, the single stranded oligonucleotide comprises a fragment of at least 8 nucleotides of a nucleotide sequence as set forth in Table 3. In some embodiments, a single stranded oligonucleotide consists of a nucleotide sequence as set forth in Table 3.

In some embodiments, the single stranded oligonucleotide does not comprise three or more consecutive guanosine nucleotides. In some embodiments, the single stranded oligonucleotide does not comprise four or more consecutive guanosine nucleotides.

In some embodiments, the single stranded oligonucleotide is 8 to 30 nucleotides in length. In some embodiments, the single stranded oligonucleotide is up to 50 nucleotides in length. In some embodiments, the single stranded oligonucleotide is 8 to 10 nucleotides in length and all but 1, 2, or 3 of the nucleotides of the complementary sequence of the PRC2-associated region are cytosine or guanosine nucleotides.

In some embodiments, the single stranded oligonucleotide is complementary with at least 8 consecutive nucleotides of a PRC2-associated region of a hemoglobin gene, e.g., a PRC2 region of a nucleotide sequence set forth as any one of SEQ ID NOS: 1-10, in which the nucleotide sequence of the single stranded oligonucleotide comprises one or more of a nucleotide sequence selected from the group consisting of (a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx,
(X)XxxxxX, (X)xXXxxx, (X)xXxXxx, (X)xXxxXx,
(X)xXxxxX, (X)xxXXxx, (X)xxXxXx, (X)xxXxxX,
(X)xxxXXx, (X)xxxXxX and (X)xxxxXX, (c) (X)XXXxxx, (X)xXXXxx, (X)xxXXXx,
(X)xxxXXX, (X)XXxXxx, (X)XxxXxX, (X)XXxxxX,
(X)xXXxXx, (X)xXXxxX, (X)xxXXxX, (X)XxXXxx,
(X)XxxXXx (X)XxxxXX, (X)xXxxXx, (X)xXxxxX,
(X)xxXxXX, (X)xXxXxX and (X)XxXxXx, (d) (X)xxXXX, (X)xXxXXX, (X)xXXxXX,
(X)xXXXxX, (X)xXXXXx, (X)XxxXXXX,
(X)XxXxXX, (X)XxXXxX, (X)XxXXXx, (X)XXxxXX,
(X)XXxXxX, (X)XXxXXx, (X)XXXxxX,
(X)XXXxXx, and (X)XXXXxx, (e) (X)xXXXXX, (X)XxXXXX, (X)XXxXXX,
(X)XXXxXX, (X)XXXXxX and (X)XXXXXx, and (f) XXXXXX, XxXXXXX, XXxXXXX, XXXxXXX,
XXXXxXX, XXXXXxX and XXXXXXx, wherein
"X" denotes a nucleotide analogue, (X) denotes an
optional nucleotide analogue, and "x" denotes a DNA
or RNA nucleotide unit.

In some embodiments, at least one nucleotide of the oligonucleotide is a nucleotide analogue. In some embodiments, the at least one nucleotide analogue results in an increase in Tm of the oligonucleotide in a range of 1 to 5° C. compared with an oligonucleotide that does not have the at least one nucleotide analogue.

In some embodiments, at least one nucleotide of the oligonucleotide comprises a 2' O-methyl. In some embodiments, each nucleotide of the oligonucleotide comprises a 2' O-methyl. In some embodiments, the oligonucleotide comprises at least one ribonucleotide, at least one deoxyribonucleotide, or at least one bridged nucleotide. In some embodiments, the bridged nucleotide is a LNA nucleotide, a cEt nucleotide or a ENA modified nucleotide. In some embodiments, each nucleotide of the oligonucleotide is a LNA nucleotide.

In some embodiments, the nucleotides of the oligonucleotide comprise alternating deoxyribonucleotides and 2'-fluoro-deoxyribonucleotides. In some embodiments, the nucleotides of the oligonucleotide comprise alternating deoxyribonucleotides and 2'-O-methyl nucleotides. In some embodiments, the nucleotides of the oligonucleotide comprise alternating deoxyribonucleotides and ENA nucleotide analogues. In some embodiments, the nucleotides of the oligonucleotide comprise alternating deoxyribonucleotides and LNA nucleotides. In some embodiments, the 5' nucleotide of the oligonucleotide is a deoxyribonucleotide. In some embodiments, the nucleotides of the oligonucleotide comprise alternating LNA nucleotides and 2'-O-methyl nucleotides. In some embodiments, the 5' nucleotide of the oligonucleotide is a LNA nucleotide. In some embodiments, the nucleotides of the oligonucleotide comprise deoxyribonucleotides flanked by at least one LNA nucleotide on each of the 5' and 3' ends of the deoxyribonucleotides.

In some embodiments, the single stranded oligonucleotide comprises modified internucleotide linkages (e.g., phosphorothioate internucleotide linkages or other linkages) between at least two, at least three, at least four, at least five or more nucleotides. In some embodiments, the single stranded oligonucleotide comprises modified internucleotide linkages (e.g., phosphorothioate internucleotide linkages or other linkages) between between all nucleotides.

In some embodiments, the nucleotide at the 3' position of the oligonucleotide has a 3' hydroxyl group. In some embodiments, the nucleotide at the 3' position of the oligonucleotide has a 3' thiophosphate. In some embodiments, the single stranded oligonucleotide has a biotin moiety or other moiety conjugated to its 5' or 3' nucleotide. In some embodiments, the single stranded oligonucleotide has cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

According to some aspects of the invention compositions are provided that comprise any of the oligonucleotides disclosed herein, and a carrier. In some embodiments, compositions are provided that comprise any of the oligonucleotides in a buffered solution. In some embodiments, the oligonucleotide is conjugated to the carrier. In some embodiments, the carrier is a peptide. In some embodiments, the carrier is a steroid. According to some aspects of the invention pharmaceutical compositions are provided that comprise any of the oligonucleotides disclosed herein, and a pharmaceutically acceptable carrier.

According to other aspects of the invention, kits are provided that comprise a container housing any of the compositions disclosed herein.

According to some aspects of the invention, methods of increasing expression of HBB, HBD, HBE1, HBG1 or HBG2 in a cell are provided. In some embodiments, the methods involve delivering any one or more of the single stranded oligonucleotides disclosed herein into the cell. In some embodiments, delivery of the single stranded oligonucleotide into the cell results in a level of expression of HBB, HBD, HBE1, HBG1 or HBG2 that is greater (e.g., at least 50% greater) than a level of expression of HBB, HBD, HBE1, HBG1 or HBG2 in a control cell that does not comprise the single stranded oligonucleotide.

According to some aspects of the invention, methods of increasing levels of HBB, HBD, HBE1, HBG1 or HBG2 in a subject are provided. According to some aspects of the invention, methods of treating a condition (e.g., anemia, sickle cell anemia, thalassemia) associated with decreased levels of HBB, HBD, HBE1, HBG1 or HBG2 in a subject are provided. In some embodiments, the methods involve administering any one or more of the single stranded oligonucleotides disclosed herein to the subject.

BRIEF DESCRIPTION OF TABLES

Table 1: Hexamers that are not seed sequences of human miRNAs.

Table 2: A listing of oligonucleotide modifications.

Table 3: Formatted oligonucleotide sequences made for testing showing nucleotide modifications. The table shows the sequence of the modified nucleotides, where lnaX represents an LNA nucleotide with 3' phosphorothioate linkage, omeX is a 2'-O-methyl nucleotide, dX is a deoxy nucleotide. An s at the end of a nucleotide code indicates that the nucleotide had a 3' phosphorothioate linkage. The "-Sup" at the end of the sequence marks the fact that the 3' end lacks either a phosphate or thiophosphate on the 3' linkage. The Formatted Sequence column shows the sequence of the oligonucleotide, including modified nucleotides.

DETAILED DESCRIPTION OF CERTAIN
EMBODIMENTS OF THE INVENTION

Aspects of the invention provided herein relate to the discovery of polycomb repressive complex 2 (PRC2)-interacting RNAs. Polycomb repressive complex 2 (PRC2) is a histone methyltransferase and a known epigenetic regulator involved in silencing of genomic regions through methylation of histone H3. Among other functions, PRC2 interacts with long noncoding RNAs (lncRNAs), such as RepA, Xist, and Tsix, to catalyze trimethylation of histone H3-lysine27. PRC2 contains four subunits, Eed, Suz12, RbAp48, and Ezh2. Aspects of the invention relate to the recognition that single stranded oligonucleotides that bind to PRC2-associated regions of RNAs (e.g., lncRNAs) that are expressed from within a genomic region that encompasses or that is in functional proximity to the HBB, HBD, HBE1, HBG1 or HBG2 gene can induce or enhance expression of HBB, HBD, HBE1, HBG1 or HBG2. In some embodiments, this upregulation is believed to result from inhibition of PRC2 mediated repression of HBB, HBD, HBE1, HBG1 or HBG2.

As used herein, the term "PRC2-associated region" refers to a region of a nucleic acid that comprises or encodes a sequence of nucleotides that interact directly or indirectly with a component of PRC2. A PRC2-associated region may be present in a RNA (e.g., a long non-coding RNA (lncRNA)) that that interacts with a PRC2. A PRC2-associated region may be present in a DNA that encodes an RNA that interacts with PRC2. In some cases, the PRC2-associated region is equivalently referred to as a PRC2-interacting region.

In some embodiments, a PRC2-associated region is a region of an RNA that crosslinks to a component of PRC2 in response to in situ ultraviolet irradiation of a cell that expresses the RNA, or a region of genomic DNA that encodes that RNA region. In some embodiments, a PRC2-associated region is a region of an RNA that immunoprecipitates with an antibody that targets a component of PRC2, or a region of genomic DNA that encodes that RNA region. In some embodiments, a PRC2-associated region is a region of an RNA that immunoprecipitates with an antibody that binds specifically to SUZ12, EED, EZH2 or RBBP4 (which as noted above are components of PRC2), or a region of genomic DNA that encodes that RNA region.

In some embodiments, a PRC2-associated region is a region of an RNA that is protected from nucleases (e.g., RNases) in an RNA-immunoprecipitation assay that employs an antibody that targets a component of PRC2, or a region of genomic DNA that encodes that protected RNA region. In some embodiments, a PRC2-associated region is a region of an RNA that is protected from nucleases (e.g., RNases) in an RNA-immunoprecipitation assay that employs an antibody that targets SUZ12, EED, EZH2 or RBBP4, or a region of genomic DNA that encodes that protected RNA region.

In some embodiments, a PRC2-associated region is a region of an RNA within which occur a relatively high frequency of sequence reads in a sequencing reaction of products of an RNA-immunoprecipitation assay that employs an antibody that targets a component of PRC2, or a region of genomic DNA that encodes that RNA region. In some embodiments, a PRC2-associated region is a region of an RNA within which occur a relatively high frequency of sequence reads in a sequencing reaction of products of an RNA-immunoprecipitation assay that employs an antibody that binds specifically to SUZ12, EED, EZH2 or RBBP4, or a region of genomic DNA that encodes that protected RNA region. In such embodiments, the PRC2-associated region may be referred to as a "peak."

In some embodiments, a PRC2-associated region comprises a sequence of 40 to 60 nucleotides that interact with PRC2 complex. In some embodiments, a PRC2-associated region comprises a sequence of 40 to 60 nucleotides that encode an RNA that interacts with PRC2. In some embodiments, a PRC2-associated region comprises a sequence of up to 5 kb in length that comprises a sequence (e.g., of 40 to 60 nucleotides) that interacts with PRC2. In some embodiments, a PRC2-associated region comprises a sequence of up to 5 kb in length within which an RNA is encoded that has a sequence (e.g., of 40 to 60 nucleotides) that is known to interact with PRC2. In some embodiments, a PRC2-associated region comprises a sequence of about 4 kb in length that comprise a sequence (e.g., of 40 to 60 nucleotides) that interacts with PRC2. In some embodiments, a PRC2-associated region comprises a sequence of about 4 kb in length within which an RNA is encoded that includes a sequence (e.g., of 40 to 60 nucleotides) that is known to interact with PRC2. In some embodiments, a PRC2-associated region has a sequence as set forth in SEQ ID NO: 17 or 18.

In some embodiments, single stranded oligonucleotides are provided that specifically bind to, or are complementary to, a PRC2-associated region in a genomic region that encompasses or that is in proximity to the HBB, HBD, HBE1, HBG1 or HBG2 gene. In some embodiments, single stranded oligonucleotides are provided that specifically bind to, or are complementary to, a PRC2-associated region that has a sequence as set forth in SEQ ID NO: 17 or 18. In some embodiments, single stranded oligonucleotides are provided that specifically bind to, or are complementary to, a PRC2-associated region that has a sequence as set forth in SEQ ID NO: 17 or 18 combined with up to 2 kb, up to 5 kb, or up to 10 kb of flanking sequences from a corresponding genomic region to which these SEQ IDs map (e.g., in a human genome). In some embodiments, single stranded oligonucleotides have a sequence as set forth in any one of SEQ ID NOS: 19 to 3788 or 3797-3916. In some embodiments, a single stranded oligonucleotide has a sequence as set forth in Table 3.

Without being bound by a theory of invention, these oligonucleotides are able to interfere with the binding of and function of PRC2, by preventing recruitment of PRC2 to a specific chromosomal locus. For example, a single administration of single stranded oligonucleotides designed to specifically bind a PRC2-associated region lncRNA can stably displace not only the lncRNA, but also the PRC2 that binds to the lncRNA, from binding chromatin. After displacement, the full complement of PRC2 is not recovered for up to 24 hours. Further, lncRNA can recruit PRC2 in a cis fashion, repressing gene expression at or near the specific chromosomal locus from which the lncRNA was transcribed.

Methods of modulating gene expression are provided, in some embodiments, that may be carried out in vitro, ex vivo, or in vivo. It is understood that any reference to uses of compounds throughout the description contemplates use of the compound in preparation of a pharmaceutical composition or medicament for use in the treatment of condition (e.g., anemia, sickle cell anemia, thalassemia) associated with decreased levels or activity of HBB, HBD, HBE1, HBG1 or HBG2. Thus, as one nonlimiting example, this aspect of the invention includes use of such single stranded oligonucleotides in the preparation of a medicament for use in the treatment of disease, wherein the treatment involves upregulating expression of HBB, HBD, HBE1, HBG1 or HBG2.

In further aspects of the invention, methods are provided for selecting a candidate oligonucleotide for activating expression of HBB, HBD, HBE1, HBG1 or HBG2. The methods generally involve selecting as a candidate oligonucleotide, a single stranded oligonucleotide comprising a nucleotide sequence that is complementary to a PRC2- associated region (e.g., a nucleotide sequence as set forth in SEQ ID NO: 17 or 18). In some embodiments, sets of oligonucleotides may be selected that are enriched (e.g., compared with a random selection of oligonucleotides) in oligonucleotides that activate expression of HBB, HBD, HBE1, HBG1 or HBG2.

Single Stranded Oligonucleotides for Modulating Expression of HBB, HBD, HBE1, HBG1 or HBG2

In one aspect of the invention, single stranded oligonucleotides complementary to the PRC2-associated regions are provided for modulating expression of HBB, HBD, HBE1, HBG1 or HBG2 in a cell. In some embodiments, expression of HBB, HBD, HBE1, HBG1 or HBG2 is upregulated or increased. In some embodiments, single stranded oligonucleotides complementary to these PRC2-associated regions inhibit the interaction of PRC2 with long RNA transcripts such that gene expression is upregulated or increased. In some embodiments, single stranded oligonucleotides complementary to these PRC2-associated regions inhibit the interaction of PRC2 with long RNA transcripts, resulting in reduced methylation of histone H3 and reduced gene inactivation, such that gene expression is upregulated or increased. In some embodiments, this interaction may be disrupted or inhibited due to a change in the structure of the long RNA that prevents or reduces binding to PRC2. The oligonucleotide may be selected using any of the methods disclosed herein for selecting a candidate oligonucleotide for activating expression of HBB, HBD, HBE1, HBG1 or HBG2.

The single stranded oligonucleotide may comprise a region of complementarity that is complementary with a PRC2-associated region of a nucleotide sequence set forth in any one of SEQ ID NOS: 1 to 16. The region of complementarity of the single stranded oligonucleotide may be complementary with at least 6, e.g., at least 7, at least 8, at least 9, at least 10, at least 15 or more consecutive nucleotides of the PRC2-associated region.

The PRC2-associated region may map to a position in a chromosome between 50 kilobases upstream of a 5'-end of the HBB, HBD, HBE1, HBG1 or HBG2 gene and 50 kilobases downstream of a 3'-end of the HBB, HBD, HBE1, HBG1 or HBG2 gene. The PRC2-associated region may map to a position in a chromosome between 25 kilobases upstream of a 5'-end of the HBB, HBD, HBE1, HBG1 or HBG2 gene and 25 kilobases downstream of a 3'-end of the HBB, HBD, HBE1, HBG1 or HBG2 gene. The PRC2-associated region may map to a position in a chromosome between 12 kilobases upstream of a 5'-end of the HBB, HBD, HBE1, HBG1 or HBG2 gene and 12 kilobases downstream of a 3'-end of the HBB, HBD, HBE1, HBG1 or HBG2 gene. The PRC2-associated region may map to a position in a chromosome between 5 kilobases upstream of a 5'-end of the HBB, HBD, HBE1, HBG1 or HBG2 gene and 5 kilobases downstream of a 3'-end of the HBB, HBD, HBE1, HBG1 or HBG2 gene.

The genomic position of the selected PRC2-associated region relative to the HBB, HBD, HBE1, HBG1 or HBG2 gene may vary. For example, the PRC2-associated region may be upstream of the 5' end of the HBB, HBD, HBE1, HBG1 or HBG2 gene. The PRC2-associated region may be downstream of the 3' end of the HBB, HBD, HBE1, HBG1 or HBG2 gene. The PRC2-associated region may be within an intron of the HBB, HBD, HBE1, HBG1 or HBG2 gene. The PRC2-associated region may be within an exon of the HBB, HBD, HBE1, HBG1 or HBG2 gene. The PRC2-associated region may traverse an intron-exon junction, a 5'-UTR-exon junction or a 3'-UTR-exon junction of the HBB, HBD, HBE1, HBG1 or HBG2 gene.

The single stranded oligonucleotide may comprise a sequence having the formula X-Y-Z, in which X is any nucleotide, Y is a nucleotide sequence of 6 nucleotides in length that is not a human seed sequence of a microRNA, and Z is a nucleotide sequence of varying length. In some embodiments X is the 5' nucleotide of the oligonucleotide. In some embodiments, when X is anchored at the 5' end of the oligonucleotide, the oligonucleotide does not have any nucleotides or nucleotide analogs linked 5' to X. In some embodiments, other compounds such as peptides or sterols may be linked at the 5' end in this embodiment as long as they are not nucleotides or nucleotide analogs. In some embodiments, the single stranded oligonucleotide has a sequence 5'X-Y-Z and is 8-50 nucleotides in length. Oligonucleotides that have these sequence characteristics are predicted to avoid the miRNA pathway. Therefore, in some embodiments, oligonucleotides having these sequence characteristics are unlikely to have an unintended consequence of functioning in a cell as a miRNA molecule. The Y sequence may be a nucleotide sequence of 6 nucleotides in length set forth in Table 1.

The single stranded oligonucleotide may have a sequence that does not contain guanosine nucleotide stretches (e.g., 3 or more, 4 or more, 5 or more, 6 or more consecutive guanosine nucleotides). In some embodiments, oligonucleotides having guanosine nucleotide stretches have increased non-specific binding and/or off-target effects, compared with oligonucleotides that do not have guanosine nucleotide stretches.

The single stranded oligonucleotide may have a sequence that has less than a threshold level of sequence identity with every sequence of nucleotides, of equivalent length, that map to a genomic position encompassing or in proximity to an off-target gene. For example, an oligonucleotide may be designed to ensure that it does not have a sequence that maps to genomic positions encompassing or in proximity with all known genes (e.g., all known protein coding genes) other than HBB, HBD, HBE1, HBG1 or HBG2. In a similar embodiment, an oligonucleotide may be designed to ensure that it does not have a sequence that maps to any other known PRC2-associated region, particularly PRC2-associated regions that are functionally related to any other known gene (e.g., any other known protein coding gene). In either case, the oligonucleotide is expected to have a reduced likelihood of having off-target effects. The threshold level of sequence identity may be 50%, 60%, 70%, 80%, 85%, 90%, 95%, 99% or 100% sequence identity.

The single stranded oligonucleotide may have a sequence that is complementary to a PRC2-associated region that encodes an RNA that forms a secondary structure comprising at least two single stranded loops. In has been discovered that, in some embodiments, oligonucleotides that are complementary to a PRC2-associated region that encodes an RNA that forms a secondary structure comprising one or more single stranded loops (e.g., at least two single stranded loops) have a greater likelihood of being active (e.g., of being capable of activating or enhancing expression of a target gene) than a randomly selected oligonucleotide. In some cases, the secondary structure may comprise a double stranded stem between the at least two single stranded loops. Accordingly, the region of complementarity between the oligonucleotide and the PRC2-associated region may be at a location of the PRC2 associated region that encodes at least a portion of at least one of the loops. In some cases, the region of complementarity between the oligonucleotide and the PRC2-associated region may be at a location of the PRC2-associated region that encodes at least a portion of at least two of the loops. In some cases, the region of complementarity between the oligonucleotide and the PRC2-associated region may be at a location of the PRC2 associated region that encodes at least a portion of the double stranded stem. In some embodiments, a PRC2-associated region (e.g., of an lncRNA) is identified (e.g., using RIP-Seq methodology or information derived therefrom). In some embodiments, the predicted secondary structure RNA (e.g., lncRNA) containing the PRC2-associated region is determined using RNA secondary structure prediction algorithms, e.g., RNAfold, mfold. In some embodiments, oligonucleotides are designed to target a region of the RNA that forms a secondary structure comprising one or more single stranded loop (e.g., at least two single stranded loops) structures which may comprise a double stranded stem between the at least two single stranded loops.

The single stranded oligonucleotide may have a sequence that is has greater than 30% G-C content, greater than 40% G-C content, greater than 50% G-C content, greater than 60% G-C content, greater than 70% G-C content, or greater than 80% G-C content. The single stranded oligonucleotide may have a sequence that has up to 100% G-C content, up to 95% G-C content, up to 90% G-C content, or up to 80% G-C content. In some embodiments in which the oligonucleotide is 8 to 10 nucleotides in length, all but 1, 2, 3, 4, or 5 of the nucleotides of the complementary sequence of the PRC2-associated region are cytosine or guanosine nucleotides. In some embodiments, the sequence of the PRC2-associated region to which the single stranded oligonucleotide is complementary comprises no more than 3 nucleotides selected from adenine and uracil.

The single stranded oligonucleotide may be complementary to a chromosome of a different species (e.g., a mouse, rat, rabbit, goat, monkey, etc.) at a position that encompasses or that is in proximity to that species' homolog of HBB, HBD, HBE1, HBG1 or HBG2. The single stranded oligonucleotide may be complementary to a human genomic region encompassing or in proximity to the HBB, HBD, HBE1, HBG1 or HBG2 gene and also be complementary to a mouse genomic region encompassing or in proximity to the mouse homolog of HBB, HBD, HBE1, HBG1 or HBG2. For example, the single stranded oligonucleotide may be complementary to a sequence as set forth as any one of SEQ ID NOS: 1-10, which is a human genomic region encompassing or in proximity to the HBB, HBD, HBE1, HBG1 or HBG2 gene, and also be complementary to a sequence as set forth in any one of SEQ ID NOS: 1-10, which is a mouse genomic region encompassing or in proximity to the mouse homolog of the HBB, HBD, HBE1, HBG1 or HBG2 gene. Oligonucleotides having these characteristics may be tested in vivo or in vitro for efficacy in multiple species (e.g., human and mouse). This approach also facilitates development of clinical candidates for treating human disease by selecting a species in which an appropriate animal exists for the disease.

In some embodiments, the region of complementarity of the single stranded oligonucleotide is complementary with at least 8 to 15, 8 to 30, 8 to 40, or 10 to 50, or 5 to 50, or 5 to 40 bases, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of a PRC2-associated region. In some embodiments, the region of complementarity is complementary with at least 8 consecutive nucleotides of a PRC2-associated region. In some embodiments the sequence of the single stranded oligonucleotide is based on an RNA sequence that binds to PRC2, or a portion thereof, said portion having a length of from 5 to 40 contiguous base pairs, or about 8 to 40 bases, or about 5 to 15, or about 5 to 30, or about 5 to 40 bases, or about 5 to 50 bases.

Complementary, as the term is used in the art, refers to the capacity for precise pairing between two nucleotides. For example, if a nucleotide at a certain position of an oligonucleotide is capable of hydrogen bonding with a nucleotide at the same position of PRC2-associated region, then the single stranded nucleotide and PRC2-associated region are considered to be complementary to each other at that position. The single stranded nucleotide and PRC2-associated region are complementary to each other when a sufficient number of corresponding positions in each molecule are occupied by nucleotides that can hydrogen bond with each other through their bases. Thus, "complementary" is a term which is used to indicate a sufficient degree of complementarity or precise pairing such that stable and specific binding occurs between the single stranded nucleotide and PRC2-associated region. For example, if a base at one position of a single stranded nucleotide is capable of hydrogen bonding with a base at the corresponding position of a PRC2-associated region, then the bases are considered to be complementary to each other at that position. 100% complementarity is not required.

The single stranded oligonucleotide may be at least 80% complementary to (optionally one of at least 85%, 90%, 91%, 92%, 93%, 94%, 95%, 96%, 97%, 98%, 99% or 100% complementary to) the consecutive nucleotides of a PRC2-associated region. In some embodiments the single stranded oligonucleotide may contain 1, 2 or 3 base mismatches compared to the portion of the consecutive nucleotides of a PRC2-associated region. In some embodiments the single stranded oligonucleotide may have up to 3 mismatches over 15 bases, or up to 2 mismatches over 10 bases.

It is understood in the art that a complementary nucleotide sequence need not be 100% complementary to that of its target to be specifically hybridizable. In some embodiments, a complementary nucleic acid sequence for purposes of the present disclosure is specifically hybridizable when binding of the sequence to the target molecule (e.g., lncRNA) interferes with the normal function of the target (e.g., lncRNA) to cause a loss of activity (e.g., inhibiting PRC2-associated repression with consequent up-regulation of gene expression) and there is a sufficient degree of complementarity to avoid non-specific binding of the sequence to non-target sequences under conditions in which avoidance of non-specific binding is desired, e.g., under physiological conditions in the case of in vivo assays or therapeutic treatment, and in the case of in vitro assays, under conditions in which the assays are performed under suitable conditions of stringency.

In some embodiments, the single stranded oligonucleotide is 7, 8, 9, 10, 11, 12, 13, 14, 15, 16, 17, 18, 19, 20, 21, 22, 23, 24, 25, 26, 27, 28, 29, 30, 35, 40, 45, 50 or more nucleotides in length. In a preferred embodiment, the oligonucleotide is 8 to 30 nucleotides in length.

In some embodiments, the PRC2-associated region occurs on the same DNA strand as a gene sequence (sense). In some embodiments, the PRC2-associated region occurs on the opposite DNA strand as a gene sequence (anti-sense). Oligonucleotides complementary to a PRC2-associated region can bind either sense or anti-sense sequences. Base pairings may include both canonical Watson-Crick base pairing and non-Watson-Crick base pairing (e.g., Wobble base pairing and Hoogsteen base pairing). It is understood that for complementary base pairings, adenosine-type bases (A) are complementary to thymidine-type bases (T) or uracil-type bases (U), that cytosine-type bases (C) are complementary to guanosine-type bases (G), and that universal bases such as 3-nitropyrrole or 5-nitroindole can hybridize to and are considered complementary to any A, C, U, or T. Inosine (I) has also been considered in the art to be a universal base and is considered complementary to any A, C, U or T.

In some embodiments, any one or more thymidine (T) nucleotides (or modified nucleotide thereof) or uridine (U) nucleotides (or a modified nucleotide thereof) in a sequence provided herein, including a sequence provided in the sequence listing, may be replaced with any other nucleotide suitable for base pairing (e.g., via a Watson-Crick base pair) with an adenosine nucleotide. In some embodiments, any one or more thymidine (T) nucleotides (or modified nucleotide thereof) or uridine (U) nucleotides (or a modified nucleotide thereof) in a sequence provided herein, including a sequence provided in the sequence listing, may be suitably replaced with a different pyrimidine nucleotide or vice versa. In some embodiments, any one or more thymidine (T) nucleotides (or modified nucleotide thereof) in a sequence provided herein, including a sequence provided in the sequence listing, may be suitably replaced with a uridine (U) nucleotide (or a modified nucleotide thereof) or vice versa.

In some embodiments, GC content of the single stranded oligonucleotide is preferably between about 30-60%. Contiguous runs of three or more Gs or Cs may not be preferable in some embodiments. Accordingly, in some embodiments, the oligonucleotide does not comprise a stretch of three or more guanosine nucleotides.

In some embodiments, the single stranded oligonucleotide specifically binds to, or is complementary to an RNA that is encoded in a genome (e.g., a human genome) as a single contiguous transcript (e.g., a non-spliced RNA). In some embodiments, the single stranded oligonucleotide specifically binds to, or is complementary to an RNA that is encoded in a genome (e.g., a human genome), in which the distance in the genome between the 5' end of the coding region of the RNA and the 3' end of the coding region of the RNA is less than 1 kb, less than 2 kb, less than 3 kb, less than 4 kb, less than 5 kb, less than 7 kb, less than 8 kb, less than 9 kb, less than 10 kb, or less than 20 kb.

It is to be understood that any oligonucleotide provided herein can be excluded. In some embodiments, a single stranded oligonucleotide is not complementary to SEQ ID NO: 3917.

In some embodiments, it has been found that single stranded oligonucleotides disclosed herein may increase expression of mRNA corresponding to the gene by at least about 50% (i.e. 150% of normal or 1.5 fold), or by about 2 fold to about 5 fold. In some embodiments, expression may be increased by at least about 15 fold, 20 fold, 30 fold, 40 fold, 50 fold or 100 fold, or any range between any of the foregoing numbers. It has also been found that increased mRNA expression has been shown to correlate to increased protein expression.

In some or any of the embodiments of the oligonucleotides described herein, or processes for designing or synthesizing them, the oligonucleotides will upregulate gene expression and may specifically bind or specifically hybridize or be complementary to the PRC2 binding RNA that is transcribed from the same strand as a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding sense strand of a reference gene (refGene).

In some or any of the embodiments of oligonucleotides described herein, or processes for designing or synthesizing them, the oligonucleotides will upregulate gene expression and may specifically bind or specifically hybridize or be complementary to a PRC2 binding RNA that transcribed from the opposite strand (the antisense strand) of a protein coding reference gene. The oligonucleotide may bind to a region of the PRC2 binding RNA that originates within or overlaps an intron, exon, intron exon junction, 5' UTR, 3' UTR, a translation initiation region, or a translation termination region of a protein coding antisense strand of a reference gene The oligonucleotides described herein may be modified, e.g., comprise a modified sugar moiety, a modified internucleoside linkage, a modified nucleotide and/or combinations thereof. In addition, the oligonucleotides can exhibit one or more of the following properties: do not induce substantial cleavage or degradation of the target RNA; do not cause substantially complete cleavage or degradation of the target RNA; do not activate the RNAse H pathway; do not activate RISC; do not recruit any Argonaute family protein; are not cleaved by Dicer; do not mediate alternative splicing; are not immune stimulatory; are nuclease resistant; have improved cell uptake compared to unmodified oligonucleotides; are not toxic to cells or mammals; may have improved endosomal exit; do interfere with interaction of lncRNA with PRC2, preferably the Ezh2 subunit but optionally the Suz12, Eed, RbAp46/48 subunits or accessory factors such as Jarid2; do decrease histone H3 lysine27 methylation and/or do upregulate gene expression.

Oligonucleotides that are designed to interact with RNA to modulate gene expression are a distinct subset of base sequences from those that are designed to bind a DNA target (e.g., are complementary to the underlying genomic DNA sequence from which the RNA is transcribed).

Any of the oligonucleotides disclosed herein may be linked to one or more other oligonucleotides disclosed herein by a linker, e.g., a cleavable linker.

Method for Selecting Candidate Oligonucleotides for Activating Expression of Hemoglobin Genes Methods are provided herein for selecting a candidate oligonucleotide for activating or enhancing expression of HBB, HBD, HBE1, HBG1 or HBG2. The target selection methods may generally involve steps for selecting single stranded oligonucleotides having any of the structural and functional characteristics disclosed herein. Typically, the methods involve one or more steps aimed at identifying oligonucleotides that target a PRC2-associated region that is functionally related to HBB, HBD, HBE1, HBG1 or HBG2, for example a PRC2-associated region of a lncRNA that regulates expression of HBB, HBD, HBE1, HBG1 or HBG2 by facilitating (e.g., in a cis-regulatory manner) the recruitment of PRC2 to the HBB, HBD, HBE1, HBG1 or HBG2 gene. Such oligonucleotides are expected to be candidates for activating expression of HBB, HBD, HBE1, HBG1 or HBG2 because of their ability to hybridize with the PRC2-associated region of a nucleic acid (e.g., a lncRNA). This hybridization event is likely to disrupt interaction of PRC2 with the nucleic acid (e.g., a lncRNA) and as a result disrupt recruitment of PRC2 and its associated co-repressors (e.g., chromatin remodeling factors) to the HBB, HBD, HBE1, HBG1 or HBG2 gene locus.

Methods of selecting a candidate oligonucleotide may involve selecting a PRC2-associated region (e.g., a nucleotide sequence as set forth in SEQ ID NO: 17 or 18) that maps to a chromosomal position encompassing or in proximity to the HBB, HBD, HBE1, HBG1 or HBG2 gene (e.g., a chromosomal position having a sequence as set forth in any one of SEQ ID NOS: 1 to 16). The PRC2-associated region may map to the strand of the chromosome comprising the sense strand of the HBB, HBD, HBE1, HBG1 or HBG2 gene, in which case the candidate oligonucleotide is complementary to the sense strand of the HBB, HBD, HBE1, HBG1 or HBG2 gene (i.e., is antisense to the HBB, HBD, HBE1, HBG1 or HBG2 gene). Alternatively, the PRC2-associated region may map to the strand of the first chromosome comprising the antisense strand of the HBB, HBD, HBE1, HBG1 or HBG2 gene, in which case the oligonucleotide is complementary to the antisense strand (the template strand) of the HBB, HBD, HBE1, HBG1 or HBG2 gene (i.e., is sense to the HBB, HBD, HBE1, HBG1 or HBG2 gene).

Methods for selecting a set of candidate oligonucleotides that is enriched in oligonucleotides that activate expression of HBB, HBD, HBE1, HBG1 or HBG2 may involve selecting one or more PRC2-associated regions that map to a chromosomal position that encompasses or that is in proximity to the HBB, HBD, HBE1, HBG1 or HBG2 gene and selecting a set of oligonucleotides, in which each oligonucleotide in the set comprises a nucleotide sequence that is complementary with the one or more PRC2-associated regions. As used herein, the phrase, "a set of oligonucleotides that is enriched in oligonucleotides that activate expression of" refers to a set of oligonucleotides that has a greater number of oligonucleotides that activate expression of a target gene (e.g., HBB, HBD, HBE1, HBG1 or HBG2) compared with a random selection of oligonucleotides of the same physicochemical properties (e.g., the same GC content, $T_m$, length etc.) as the enriched set.

Where the design and/or synthesis of a single stranded oligonucleotide involves design and/or synthesis of a sequence that is complementary to a nucleic acid or PRC2-associated region described by such sequence information, the skilled person is readily able to determine the complementary sequence, e.g., through understanding of Watson Crick base pairing rules which form part of the common general knowledge in the field.

In some embodiments design and/or synthesis of a single stranded oligonucleotide involves manufacture of an oligonucleotide from starting materials by techniques known to those of skill in the art, where the synthesis may be based on a sequence of a PRC2-associated region, or portion thereof.

Methods of design and/or synthesis of a single stranded oligonucleotide may involve one or more of the steps of:

Identifying and/or selecting PRC2-associated region;

Designing a nucleic acid sequence having a desired degree of sequence identity or complementarity to a PRC2-associated region or a portion thereof;

Synthesizing a single stranded oligonucleotide to the designed sequence;

Purifying the synthesized single stranded oligonucleotide; and

Optionally mixing the synthesized single stranded oligonucleotide with at least one pharmaceutically acceptable diluent, carrier or excipient to form a pharmaceutical composition or medicament.

Single stranded oligonucleotides so designed and/or synthesized may be useful in method of modulating gene expression as described herein.

Preferably, single stranded oligonucleotides of the invention are synthesized chemically. Oligonucleotides used to practice this invention can be synthesized in vitro by well-known chemical synthesis techniques.

Oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O—NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

It is understood that any of the modified chemistries or formats of single stranded oligonucleotides described herein can be combined with each other, and that one, two, three, four, five, or more different types of modifications can be included within the same molecule.

In some embodiments, the method may further comprise the steps of amplifying the synthesized single stranded oligonucleotide, and/or purifying the single stranded oligonucleotide (or amplified single stranded oligonucleotide), and/or sequencing the single stranded oligonucleotide so obtained.

As such, the process of preparing a single stranded oligonucleotide may be a process that is for use in the manufacture of a pharmaceutical composition or medicament for use in the treatment of disease, optionally wherein the treatment involves modulating expression of a gene associated with a PRC2-associated region.

In the methods described above a PRC2-associated region may be, or have been, identified, or obtained, by a method that involves identifying RNA that binds to PRC2.

Such methods may involve the following steps: providing a sample containing nuclear ribonucleic acids, contacting the sample with an agent that binds specifically to PRC2 or a subunit thereof, allowing complexes to form between the agent and protein in the sample, partitioning the complexes, synthesizing nucleic acid that is complementary to nucleic acid present in the complexes.

Where the single stranded oligonucleotide is based on a PRC2-associated region, or a portion of such a sequence, it may be based on information about that sequence, e.g., sequence information available in written or electronic form, which may include sequence information contained in publicly available scientific publications or sequence databases.

Nucleotide Analogues

In some embodiments, the oligonucleotide may comprise at least one ribonucleotide, at least one deoxyribonucleotide, and/or at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States patent or patent application Publications: U.S. Pat. Nos. 7,399,845, 7,741,457, 8,022,193, 7,569,686, 7,335,765, 7,314,923, 7,335,765, and U.S. Pat. Nos. 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Often the single stranded oligonucleotide has one or more nucleotide analogues. For example, the single stranded oligonucleotide may have at least one nucleotide analogue that results in an increase in $T_m$ of the oligonucleotide in a range of 1° C., 2° C., 3° C., 4° C., or 5° C. compared with an oligonucleotide that does not have the at least one nucleotide analogue. The single stranded oligonucleotide may have a plurality of nucleotide analogues that results in a total increase in $T_m$ of the oligonucleotide in a range of 2° C., 3° C., 4° C., 5° C., 6° C., 7° C., 8° C., 9° C., 10° C., 15° C., 20° C., 25° C., 30° C., 35° C., 40° C., 45° C. or more compared with an oligonucleotide that does not have the nucleotide analogue.

The oligonucleotide may be of up to 50 nucleotides in length in which 2 to 10, 2 to 15, 2 to 16, 2 to 17, 2 to 18, 2 to 19, 2 to 20, 2 to 25, 2 to 30, 2 to 40, 2 to 45, or more nucleotides of the oligonucleotide are nucleotide analogues. The oligonucleotide may be of 8 to 30 nucleotides in length in which 2 to 10, 2 to 15, 2 to 16, 2 to 17, 2 to 18, 2 to 19, 2 to 20, 2 to 25, 2 to 30 nucleotides of the oligonucleotide are nucleotide analogues.

The oligonucleotide may be of 8 to 15 nucleotides in length in which 2 to 4, 2 to 5, 2 to 6, 2 to 7, 2 to 8, 2 to 9, 2 to 10, 2 to 11, 2 to 12, 2 to 13, 2 to 14 nucleotides of the oligonucleotide are nucleotide analogues. Optionally, the oligonucleotides may have every nucleotide except 1, 2, 3, 4, 5, 6, 7, 8, 9, or 10 nucleotides modified.

The oligonucleotide may consist entirely of bridged nucleotides (e.g., LNA nucleotides, cEt nucleotides, ENA nucleotides). The oligonucleotide may comprise alternating deoxyribonucleotides and 2'-fluoro-deoxyribonucleotides. The oligonucleotide may comprise alternating deoxyribonucleotides and 2'-O-methyl nucleotides. The oligonucleotide may comprise alternating deoxyribonucleotides and ENA nucleotide analogues. The oligonucleotide may comprise alternating deoxyribonucleotides and LNA nucleotides. The oligonucleotide may comprise alternating LNA nucleotides and 2'-O-methyl nucleotides. The oligonucleotide may have a 5' nucleotide that is a bridged nucleotide (e.g., a LNA nucleotide, cEt nucleotide, ENA nucleotide). The oligonucleotide may have a 5' nucleotide that is a deoxyribonucleotide.

The oligonucleotide may comprise deoxyribonucleotides flanked by at least one bridged nucleotide (e.g., a LNA nucleotide, cEt nucleotide, ENA nucleotide) on each of the 5' and 3' ends of the deoxyribonucleotides. The oligonucleotide may comprise deoxyribonucleotides flanked by 1, 2, 3, 4, 5, 6, 7, 8 or more bridged nucleotides (e.g., LNA nucleotides, cEt nucleotides, ENA nucleotides) on each of the 5' and 3' ends of the deoxyribonucleotides. The 3' position of the oligonucleotide may have a 3' hydroxyl group. The 3' position of the oligonucleotide may have a 3' thiophosphate.

The oligonucleotide may be conjugated with a label. For example, the oligonucleotide may be conjugated with a biotin moiety, cholesterol, Vitamin A, folate, sigma receptor ligands, aptamers, peptides, such as CPP, hydrophobic molecules, such as lipids, ASGPR or dynamic polyconjugates and variants thereof at its 5' or 3' end.

Preferably the single stranded oligonucleotide comprises one or more modifications comprising: a modified sugar moiety, and/or a modified internucleoside linkage, and/or a modified nucleotide and/or combinations thereof. It is not necessary for all positions in a given oligonucleotide to be uniformly modified, and in fact more than one of the modifications described herein may be incorporated in a single oligonucleotide or even at within a single nucleoside within an oligonucleotide.

In some embodiments, the single stranded oligonucleotides are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric single stranded oligonucleotides of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In some embodiments, the single stranded oligonucleotide comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —N($CH_3$)—O—$CH_2$ (known as a methylene(methylimino) or MMI backbone, $CH_2$—O—N($CH_3$)—$CH_2$, $CH_2$—N($CH_3$)—N($CH_3$)—$CH_2$ and O—N($CH_3$)— $CH_2$—$CH_2$ backbones, wherein the native phosphodiester backbone is represented as O—P—O—$CH$,); amide backbones (see De Mesmaeker et al. Ace. Chem. Res. 1995, 28:366-374); morpholino backbone structures (see Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, see Nielsen et al., Science 1991, 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'alkylene phosphonates and chiral phosphonates, phosphinates, phosphoramidates comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455, 233; 5,466,677; 5,476,925; 5,519,126; 5,536,821; 5,541,306; 5,550,111; 5,563, 253; 5,571,799; 5,587,361; and 5,625,050.

Morpholino-based oligomeric compounds are described in Dwaine A. Braasch and David R. Corey, Biochemistry, 2002, 41(14), 4503-4510); Genesis, volume 30, issue 3, 2001; Heasman, J., Dev. Biol., 2002, 243, 209-214; Nasevicius et al., Nat. Genet., 2000, 26, 216-220; Lacerra et al., Proc. Natl. Acad. Sci., 2000, 97, 9591-9596; and U.S. Pat. No. 5,034,506, issued Jul. 23, 1991. In some embodiments, the morpholino-based oligomeric compound is a phosphorodiamidate morpholino oligomer (PMO) (e.g., as described in Iverson, Curr. Opin. Mol. Ther., 3:235-238, 2001; and Wang et al., J. Gene Med., 12:354-364, 2010; the disclosures of which are incorporated herein by reference in their entireties).

Cyclohexenyl nucleic acid oligonucleotide mimetics are described in Wang et al., J. Am. Chem. Soc., 2000, 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

Modified oligonucleotides are also known that include oligonucleotides that are based on or constructed from arabinonucleotide or modified arabinonucleotide residues. Arabinonucleosides are stereoisomers of ribonucleosides, differing only in the configuration at the 2'-position of the sugar ring. In some embodiments, a 2'-arabino modification is 2'-F arabino. In some embodiments, the modified oligonucleotide is 2'-fluoro-D-arabinonucleic acid (FANA) (as described in, for example, Lon et al., Biochem., 41:3457-3467, 2002 and Min et al., Bioorg. Med. Chem. Lett., 12:2651-2654, 2002; the disclosures of which are incorporated herein by reference in their entireties). Similar modifications can also be made at other positions on the sugar, particularly the 3' position of the sugar on a 3' terminal nucleoside or in 2'-5' linked oligonucleotides and the 5' position of 5' terminal nucleotide.

PCT Publication No. WO 99/67378 discloses arabinonucleic acids (ANA) oligomers and their analogues for improved sequence specific inhibition of gene expression via association to complementary messenger RNA.

Other preferred modifications include ethylene-bridged nucleic acids (ENAs) (e.g., International Patent Publication No. WO 2005/042777, Morita et al., Nucleic Acid Res., Suppl 1:241-242, 2001; Surono et al., Hum. Gene Ther., 15:749-757, 2004; Koizumi, Curr. Opin. Mol. Ther., 8:144-149, 2006 and Horie et al., Nucleic Acids Symp. Ser (Oxf), 49:171-172, 2005; the disclosures of which are incorporated herein by reference in their entireties). Preferred ENAs include, but are not limited to, 2'-0,4'-C-ethylene-bridged nucleic acids.

Examples of LNAs are described in WO/2008/043753 and include compounds of the following general formula.

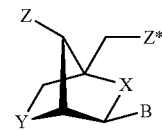

where X and Y are independently selected among the groups —O—,
—S—, —N(H)—, N(R)—, —CH$_2$— or —CH— (if part of a double bond),
—CH$_2$—O—, —CH$_2$—S—, —CH$_2$—N(H)—, —CH$_2$—N(R)—, —CH$_2$—CH$_2$— or —CH$_2$—CH— (if part of a double bond),
—CH=CH—, where R is selected from hydrogen and C$_{1-4}$-alkyl; Z and Z* are independently selected among an internucleoside linkage, a terminal group or a protecting group; B constitutes a natural or non-natural nucleotide base moiety; and the asymmetric groups may be found in either orientation.

Preferably, the LNA used in the oligonucleotides described herein comprises at least one LNA unit according any of the formulas

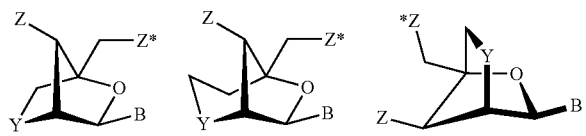

wherein Y is —O—, —S—, —NH—, or N(R$^H$); Z and Z* are independently selected among an internucleoside linkage, a terminal group or a protecting group; B constitutes a natural or non-natural nucleotide base moiety, and RH is selected from hydrogen and C$_{1-4}$-alkyl.

In some embodiments, the Locked Nucleic Acid (LNA) used in the oligonucleotides described herein comprises at least one Locked Nucleic Acid (LNA) unit according any of the formulas shown in Scheme 2 of PCT/DK2006/000512.

In some embodiments, the LNA used in the oligomer of the invention comprises internucleoside linkages selected from -0-P(O)$_2$—O—, —O—P(O,S)—O—, -0-P(S)$_2$—O—, —S—P(O)$_2$—O—, —S—P(O,S)—O—, —S—P(S)$_2$—O—, -0-P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—OC—O—, where R$^H$ is selected from hydrogen and C$_{1-4}$-alkyl.

Specifically preferred LNA units are shown in scheme 2:

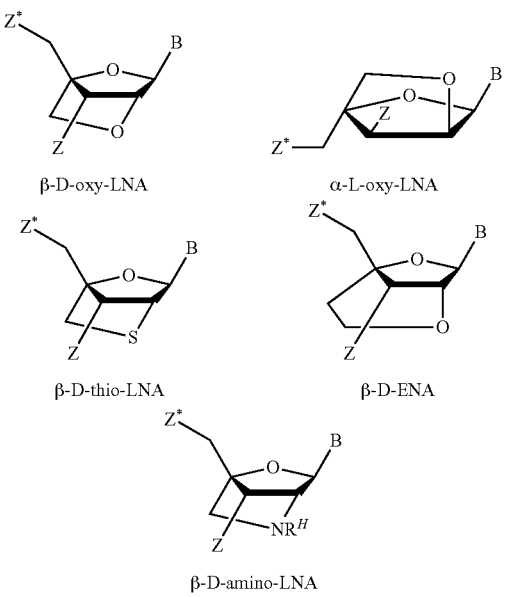

Scheme 2

β-D-oxy-LNA   α-L-oxy-LNA

β-D-thio-LNA   β-D-ENA

β-D-amino-LNA

The term "thio-LNA" comprises a locked nucleotide in which at least one of X or Y in the general formula above is selected from S or —CH$_2$—S—. Thio-LNA can be in both beta-D and alpha-L-configuration.

The term "amino-LNA" comprises a locked nucleotide in which at least one of X or Y in the general formula above is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleotide in which at least one of X or Y in the general formula above represents —O— or —CH$_2$—O—. Oxy-LNA can be in both beta-D and alpha-L-configuration.

The term "ena-LNA" comprises a locked nucleotide in which Y in the general formula above is —CH$_2$—O— (where the oxygen atom of —CH$_2$—O— is attached to the 2'-position relative to the base B).

LNAs are described in additional detail herein.

One or more substituted sugar moieties can also be included, e.g., one of the following at the 2' position: OH, SH, SCH$_3$, F, OCN, OCH$_3$ OCH$_3$, OCH$_3$O(CH$_2$)n CH$_3$, O(CH$_2$)n NH$_2$ or O(CH$_2$)n CH$_3$ where n is from 1 to about 10; C1 to C10 lower alkyl, alkoxyalkoxy, substituted lower alkyl, alkaryl or aralkyl; Cl; Br; CN; CF$_3$; OCF$_3$; O—, S—, or N-alkyl; O—, S—, or N-alkenyl; SOCH$_3$; SO$_2$CH$_3$; ONO$_2$; NO$_2$, N$_3$; NH2; heterocycloalkyl; heterocycloalkaryl; amino alkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin et al, Helv. Chim. Acta, 1995, 78, 486). Other preferred modifications include 2'-methoxy (2'-O—CH$_3$), 2'-propoxy (2'-OCH$_2$CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Single stranded oligonucleotides can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, isocytosine, pseudoisocytosine, as well as synthetic nucleobases, e.g., 2-aminoadenine, 2-(methylamino)adenine, 2-(imidazolylalkyl)adenine, 2-(aminoalkylamino) adenine or other heterosubstituted alkyladenines, 2-thiouracil, 2-thiothymine, 5-bromouracil, 5-hydroxymethyluracil, 5-propynyluracil, 8-azaguanine, 7-deazaguanine, N6 (6-aminohexyl)adenine, 6-aminopurine, 2-aminopurine, 2-chloro-6-aminopurine and 2,6-diaminopurine or other diaminopurines. See, e.g., Kornberg, "DNA Replication," W. H. Freeman & Co., San Francisco, 1980, pp 75-77; and Gebeyehu, G., et al. Nucl. Acids Res., 15:4513 (1987)). A "universal" base known in the art, e.g., inosine, can also be included. 5-Me-C substitutions have been shown to increase nucleic acid duplex stability by 0.6-1.2° C. (Sanghvi, in Crooke, and Lebleu, eds., Antisense Research and Applications, CRC Press, Boca Raton, 1993, pp. 276-278) and may be used as base substitutions.

It is not necessary for all positions in a given oligonucleotide to be uniformly modified, and in fact more than one of the modifications described herein may be incorporated in a single oligonucleotide or even at within a single nucleoside within an oligonucleotide.

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al, Science, 1991, 254, 1497-1500.

Single stranded oligonucleotides can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in "The Concise Encyclopedia of Polymer Science And Engineering", pages 858-859, Kroschwitz, ed. John Wiley & Sons, 1990; those disclosed by Englisch et al., Angewandle Chemie, International Edition, 1991, 30, page 613, and those disclosed by Sanghvi, Chapter 15, Antisense Research and Applications," pages 289-302, Crooke, and Lebleu, eds., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, et al., eds, "Antisense Research and Applications," CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

In some embodiments, the single stranded oligonucleotides are chemically linked to one or more moieties or conjugates that enhance the activity, cellular distribution, or cellular uptake of the oligonucleotide. For example, one or more single stranded oligonucleotides, of the same or different types, can be conjugated to each other; or single stranded oligonucleotides can be conjugated to targeting moieties with enhanced specificity for a cell type or tissue type. Such moieties include, but are not limited to, lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al, Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Mancharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-t oxycholesterol moiety (Crooke et al., J. Pharmacol. Exp. Ther., 1996, 277, 923-937). See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

In some embodiments, single stranded oligonucleotide modification include modification of the 5' or 3' end of the oligonucleotide. In some embodiments, the 3' end of the oligonucleotide comprises a hydroxyl group or a thiophosphate. It should be appreciated that additional molecules (e.g. a biotin moiety or a fluorophor) can be conjugated to the 5' or 3' end of the single stranded oligonucleotide. In some embodiments, the single stranded oligonucleotide comprises a biotin moiety conjugated to the 5' nucleotide.

In some embodiments, the single stranded oligonucleotide comprises locked nucleic acids (LNA), ENA modified nucleotides, 2'-O-methyl nucleotides, or 2'-fluoro-deoxyribonucleotides. In some embodiments, the single stranded oligonucleotide comprises alternating deoxyribonucleotides and 2'-fluoro-deoxyribonucleotides. In some embodiments, the single stranded oligonucleotide comprises alternating deoxyribonucleotides and 2'-O-methyl nucleotides. In some embodiments, the single stranded oligonucleotide comprises alternating deoxyribonucleotides and ENA modified nucleotides. In some embodiments, the single stranded oligonucleotide comprises alternating deoxyribonucleotides and locked nucleic acid nucleotides. In some embodiments, the single stranded oligonucleotide comprises alternating locked nucleic acid nucleotides and 2'-O-methyl nucleotides.

In some embodiments, the 5' nucleotide of the oligonucleotide is a deoxyribonucleotide. In some embodiments, the 5' nucleotide of the oligonucleotide is a locked nucleic acid nucleotide. In some embodiments, the nucleotides of the oligonucleotide comprise deoxyribonucleotides flanked by at least one locked nucleic acid nucleotide on each of the 5' and 3' ends of the deoxyribonucleotides. In some embodiments, the nucleotide at the 3' position of the oligonucleotide has a 3' hydroxyl group or a 3' thiophosphate.

In some embodiments, the single stranded oligonucleotide comprises phosphorothioate internucleotide linkages. In some embodiments, the single stranded oligonucleotide comprises phosphorothioate internucleotide linkages between at least two nucleotides. In some embodiments, the single stranded oligonucleotide comprises phosphorothioate internucleotide linkages between all nucleotides.

It should be appreciated that the single stranded oligonucleotide can have any combination of modifications as described herein.

The oligonucleotide may comprise a nucleotide sequence having one or more of the following modification patterns.

(a) (X)Xxxxxx, (X)xXxxxx, (X)xxXxxx, (X)xxxXxx, (X)xxxxXx and (X)xxxxxX, (b) (X)XXxxxx, (X)XxXxxx, (X)XxxXxx, (X)XxxxXx, (X)XxxxxX, (X)xXXxxx, (X)xXxXxx, (X)xXxxXx, (X)xXxxxX, (X)xxXXxx, (X)xxXxXx, (X)xxXxxX, (X)xxxXXx, (X)xxxXxX and (X)xxxxXX, (c) (X)XXXxxx, (X)xXXXxx, (X)xxXXXx, (X)xxxXXX, (X)XXxXxx, (X)XXxxXx, (X)XXxxxX, (X)xXXxXx, (X)xXXxxX, (X)xxXXxX, (X)XxXXxx, (X)XxxXXx, (X)XxxxXX, (X)xXxXXx, (X)xXxxXX, (X)xxXxXX, (X)xXxXxX and (X)XxXxXx, (d) (X)xxXXX, (X)xXxXXX, (X)xXXxXX, (X)xXXXxX, (X)xXXXXx, (X)XxxXXXX, (X)XxXxXX, (X)XxXXxX, (X)XxXXXx, (X)XXxxXX, (X)XXxXxX, (X)XXxXXx, (X)XXXxxX, (X)XXXxXx, and (X)XXXXxx, (e) (X)xXXXXX, (X)XxXXXX, (X)XXxXXX, (X)XXXxXX, (X)XXXXxX and (X)XXXXXx, and (f) XXXXXX, XxXXXXX, XXxXXXX, XXXxXXX, XXXXxXX, XXXXXxX and XXXXXXx, in which "X" denotes a nucleotide analogue, (X) denotes an optional nucleotide analogue, and "x" denotes a DNA or RNA nucleotide unit. Each of the above listed patterns may appear one or more times within an oligonucleotide, alone or in combination with any of the other disclosed modification patterns.

Methods for Modulating Gene Expression

In one aspect, the invention relates to methods for modulating gene expression in a cell (e.g., a cell for which HBB, HBD, HBE1, HBG1 or HBG2 levels are reduced) for research purposes (e.g., to study the function of the gene in the cell). In another aspect, the invention relates to methods for modulating gene expression in a cell (e.g., a cell for which HBB, HBD, HBE1, HBG1 or HBG2 levels are reduced) for gene or epigenetic therapy. The cells can be in vitro, ex vivo, or in vivo (e.g., in a subject who has a disease resulting from reduced expression or activity of HBB, HBD, HBE1, HBG1 or HBG2. In some embodiments, methods for modulating gene expression in a cell comprise delivering a single stranded oligonucleotide as described herein. In some embodiments, delivery of the single stranded oligonucleotide to the cell results in a level of expression of gene that is at least 5%, 10%, 20%, 30%, 40%, 50%, 60%, 70%, 80%, 90%, 100%, 200% or more greater than a level of expression of gene in a control cell to which the single stranded oligonucleotide has not been delivered. In certain embodiments, delivery of the single stranded oligonucleotide to the cell results in a level of expression of gene that is at least 50% greater than a level of expression of gene in a control cell to which the single stranded oligonucleotide has not been delivered.

In another aspect of the invention, methods comprise administering to a subject (e.g. a human) a composition comprising a single stranded oligonucleotide as described herein to increase protein levels in the subject. In some embodiments, the increase in protein levels is at least 5%, 10%, 20%, 30%, 40%, 50%, 60%, 70%, 80%, 90%, 100%, 200%, or more, higher than the amount of a protein in the subject before administering.

As another example, to increase expression of HBB, HBD, HBE1, HBG1 or HBG2 in a cell, the methods include introducing into the cell a single stranded oligonucleotide that is sufficiently complementary to a PRC2-associated region (e.g., of a long non-coding RNA) that maps to a genomic position encompassing or in proximity to the HBB, HBD, HBE1, HBG1 or HBG2 gene.

In another aspect of the invention provides methods of treating a condition (e.g., anemia, sickle cell anemia, thalassemia) associated with decreased levels of expression of HBB, HBD, HBE1, HBG1 or HBG2 in a subject, the method comprising administering a single stranded oligonucleotide as described herein.

A subject can include a non-human mammal, e.g. mouse, rat, guinea pig, rabbit, cat, dog, goat, cow, or horse. In preferred embodiments, a subject is a human. Single stranded oligonucleotides have been employed as therapeutic moieties in the treatment of disease states in animals, including humans. Single stranded oligonucleotides can be useful therapeutic modalities that can be configured to be useful in treatment regimes for the treatment of cells, tissues and animals, especially humans.

For therapeutics, an animal, preferably a human, suspected of having anemia, sickle cell anemia and/or thalassemia is treated by administering single stranded oligonucleotide in accordance with this invention. For example, in one non-limiting embodiment, the methods comprise the step of administering to the animal in need of treatment, a therapeutically effective amount of a single stranded oligonucleotide as described herein.

Formulation, Delivery, and Dosing

The oligonucleotides described herein can be formulated for administration to a subject for treating a condition (e.g., anemia, sickle cell anemia, thalassemia) associated with decreased levels of HBB, HBD, HBE1, HBG1 or HBG2. It should be understood that the formulations, compositions and methods can be practiced with any of the oligonucleotides disclosed herein.

The formulations may conveniently be presented in unit dosage form and may be prepared by any methods well known in the art of pharmacy. The amount of active ingredient (e.g., an oligonucleotide or compound of the invention) which can be combined with a carrier material to produce a single dosage form will vary depending upon the host being treated, the particular mode of administration, e.g., intradermal or inhalation. The amount of active ingredient which can be combined with a carrier material to produce a single dosage form will generally be that amount of the compound which produces a therapeutic effect, e.g. tumor regression.

Pharmaceutical formulations of this invention can be prepared according to any method known to the art for the manufacture of pharmaceuticals. Such formulations can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

A formulated single stranded oligonucleotide composition can assume a variety of states. In some examples, the composition is at least partially crystalline, uniformly crystalline, and/or anhydrous (e.g., less than 80, 50, 30, 20, or 10% water). In another example, the single stranded oligonucleotide is in an aqueous phase, e.g., in a solution that includes water. The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the single stranded oligonucleotide composition is formulated in a manner that is compatible with the intended method of administration.

In some embodiments, the composition is prepared by at least one of the following methods: spray drying, lyophilization, vacuum drying, evaporation, fluid bed drying, or a combination of these techniques; or sonication with a lipid, freeze-drying, condensation and other self-assembly.

A single stranded oligonucleotide preparation can be formulated or administered (together or separately) in combination with another agent, e.g., another therapeutic agent or an agent that stabilizes a single stranded oligonucleotide, e.g., a protein that complexes with single stranded oligonucleotide. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the single stranded oligonucleotide preparation includes another single stranded oligonucleotide, e.g., a second single stranded oligonucleotide that modulates expression of a second gene or a second single stranded oligonucleotide that modulates expression of the first gene. Still other preparation can include at least 3, 5, ten, twenty, fifty, or a hundred or more different single stranded oligonucleotide species. Such single stranded oligonucleotides can mediated gene expression with respect to a similar number of different genes. In one embodiment, the single stranded oligonucleotide preparation includes at least a second therapeutic agent (e.g., an agent other than an oligonucleotide).

Route of Delivery

A composition that includes a single stranded oligonucleotide can be delivered to a subject by a variety of routes. Exemplary routes include: intravenous, intradermal, topical, rectal, parenteral, anal, intravaginal, intranasal, pulmonary, ocular. The term "therapeutically effective amount" is the amount of oligonucleotide present in the composition that is needed to provide the desired level of HBB, HBD, HBE1, HBG1 or HBG2 expression in the subject to be treated to give the anticipated physiological response. The term "physiologically effective amount" is that amount delivered to a subject to give the desired palliative or curative effect. The term "pharmaceutically acceptable carrier" means that the carrier can be administered to a subject with no significant adverse toxicological effects to the subject.

The single stranded oligonucleotide molecules of the invention can be incorporated into pharmaceutical compositions suitable for administration. Such compositions typically include one or more species of single stranded oligonucleotide and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the single stranded oligonucleotide in aerosol form. The vascular endothelial cells could be targeted by coating a balloon catheter with the single stranded oligonucleotide and mechanically introducing the oligonucleotide.

Topical administration refers to the delivery to a subject by contacting the formulation directly to a surface of the subject. The most common form of topical delivery is to the skin, but a composition disclosed herein can also be directly applied to other surfaces of the body, e.g., to the eye, a mucous membrane, to surfaces of a body cavity or to an internal surface. As mentioned above, the most common topical delivery is to the skin. The term encompasses several routes of administration including, but not limited to, topical and transdermal. These modes of administration typically include penetration of the skin's permeability barrier and efficient delivery to the target tissue or stratum. Topical administration can be used as a means to penetrate the epidermis and dermis and ultimately achieve systemic delivery of the composition. Topical administration can also be used as a means to selectively deliver oligonucleotides to the epidermis or dermis of a subject, or to specific strata thereof, or to an underlying tissue.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Transdermal delivery is a valuable route for the administration of lipid soluble therapeutics. The dermis is more permeable than the epidermis and therefore absorption is much more rapid through abraded, burned or denuded skin. Inflammation and other physiologic conditions that increase blood flow to the skin also enhance transdermal adsorption. Absorption via this route may be enhanced by the use of an oily vehicle (inunction) or through the use of one or more penetration enhancers. Other effective ways to deliver a composition disclosed herein via the transdermal route include hydration of the skin and the use of controlled release topical patches. The transdermal route provides a potentially effective means to deliver a composition disclosed herein for systemic and/or local therapy. In addition, iontophoresis (transfer of ionic solutes through biological membranes under the influence of an electric field), phonophoresis or sonophoresis (use of ultrasound to enhance the absorption of various therapeutic agents across biological membranes, notably the skin and the cornea), and optimization of vehicle characteristics relative to dose position and retention at the site of administration may be useful methods for enhancing the transport of topically applied compositions across skin and mucosal sites.

Both the oral and nasal membranes offer advantages over other routes of administration. For example, oligonucleotides administered through these membranes may have a rapid onset of action, provide therapeutic plasma levels, avoid first pass effect of hepatic metabolism, and avoid exposure of the oligonucleotides to the hostile gastrointestinal (GI) environment. Additional advantages include easy access to the membrane sites so that the oligonucleotide can be applied, localized and removed easily.

In oral delivery, compositions can be targeted to a surface of the oral cavity, e.g., to sublingual mucosa which includes the membrane of ventral surface of the tongue and the floor of the mouth or the buccal mucosa which constitutes the lining of the cheek. The sublingual mucosa is relatively permeable thus giving rapid absorption and acceptable bioavailability of many agents. Further, the sublingual mucosa is convenient, acceptable and easily accessible.

A pharmaceutical composition of single stranded oligonucleotide may also be administered to the buccal cavity of a human being by spraying into the cavity, without inhalation, from a metered dose spray dispenser, a mixed micellar pharmaceutical formulation as described above and a propellant. In one embodiment, the dispenser is first shaken prior to spraying the pharmaceutical formulation and propellant into the buccal cavity.

Compositions for oral administration include powders or granules, suspensions or solutions in water, syrups, slurries, emulsions, elixirs or non-aqueous media, tablets, capsules, lozenges, or troches. In the case of tablets, carriers that can be used include lactose, sodium citrate and salts of phosphoric acid. Various disintegrants such as starch, and lubricating agents such as magnesium stearate, sodium lauryl sulfate and talc, are commonly used in tablets. For oral administration in capsule form, useful diluents are lactose and high molecular weight polyethylene glycols. When aqueous suspensions are required for oral use, the nucleic acid compositions can be combined with emulsifying and suspending agents. If desired, certain sweetening and/or flavoring agents can be added.

Parenteral administration includes intravenous drip, subcutaneous, intraperitoneal or intramuscular injection, intrathecal or intraventricular administration. In some embodiments, parental administration involves administration directly to the site of disease (e.g. injection into a tumor).

Formulations for parenteral administration may include sterile aqueous solutions which may also contain buffers, diluents and other suitable additives. Intraventricular injection may be facilitated by an intraventricular catheter, for example, attached to a reservoir. For intravenous use, the total concentration of solutes should be controlled to render the preparation isotonic.

Any of the single stranded oligonucleotides described herein can be administered to ocular tissue. For example, the compositions can be applied to the surface of the eye or nearby tissue, e.g., the inside of the eyelid. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or poly(vinyl alcohol), preservatives such as sorbic acid, EDTA or benzylchronium chloride, and the usual quantities of diluents and/or carriers. The single stranded oligonucleotide can also be administered to the interior of the eye, and can be introduced by a needle or other delivery device which can introduce it to a selected area or structure.

Pulmonary delivery compositions can be delivered by inhalation by the patient of a dispersion so that the composition, preferably single stranded oligonucleotides, within the dispersion can reach the lung where it can be readily absorbed through the alveolar region directly into blood circulation. Pulmonary delivery can be effective both for systemic delivery and for localized delivery to treat diseases of the lungs.

Pulmonary delivery can be achieved by different approaches, including the use of nebulized, aerosolized, micellular and dry powder-based formulations. Delivery can be achieved with liquid nebulizers, aerosol-based inhalers, and dry powder dispersion devices. Metered-dose devices are preferred. One of the benefits of using an atomizer or inhaler is that the potential for contamination is minimized because the devices are self-contained. Dry powder dispersion devices, for example, deliver agents that may be readily formulated as dry powders. A single stranded oligonucleotide composition may be stably stored as lyophilized or spray-dried powders by itself or in combination with suitable powder carriers. The delivery of a composition for inhalation can be mediated by a dosing timing element which can include a timer, a dose counter, time measuring device, or a time indicator which when incorporated into the device enables dose tracking, compliance monitoring, and/or dose triggering to a patient during administration of the aerosol medicament.

The term "powder" means a composition that consists of finely dispersed solid particles that are free flowing and capable of being readily dispersed in an inhalation device and subsequently inhaled by a subject so that the particles reach the lungs to permit penetration into the alveoli. Thus, the powder is said to be "respirable." Preferably the average particle size is less than about 10 μm in diameter preferably with a relatively uniform spheroidal shape distribution. More preferably the diameter is less than about 7.5 μm and most preferably less than about 5.0 μm. Usually the particle size distribution is between about 0.1 μm and about 5 μm in diameter, particularly about 0.3 μm to about 5 μm.

The term "dry" means that the composition has a moisture content below about 10% by weight (% w) water, usually below about 5% w and preferably less it than about 3% w.

A dry composition can be such that the particles are readily dispersible in an inhalation device to form an aerosol.

The types of pharmaceutical excipients that are useful as carrier include stabilizers such as human serum albumin (HSA), bulking agents such as carbohydrates, amino acids and polypeptides; pH adjusters or buffers; salts such as sodium chloride; and the like. These carriers may be in a crystalline or amorphous form or may be a mixture of the two.

Suitable pH adjusters or buffers include organic salts prepared from organic acids and bases, such as sodium citrate, sodium ascorbate, and the like; sodium citrate is preferred. Pulmonary administration of a micellar single stranded oligonucleotide formulation may be achieved through metered dose spray devices with propellants such as tetrafluoroethane, heptafluoroethane, dimethylfluoropropane, tetrafluoropropane, butane, isobutane, dimethyl ether and other non-CFC and CFC propellants.

Exemplary devices include devices which are introduced into the vasculature, e.g., devices inserted into the lumen of a vascular tissue, or which devices themselves form a part of the vasculature, including stents, catheters, heart valves, and other vascular devices. These devices, e.g., catheters or stents, can be placed in the vasculature of the lung, heart, or leg.

Other devices include non-vascular devices, e.g., devices implanted in the peritoneum, or in organ or glandular tissue, e.g., artificial organs. The device can release a therapeutic substance in addition to a single stranded oligonucleotide, e.g., a device can release insulin.

In one embodiment, unit doses or measured doses of a composition that includes single stranded oligonucleotide are dispensed by an implanted device. The device can include a sensor that monitors a parameter within a subject. For example, the device can include pump, e.g., and, optionally, associated electronics.

Tissue, e.g., cells or organs can be treated with a single stranded oligonucleotide, ex vivo and then administered or implanted in a subject. The tissue can be autologous, allogeneic, or xenogeneic tissue. E.g., tissue can be treated to reduce graft v. host disease. In other embodiments, the tissue is allogeneic and the tissue is treated to treat a disorder characterized by unwanted gene expression in that tissue. E.g., tissue, e.g., hematopoietic cells, e.g., bone marrow hematopoietic cells, can be treated to inhibit unwanted cell proliferation. Introduction of treated tissue, whether autologous or transplant, can be combined with other therapies. In some implementations, the single stranded oligonucleotide treated cells are insulated from other cells, e.g., by a semi-permeable porous barrier that prevents the cells from leaving the implant, but enables molecules from the body to reach the cells and molecules produced by the cells to enter the body. In one embodiment, the porous barrier is formed from alginate.

In one embodiment, a contraceptive device is coated with or contains a single stranded oligonucleotide. Exemplary devices include condoms, diaphragms, IUD (implantable uterine devices, sponges, vaginal sheaths, and birth control devices.

Dosage

In one aspect, the invention features a method of administering a single stranded oligonucleotide (e.g., as a compound or as a component of a composition) to a subject (e.g., a human subject). In one embodiment, the unit dose is between about 10 mg and 25 mg per kg of bodyweight. In one embodiment, the unit dose is between about 1 mg and 100 mg per kg of bodyweight. In one embodiment, the unit dose is between about 0.1 mg and 500 mg per kg of bodyweight. In some embodiments, the unit dose is more than 0.001, 0.005, 0.01, 0.05, 0.1, 0.5, 1, 2, 5, 10, 25, 50 or 100 mg per kg of bodyweight.

The defined amount can be an amount effective to treat or prevent a disease or disorder, e.g., a disease or disorder associated with the HBB, HBD, HBE1, HBG1 or HBG2. The unit dose, for example, can be administered by injection (e.g., intravenous or intramuscular), an inhaled dose, or a topical application.

In some embodiments, the unit dose is administered daily. In some embodiments, less frequently than once a day, e.g., less than every 2, 4, 8 or 30 days. In another embodiment, the unit dose is not administered with a frequency (e.g., not a regular frequency). For example, the unit dose may be administered a single time. In some embodiments, the unit dose is administered more than once a day, e.g., once an hour, two hours, four hours, eight hours, twelve hours, etc.

In one embodiment, a subject is administered an initial dose and one or more maintenance doses of a single stranded oligonucleotide. The maintenance dose or doses are generally lower than the initial dose, e.g., one-half less of the initial dose. A maintenance regimen can include treating the subject with a dose or doses ranging from 0.0001 to 100 mg/kg of body weight per day, e.g., 100, 10, 1, 0.1, 0.01, 0.001, or 0.0001 mg per kg of bodyweight per day. The maintenance doses may be administered no more than once every 1, 5, 10, or 30 days. Further, the treatment regimen may last for a period of time which will vary depending upon the nature of the particular disease, its severity and the overall condition of the patient. In some embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the oligonucleotide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In some embodiments, the oligonucleotide pharmaceutical composition includes a plurality of single stranded oligonucleotide species. In another embodiment, the single stranded oligonucleotide species has sequences that are non-overlapping and non-adjacent to another species with respect to a naturally occurring target sequence (e.g., a PRC2-associated region). In another embodiment, the plurality of single stranded oligonucleotide species is specific for different PRC2-associated regions. In another embodiment, the single stranded oligonucleotide is allele specific. In some cases, a patient is treated with a single stranded oligonucleotide in conjunction with other therapeutic modalities.

Following successful treatment, it may be desirable to have the patient undergo maintenance therapy to prevent the recurrence of the disease state, wherein the compound of the invention is administered in maintenance doses, ranging from 0.0001 mg to 100 mg per kg of body weight.

The concentration of the single stranded oligonucleotide composition is an amount sufficient to be effective in treating or preventing a disorder or to regulate a physiological condition in humans. The concentration or amount of single stranded oligonucleotide administered will depend on the parameters determined for the agent and the method of administration, e.g. nasal, buccal, pulmonary. For example, nasal formulations may tend to require much lower concentrations of some ingredients in order to avoid irritation or burning of the nasal passages. It is sometimes desirable to dilute an oral formulation up to 10-100 times in order to provide a suitable nasal formulation.

Certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a single stranded oligonucleotide can include a single treatment or, preferably, can include a series of treatments. It will also be appreciated that the effective dosage of a single stranded oligonucleotide used for treatment may increase or decrease over the course of a particular treatment. For example, the subject can be monitored after administering a single stranded oligonucleotide composition. Based on information from the monitoring, an additional amount of the single stranded oligonucleotide composition can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of HBB, HBD, HBE1, HBG1 or HBG2 expression levels in the body of the patient. Persons of ordinary skill can easily determine optimum dosages, dosing methodologies and repetition rates. Optimum dosages may vary depending on the relative potency of individual compounds, and can generally be estimated based on EC50s found to be effective in in vitro and in vivo animal models. In some embodiments, the animal models include transgenic animals that express a human HBB, HBD, HBE1, HBG1 or HBG2. In another embodiment, the composition for testing includes a single stranded oligonucleotide that is complementary, at least in an internal region, to a sequence that is conserved between HBB, HBD, HBE1, HBG1 or HBG2 in the animal model and the HBB, HBD, HBE1, HBG1 or HBG2 in a human.

In one embodiment, the administration of the single stranded oligonucleotide composition is parenteral, e.g. intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The composition can be provided in measured doses or in a dispenser which delivers a metered dose. Selected modes of delivery are discussed in more detail below.

Kits

In certain aspects of the invention, kits are provided, comprising a container housing a composition comprising a single stranded oligonucleotide. In some embodiments, the composition is a pharmaceutical composition comprising a single stranded oligonucleotide and a pharmaceutically acceptable carrier. In some embodiments, the individual components of the pharmaceutical composition may be provided in one container. Alternatively, it may be desirable to provide the components of the pharmaceutical composition separately in two or more containers, e.g., one container for single stranded oligonucleotides, and at least another for a carrier compound. The kit may be packaged in a number of different configurations such as one or more containers in a single box. The different components can be combined, e.g., according to instructions provided with the kit. The components can be combined according to a method described herein, e.g., to prepare and administer a pharmaceutical composition. The kit can also include a delivery device.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

The invention is further described in the following examples, which do not limit the scope of the invention described in the claims.
Materials and Methods:
Real Time PCR RNA is harvested from the cells using Promega SV 96 Total RNA Isolation system or Trizol omitting the DNAse step. RNA harvested from cells is normalized so that equal RNA is input to each reverse transcription reaction. Reverse transcriptase reactions are performed using the Superscript II kit and real time PCR performed on cDNA samples using icycler SYBR green chemistry (Biorad). A baseline level of mRNA expression for HBB, HBD, HBE1, HBG1 or HBG2 is determined through quantitative PCR as outlined above. Baseline levels are also determined for mRNA of various housekeeping genes which are constitutively expressed. A "control" housekeeping gene with approximately the same level of baseline expression as the target gene is chosen for comparison purposes.
Cell Culture Human hepatocyte Hep3B, human hepatocyte HepG2 cells, mouse hepatoma Hepa 1-6 cells, and human renal proximal tubule epithelial cells (RPTEC) are cultured using conditions known in the art (see, e.g. Current Protocols in Cell Biology).
Oligonucleotide Design Oligonucleotides were designed within PRC2-interacting regions in order to upregulate HBB or HBG2. The sequence and structure of each oligonucleotide is shown in Table 3. A description of the nucleotide analogs, modifications and intranucleotide linkages used for certain oligonucleotides described is provided in Table 2.

SEQ ID NOs: 3789 to 3796 are control oligos. SEQ ID NO: 3789 is a splice-altering oligo targeting a site in intron 2 of HBB. SEQ ID NOs: 3790-3793 are 15-mer subsequences of SEQ ID NO: 3789. SEQ ID NO: 3795 is a dimer of SEQ ID NO: 3789. SEQ ID NOs: 3794 and 3796 are a control oligo and a dimer version of the control oligo, respectively.
In Vitro Transfection of Cells with Oligonucleotides Oligonucleotides are designed within PRC2-interacting regions in order to upregulate HBB, HBD, HBE1, HBG1 or HBG2. Cells are seeded into each well of 24-well plates at a density of 25,000 cells per 500 uL and transfections are performed with Lipofectamine and the single stranded oligonucleotides. Control wells contain Lipofectamine alone. At 48 hours post-transfection, approximately 200 uL of cell culture supernatants are stored at −80 C for ELISA. At 48 hours post-transfection, RNA is harvested from the cells and quantitative PCR is carried out as outlined above. The percent induction of target mRNA expression by each oligonucleotide is determined by normalizing mRNA levels in the presence of the oligonucleotide to the mRNA levels in the presence of control (Lipofectamine alone). This is compared side-by-side with the increase in mRNA expression of the "control" housekeeping gene.

In Vitro Delivery of Single Stranded Oligonucleotides

Oligonucleotides are designed as candidates for upregulating HBB, HBD, HBE1, HBG1 or HBG2 expression. The single stranded oligonucleotides are designed to be complementary to a PRC2-interacting region within a sequence as set forth as any one of SEQ ID NOS: 1-10. The oligonucleotides are tested in at least duplicate. Briefly, cells are transfected in vitro with each of the oligonucleotides as described above. HBB, HBD, HBE1, HBG1 or HBG2 expression in cells following treatment is evaluated by qRT-PCR. Oligonucleotides that upregulate HBB, HBD, HBE1, HBG1 or HBG2 expression are identified.

TABLE 1

| Hexamers that are not seed sequences of human miRNAs |
|---|
| AAAAAA, AAAAAG, AAAACA, AAAAGA, AAAAGC, AAAAGG, AAAAUA, AAACAA, AAACAC, AAACAG, |
| AAACAU, AAACCC, AAACCU, AAACGA, AAACGC, AAACGU, AAACUA, AAACUC, AAACUU, AAAGAU, |
| AAAGCC, AAAGGA, AAAGGG, AAAGUC, AAAUAC, AAAUAU, AAAUCG, AAAUCU, AAAUGC, AAAUGU, |
| AAAUUA, AAAUUG, AACAAC, AACAAG, AACAAU, AACACA, AACACG, AACAGA, AACAGC, AACAGG, |
| AACAUC, AACAUG, AACCAA, AACCAC, AACCAG, AACCAU, AACCCC, AACCCG, AACCGA, AACCGC, |
| AACCGG, AACCUA, AACCUU, AACGAA, AACGAC, AACGAG, AACGAU, AACGCU, AACGGG, AACGGU, |
| AACGUA, AACGUC, AACGUG, AACGUU, AACUAU, AACUCA, AACUCC, AACUCG, AACUGA, AACUGC, |
| AACUGU, AACUUA, AACUUC, AACUUG, AACUUU, AAGAAA, AAGAAG, AAGAAU, AAGACG, AAGAGA, |
| AAGAGC, AAGAGG, AAGAGU, AAGAUU, AAGCAA, AAGCAC, AAGCAG, AAGCAU, AAGCCA, AAGCCC, |
| AAGCCG, AAGCCU, AAGCGA, AAGCGG, AAGCGU, AAGCUA, AAGGAA, AAGGAC, AAGGCU, AAGGGC, |
| AAGGGU, AAGGUU, AAGUAA, AAGUAC, AAGUAU, AAGUCC, AAGUCG, AAGUGA, AAGUGG, AAGUUA, |
| AAGUUU, AAUAAA, AAUAAC, AAUAAG, AAUAAU, AAUACA, AAUACC, AAUACG, AAUAGA, AAUAGC, |
| AAUAGG, AAUAGU, AAUAUC, AAUAUU, AAUCAA, AAUCAU, AAUCCA, AAUCCC, AAUCCG, AAUCGA, |
| AAUCGC, AAUCGU, AAUCUA, AAUCUG, AAUCUU, AAUGAA, AAUGAC, AAUGAG, AAUGAU, AAUGCG, |
| AAUGCU, AAUGGA, AAUGGU, AAUGUA, AAUGUC, AAUGUG, AAUUAA, AAUUAC, AAUUAG, AAUUCC, |
| AAUUCG, AAUUGA, AAUUGG, AAUUGU, AAUUUC, AAUUUG, ACAAAA, ACAAAC, ACAAAG, ACAAAU, |
| ACAACC, ACAACG, ACAACU, ACAAGA, ACAAGC, ACAAGU, ACAAUC, ACAAUG, ACAAUU, ACACAG, |
| ACACCA, ACACCC, ACACCG, ACACCU, ACACGA, ACACGC, ACACGU, ACACUC, ACACUG, ACACUU, |
| ACAGAA, ACAGAC, ACAGCC, ACAGCG, ACAGCU, ACAGGG, ACAGUC, ACAGUG, ACAGUU, ACAUAA, |
| ACAUAC, ACAUCC, ACAUCG, ACAUCU, ACAUGA, ACAUGC, ACAUGU, ACAUUG, ACAUUU, ACCAAA, |
| ACCAAC, ACCAAG, ACCAAU, ACCACC, ACCACG, ACCAGA, ACCAGU, ACCAUA, ACCAUG, ACCAUU, |
| ACCCAA, ACCCAC, ACCCCA, ACCCCG, ACCCGA, ACCCGC, ACCCUA, ACCCUC, ACCCUU, ACCGAA, |
| ACCGAC, ACCGAU, ACCGCA, ACCGCC, ACCGCG, ACCGCU, ACCGGA, ACCGGC, ACCGGU, ACCGUA, |
| ACCGUC, ACCGUG, ACCGUU, ACCUAA, ACCUAC, ACCUAG, ACCUAU, ACCUCA, ACCUCC, ACCUCG, |
| ACCUCU, ACCUGA, ACCUGC, ACCUGU, ACCUUA, ACCUUC, ACCUUU, ACGAAA, ACGAAC, ACGAAG, |
| ACGAAU, ACGACA, ACGACC, ACGACG, ACGACU, ACGAGA, ACGAGC, ACGAGG, ACGAGU, ACGAUA, |
| ACGAUC, ACGAUG, ACGAUU, ACGCAA, ACGCAG, ACGCAU, ACGCCC, ACGCCG, ACGCCU, ACGCGA, |
| ACGCGG, ACGCGU, ACGCUA, ACGCUG, ACGCUU, ACGGAA, ACGGAC, ACGGAG, ACGGAU, ACGGCC, |
| ACGGCG, ACGGCU, ACGGGC, ACGGGG, ACGGGU, ACGGUA, ACGGUC, ACGGUG, ACGGUU, ACGUAA, |
| ACGUAC, ACGUAU, ACGUCC, ACGUCG, ACGUCU, ACGUGA, ACGUGC, ACGUGG, ACGUGU, ACGUUA, |
| ACGUUC, ACGUUG, ACGUUU, ACUAAA, ACUAAG, ACUAAU, ACUACA, ACUACC, ACUACG, ACUACU, |

TABLE 1-continued

Hexamers that are not seed sequences of human miRNAs

ACUAGG, ACUAUC, ACUAUG, ACUAUU, ACUCAU, ACUCCC, ACUCCG, ACUCCU, ACUCGA, ACUCGC,
ACUCGG, ACUCUC, ACUCUU, ACUGAG, ACUGAU, ACUGCC, ACUGCG, ACUGCU, ACUGGG, ACUGGU,
ACUGUC, ACUUAA, ACUUAC, ACUUAU, ACUUCA, ACUUCC, ACUUCG, ACUUCU, ACUUGA, ACUUGC,
ACUUGU, ACUUUA, ACUUUC, ACUUUG, AGAAAA, AGAAAC, AGAAAG, AGAACC, AGAACG, AGAACU,
AGAAGC, AGAAGU, AGAAUA, AGAAUC, AGAAUG, AGAAUU, AGACAA, AGACAC, AGACAU, AGACCA,
AGACCC, AGACCG, AGACCU, AGACGA, AGACGC, AGACGU, AGACUA, AGACUC, AGACUU, AGAGAC,
AGAGAG, AGAGAU, AGAGCC, AGAGCG, AGAGCU, AGAGGC, AGAGGG, AGAGGU, AGAGUA, AGAGUU,
AGAUAC, AGAUAG, AGAUAU, AGAUCC, AGAUCG, AGAUCU, AGAUGA, AGAUGC, AGAUGG, AGAUUA,
AGAUUC, AGAUUG, AGAUUU, AGCAAC, AGCACA, AGCACG, AGCACU, AGCAGA, AGCAUA, AGCAUC,
AGCAUG, AGCCAA, AGCCAU, AGCCCA, AGCCGA, AGCCGC, AGCCGG, AGCCGU, AGCCUA, AGCCUC,
AGCGAA, AGCGAG, AGCGAU, AGCGCA, AGCGCC, AGCGCG, AGCGCU, AGCGGA, AGCGGC, AGCGGU,
AGCGUA, AGCGUC, AGCGUG, AGCGUU, AGCUAA, AGCUAC, AGCUAG, AGCUAU, AGCUCA, AGCUCC,
AGCUCG, AGCUCU, AGCUGA, AGCUGG, AGCUGU, AGCUUC, AGCUUU, AGGAAU, AGGACC, AGGACG,
AGGAGA, AGGAGU, AGGAUA, AGGCAA, AGGCAU, AGGCCG, AGGCGA, AGGCGC, AGGCGG, AGGCUA,
AGGCUC, AGGCUU, AGGGAC, AGGGAU, AGGGGA, AGGGGU, AGGGUA, AGGGUG, AGGUAA, AGGUAC,
AGGUCA, AGGUCC, AGGUCU, AGGUGA, AGGUGC, AGGUGG, AGGUGU, AGGUUC, AGGUUG, AGUAAA,
AGUAAG, AGUAAU, AGUACA, AGUACG, AGUAGC, AGUAGG, AGUAUA, AGUAUC, AGUAUG, AGUAUU,
AGUCAA, AGUCAC, AGUCAG, AGUCAU, AGUCCA, AGUCCG, AGUCCU, AGUCGA, AGUCGC, AGUCGG,
AGUCGU, AGUCUA, AGUCUC, AGUCUG, AGUCUU, AGUGAA, AGUGAC, AGUGCG, AGUGGG, AGUGUC,
AGUUAA, AGUUAC, AGUUAG, AGUUCC, AGUUCG, AGUUGA, AGUUGC, AGUUGU, AGUUUA, AGUUUC,
AGUUUG, AGUUUU, AUAAAC, AUAAAU, AUAACA, AUAACC, AUAACG, AUAACU, AUAAGA, AUAAGC,
AUAAGG, AUAAGU, AUAAUC, AUAAUG, AUAAUU, AUACAC, AUACAG, AUACAU, AUACCA, AUACCC,
AUACCG, AUACGA, AUACGC, AUACGG, AUACGU, AUACUA, AUACUC, AUACUG, AUACUU, AUAGAA,
AUAGAC, AUAGAU, AUAGCA, AUAGCG, AUAGCU, AUAGGA, AUAGGU, AUAGUA, AUAGUC, AUAGUG,
AUAGUU, AUAUAC, AUAUAG, AUAUCC, AUAUCG, AUAUCU, AUAUGA, AUAUGC, AUAUGG, AUAUGU,
AUAUUC, AUAUUG, AUAUUU, AUCAAA, AUCAAC, AUCAAG, AUCAAU, AUCACA, AUCACC, AUCACG,
AUCAGC, AUCAGG, AUCCAA, AUCCAU, AUCCCC, AUCCCG, AUCCGA, AUCCGC, AUCCGG, AUCCUA,
AUCCUC, AUCCUG, AUCGAA, AUCGAC, AUCGAG, AUCGAU, AUCGCA, AUCGCC, AUCGCG, AUCGCU,
AUCGGC, AUCGGG, AUCGGU, AUCGUC, AUCGUG, AUCGUU, AUCUAA, AUCUAC, AUCUAG, AUCUAU,
AUCUCC, AUCUCG, AUCUGU, AUCUUG, AUCUUU, AUGAAA, AUGAAC, AUGAAG, AUGAAU, AUGACC,
AUGACU, AUGAGG, AUGAGU, AUGAUA, AUGAUC, AUGAUU, AUGCAA, AUGCAG, AUGCCA, AUGCCC,
AUGCCG, AUGCGA, AUGCGG, AUGCGU, AUGCUC, AUGCUU, AUGGAC, AUGGCC, AUGGGA, AUGGGC,
AUGGGU, AUGGUC, AUGGUG, AUGUAC, AUGUAU, AUGUCA, AUGUCC, AUGUCG, AUGUGU, AUGUUA,
AUGUUC, AUUAAA, AUUAAC, AUUAAG, AUUAAU, AUUACA, AUUACC, AUUACG, AUUACU, AUUAGA,
AUUAGC, AUUAGG, AUUAGU, AUUAUA, AUUAUC, AUUAUG, AUUCAC, AUUCCA, AUUCCG, AUUCCU,
AUUCGA, AUUCGC, AUUCGG, AUUCGU, AUUCUA, AUUCUC, AUUCUU, AUUGAA, AUUGAC, AUUGAU,
AUUGCC, AUUGCG, AUUGCU, AUUGGA, AUUGGC, AUUGGG, AUUGGU, AUUGUA, AUUGUC, AUUGUG,
AUUGUU, AUUUAA, AUUUAG, AUUUAU, AUUUCC, AUUUCG, AUUUCU, AUUUGA, AUUUGC, AUUUGU,
AUUUUA, AUUUUC, AUUUUG, AUUUUU, CAAAAG, CAAACA, CAAACC, CAAACG, CAAACU, CAAAGA,

TABLE 1-continued

Hexamers that are not seed sequences of human miRNAs

CAAAGG, CAAAUA, CAAAUU, CAACAC, CAACAU, CAACCA, CAACCC, CAACCG, CAACGA, CAACGC,
CAACGG, CAACGU, CAACUA, CAACUC, CAACUG, CAACUU, CAAGAA, CAAGAC, CAAGAU, CAAGCA,
CAAGCC, CAAGCG, CAAGCU, CAAGGA, CAAGGG, CAAGUC, CAAGUG, CAAGUU, CAAUAA, CAAUAC,
CAAUAG, CAAUCC, CAAUCG, CAAUCU, CAAUGA, CAAUGC, CAAUGG, CAAUGU, CAAUUC, CAAUUG,
CAAUUU, CACAAU, CACACA, CACACG, CACACU, CACAGA, CACAGC, CACAGG, CACAUA, CACAUC,
CACAUU, CACCAA, CACCAC, CACCAU, CACCCA, CACCCC, CACCCG, CACCGA, CACCGC, CACCGG,
CACCGU, CACCUA, CACCUU, CACGAA, CACGAC, CACGAG, CACGAU, CACGCA, CACGCC, CACGCU,
CACGGA, CACGGC, CACGGG, CACGGU, CACGUA, CACGUC, CACGUG, CACGUU, CACUAA, CACUAG,
CACUAU, CACUCA, CACUCG, CACUGA, CACUGC, CACUGG, CACUUA, CACUUC, CACUUU, CAGAAA,
CAGAAG, CAGAAU, CAGACC, CAGACG, CAGAGC, CAGAUA, CAGAUC, CAGCCG, CAGCCU, CAGCGA,
CAGCGC, CAGCGG, CAGCGU, CAGCUC, CAGCUU, CAGGAU, CAGGGG, CAGGGU, CAGGUA, CAGGUC,
CAGGUU, CAGUAC, CAGUCG, CAGUUG, CAUAAA, CAUAAC, CAUAAG, CAUAAU, CAUACA, CAUACC,
CAUACG, CAUACU, CAUAGA, CAUAGG, CAUAGU, CAUAUA, CAUAUC, CAUAUG, CAUCAA, CAUCAC,
CAUCAG, CAUCAU, CAUCCA, CAUCCC, CAUCCG, CAUCGA, CAUCGC, CAUCGG, CAUCGU, CAUCUA,
CAUCUC, CAUCUG, CAUCUU, CAUGAA, CAUGAC, CAUGAG, CAUGAU, CAUGCA, CAUGCC, CAUGCG,
CAUGCU, CAUGGC, CAUGGG, CAUGGU, CAUGUA, CAUGUC, CAUGUU, CAUUAA, CAUUAC, CAUUAG,
CAUUCA, CAUUCC, CAUUCG, CAUUCU, CAUUGA, CAUUGG, CAUUUC, CAUUUG, CAUUUU, CCAAAA,
CCAAAC, CCAAAG, CCAAAU, CCAACA, CCAACC, CCAACG, CCAACU, CCAAGA, CCAAGC, CCAAGG,
CCAAUC, CCAAUG, CCAAUU, CCACAA, CCACAC, CCACAG, CCACAU, CCACCA, CCACCC, CCACCG,
CCACCU, CCACGA, CCACGC, CCACGG, CCACGU, CCACUA, CCACUC, CCACUU, CCAGAA, CCAGAC,
CCAGAG, CCAGCC, CCAGGU, CCAGUC, CCAGUU, CCAUAA, CCAUAC, CCAUAG, CCAUAU, CCAUCA,
CCAUCC, CCAUCU, CCAUGA, CCAUGC, CCAUGG, CCAUUC, CCAUUG, CCAUUU, CCCAAC, CCCAAG,
CCCAAU, CCCACA, CCCAGA, CCCAGC, CCCAGU, CCCAUA, CCCAUC, CCCAUG, CCCAUU, CCCCAA,
CCCCAG, CCCCAU, CCCCCC, CCCCCG, CCCCCU, CCCCGA, CCCCGC, CCCCGU, CCCCUA, CCCCUC,
CCCGAA, CCCGAC, CCCGAU, CCCGCA, CCCGCU, CCCGGA, CCCGGC, CCCGUA, CCCGUG, CCCGUU,
CCCUAA, CCCUAG, CCCUCA, CCCUCU, CCCUGC, CCCUUA, CCCUUC, CCCUUU, CCGAAA, CCGAAC,
CCGAAU, CCGACA, CCGACC, CCGACG, CCGACU, CCGAGA, CCGAGG, CCGAGU, CCGAUA, CCGAUC,
CCGAUG, CCGAUU, CCGCAA, CCGCAC, CCGCAG, CCGCAU, CCGCCA, CCGCCC, CCGCCG, CCGCCU,
CCGCGA, CCGCGC, CCGCGG, CCGCGU, CCGCUA, CCGCUC, CCGCUG, CCGCUU, CCGGAA, CCGGAU,
CCGGCA, CCGGCC, CCGGCG, CCGGCU, CCGGGA, CCGGGC, CCGGGG, CCGGGU, CCGGUA, CCGGUC,
CCGGUG, CCGUAA, CCGUAG, CCGUAU, CCGUCA, CCGUCC, CCGUCG, CCGUGA, CCGUGU, CCGUUA,
CCGUUC, CCGUUG, CCGUUU, CCUAAC, CCUAAG, CCUAAU, CCUACA, CCUACC, CCUACG, CCUACU,
CCUAGA, CCUAGC, CCUAGG, CCUAGU, CCUAUA, CCUAUC, CCUAUG, CCUAUU, CCUCAA, CCUCAC,
CCUCAG, CCUCAU, CCUCCA, CCUCCC, CCUCCG, CCUCGA, CCUCGC, CCUCGG, CCUCGU, CCUCUA,
CCUCUG, CCUGAC, CCUGAU, CCUGCA, CCUGGG, CCUGGU, CCUGUU, CCUUAA, CCUUAC, CCUUAG,
CCUUAU, CCUUCG, CCUUGA, CCUUGU, CCUUUA, CCUUUC, CCUUUU, CGAAAA, CGAAAC, CGAAAG,
CGAAAU, CGAACA, CGAACC, CGAACG, CGAACU, CGAAGA, CGAAGC, CGAAGG, CGAAGU, CGAAUA,
CGAAUC, CGAAUG, CGAAUU, CGACAA, CGACAC, CGACAU, CGACCA, CGACCU, CGACGA, CGACGC,
CGACGG, CGACGU, CGACUA, CGACUG, CGACUU, CGAGAA, CGAGAC, CGAGAG, CGAGAU, CGAGCA,

TABLE 1-continued

Hexamers that are not seed sequences of human miRNAs

CGAGCC, CGAGCG, CGAGCU, CGAGGC, CGAGGG, CGAGGU, CGAGUA, CGAGUC, CGAGUG, CGAGUU,
CGAUAA, CGAUAC, CGAUAG, CGAUAU, CGAUCA, CGAUCC, CGAUCG, CGAUCU, CGAUGA, CGAUGC,
CGAUGG, CGAUGU, CGAUUA, CGAUUC, CGAUUG, CGAUUU, CGCAAA, CGCAAC, CGCAAG, CGCAAU,
CGCACA, CGCACC, CGCACG, CGCAGA, CGCAGC, CGCAGG, CGCAGU, CGCAUA, CGCAUC, CGCAUG,
CGCAUU, CGCCAA, CGCCAC, CGCCAG, CGCCAU, CGCCCA, CGCCCC, CGCCCG, CGCCGA, CGCCGC,
CGCCGG, CGCCGU, CGCCUA, CGCCUG, CGCCUU, CGCGAA, CGCGAC, CGCGAG, CGCGAU, CGCGCA,
CGCGCC, CGCGCG, CGCGCU, CGCGGA, CGCGGC, CGCGGG, CGCGGU, CGCGUA, CGCGUC, CGCGUG,
CGCGUU, CGCUAA, CGCUAC, CGCUAG, CGCUAU, CGCUCA, CGCUCC, CGCUCG, CGCUCU, CGCUGA,
CGCUGC, CGCUGG, CGCUGU, CGCUUA, CGCUUC, CGCUUG, CGGAAA, CGGAAC, CGGAAG, CGGACA,
CGGACC, CGGACG, CGGACU, CGGAGC, CGGAGG, CGGAGU, CGGAUA, CGGAUU, CGGCAA, CGGCAC,
CGGCAG, CGGCCA, CGGCCC, CGGCCG, CGGCGC, CGGCGG, CGGCGU, CGGCUA, CGGCUC, CGGCUG,
CGGCUU, CGGGAA, CGGGAC, CGGGAG, CGGGAU, CGGGCA, CGGGCC, CGGGCG, CGGGCU, CGGGGU,
CGGGUA, CGGGUC, CGGGUG, CGGUAA, CGGUAC, CGGUAG, CGGUAU, CGGUCA, CGGUCG, CGGUCU,
CGGUGA, CGGUGG, CGGUGU, CGGUUA, CGGUUC, CGGUUG, CGGUUU, CGUAAA, CGUAAC, CGUAAG,
CGUAAU, CGUACA, CGUACG, CGUACU, CGUAGA, CGUAGC, CGUAGG, CGUAGU, CGUAUA, CGUAUC,
CGUAUG, CGUAUU, CGUCAA, CGUCAC, CGUCAG, CGUCAU, CGUCCA, CGUCCC, CGUCCG, CGUCCU,
CGUCGA, CGUCGG, CGUCGU, CGUCUA, CGUCUC, CGUCUG, CGUCUU, CGUGAA, CGUGAC, CGUGAG,
CGUGAU, CGUGCC, CGUGCG, CGUGCU, CGUGGA, CGUGGG, CGUGGU, CGUGUA, CGUGUG, CGUUAA,
CGUUAC, CGUUAG, CGUUAU, CGUUCA, CGUUCC, CGUUCG, CGUUCU, CGUUGA, CGUUGC, CGUUGU,
CGUUUA, CGUUUC, CGUUUU, CUAAAA, CUAAAC, CUAAAU, CUAACA, CUAACC, CUAACG, CUAACU,
CUAAGA, CUAAGC, CUAAGU, CUAAUA, CUAAUC, CUAAUG, CUACAC, CUACAU, CUACCA, CUACCC,
CUACCG, CUACCU, CUACGA, CUACGC, CUACGG, CUACGU, CUACUA, CUACUC, CUACUG, CUAGAA,
CUAGAG, CUAGAU, CUAGCA, CUAGCC, CUAGCG, CUAGCU, CUAGGA, CUAGGG, CUAGGU, CUAGUG,
CUAGUU, CUAUAA, CUAUAG, CUAUAU, CUAUCA, CUAUCC, CUAUCG, CUAUCU, CUAUGA, CUAUGC,
CUAUGG, CUAUGU, CUAUUA, CUAUUG, CUCAAC, CUCAAG, CUCAAU, CUCACC, CUCACG, CUCAGC,
CUCAUA, CUCAUC, CUCAUG, CUCAUU, CUCCAC, CUCCCC, CUCCCG, CUCCGA, CUCCGC, CUCCGG,
CUCCUA, CUCCUC, CUCCUU, CUCGAA, CUCGAC, CUCGAG, CUCGAU, CUCGCA, CUCGCC, CUCGCG,
CUCGGG, CUCGGU, CUCGUA, CUCGUC, CUCGUG, CUCGUU, CUCUAA, CUCUAC, CUCUAU, CUCUCA,
CUCUCC, CUCUCU, CUCUGC, CUCUGU, CUCUUA, CUCUUG, CUGAAG, CUGACC, CUGACG, CUGAGC,
CUGAUA, CUGAUC, CUGCCG, CUGCCU, CUGCGA, CUGCUA, CUGCUU, CUGGAG, CUGGAU, CUGGCG,
CUGGGU, CUGUAC, CUGUCA, CUGUCC, CUGUCG, CUGUGG, CUGUGU, CUGUUA, CUGUUU, CUUAAC,
CUUAAG, CUUAAU, CUUACC, CUUACG, CUUAGA, CUUAGC, CUUAGG, CUUAGU, CUUAUA, CUUAUC,
CUUAUG, CUUAUU, CUUCAG, CUUCAU, CUUCCA, CUUCCC, CUUCCG, CUUCCU, CUUCGA, CUUCGC,
CUUCGG, CUUCGU, CUUCUA, CUUGAC, CUUGAG, CUUGAU, CUUGCA, CUUGCC, CUUGCG, CUUGCU,
CUUGGC, CUUGGU, CUUGUU, CUUUAC, CUUUAG, CUUUAU, CUUUCA, CUUUCG, CUUUCU, CUUUGA,
CUUUGC, CUUUGU, CUUUUA, CUUUUC, CUUUUG, CUUUUU, GAAAAA, GAAAAG, GAAAAU, GAAACC,
GAAACG, GAAAGA, GAAAGC, GAAAGU, GAAAUA, GAAAUC, GAAAUG, GAAAUU, GAACAA, GAACAC,
GAACAG, GAACAU, GAACCA, GAACCC, GAACCG, GAACCU, GAACGA, GAACGC, GAACGG, GAACGU,
GAACUA, GAACUG, GAACUU, GAAGAC, GAAGAG, GAAGCA, GAAGCG, GAAGCU, GAAGUC, GAAUAA,

TABLE 1-continued

Hexamers that are not seed sequences of human miRNAs

GAAUAC, GAAUAG, GAAUAU, GAAUCC, GAAUCG, GAAUCU, GAAUGA, GAAUGC, GAAUGU, GAAUUA,
GAAUUC, GAAUUU, GACAAA, GACAAG, GACAAU, GACACC, GACAGA, GACAGG, GACAUA, GACAUG,
GACAUU, GACCAA, GACCAC, GACCAG, GACCCA, GACCCC, GACCCG, GACCGC, GACCGG, GACCGU,
GACCUA, GACCUC, GACCUU, GACGAA, GACGAC, GACGAG, GACGAU, GACGCA, GACGCC, GACGCG,
GACGCU, GACGGA, GACGGC, GACGGG, GACGGU, GACGUA, GACGUC, GACGUG, GACGUU, GACUAA,
GACUAC, GACUAG, GACUAU, GACUCA, GACUCC, GACUCG, GACUGG, GACUGU, GACUUA, GACUUG,
GACUUU, GAGAAU, GAGAGA, GAGAGC, GAGAGG, GAGAUA, GAGAUC, GAGCAA, GAGCAU, GAGCCA,
GAGCGA, GAGCGG, GAGCGU, GAGGGU, GAGGUC, GAGGUG, GAGUAA, GAGUAG, GAGUCC, GAGUUC,
GAGUUU, GAUAAA, GAUAAC, GAUAAG, GAUAAU, GAUACA, GAUACC, GAUACG, GAUACU, GAUAGA,
GAUAGC, GAUAGG, GAUAGU, GAUAUA, GAUCAA, GAUCAC, GAUCAU, GAUCCA, GAUCCC, GAUCCU,
GAUCGC, GAUCGG, GAUCGU, GAUCUA, GAUCUG, GAUCUU, GAUGAA, GAUGAC, GAUGAG, GAUGCA,
GAUGCC, GAUGCG, GAUGCU, GAUGGC, GAUGGG, GAUGGU, GAUGUG, GAUGUU, GAUUAA, GAUUAC,
GAUUAG, GAUUAU, GAUUCA, GAUUCG, GAUUCU, GAUUGA, GAUUGC, GAUUUA, GAUUUC, GAUUUG,
GAUUUU, GCAAAC, GCAAAG, GCAAAU, GCAACA, GCAACC, GCAAGC, GCAAGU, GCAAUA, GCAAUC,
GCAAUG, GCAAUU, GCACAA, GCACAC, GCACAG, GCACCC, GCACCG, GCACCU, GCACGA, GCACGC,
GCACGU, GCACUA, GCACUC, GCACUG, GCACUU, GCAGAU, GCAGCC, GCAGCG, GCAGGC, GCAGUA,
GCAGUC, GCAGUG, GCAGUU, GCAUAA, GCAUAG, GCAUAU, GCAUCG, GCAUCU, GCAUGA, GCAUGC,
GCAUGG, GCAUGU, GCAUUA, GCAUUC, GCAUUG, GCAUUU, GCCAAA, GCCAAC, GCCAAU, GCCACA,
GCCACC, GCCACG, GCCAGA, GCCAGU, GCCAUA, GCCAUC, GCCAUG, GCCAUU, GCCCAA, GCCCAC,
GCCCAG, GCCCCG, GCCCGA, GCCCGG, GCCCGU, GCCGAA, GCCGAC, GCCGAG, GCCGAU, GCCGCA,
GCCGCU, GCCGGA, GCCGGC, GCCGGG, GCCGGU, GCCGUA, GCCGUC, GCCGUG, GCCGUU, GCCUAA,
GCCUAU, GCCUCA, GCCUCC, GCCUCG, GCCUGA, GCCUUA, GCCUUU, GCGAAA, GCGAAC, GCGAAG,
GCGAAU, GCGACC, GCGACG, GCGACU, GCGAGA, GCGAGC, GCGAGG, GCGAGU, GCGAUA, GCGAUC,
GCGAUG, GCGAUU, GCGCAA, GCGCAC, GCGCAG, GCGCAU, GCGCCA, GCGCCC, GCGCCU, GCGCGA,
GCGCGU, GCGCUA, GCGCUC, GCGCUG, GCGCUU, GCGGAA, GCGGAC, GCGGAU, GCGGCA, GCGGCC,
GCGGCU, GCGGGA, GCGGUA, GCGGUC, GCGGUU, GCGUAA, GCGUAC, GCGUAG, GCGUAU, GCGUCA,
GCGUCC, GCGUCG, GCGUCU, GCGUGA, GCGUGC, GCGUGG, GCGUGU, GCGUUA, GCGUUC, GCGUUG,
GCGUUU, GCUAAA, GCUAAC, GCUAAG, GCUAAU, GCUACC, GCUACG, GCUACU, GCUAGA, GCUAGG,
GCUAGU, GCUAUA, GCUAUC, GCUAUU, GCUCAA, GCUCAC, GCUCAG, GCUCAU, GCUCCA, GCUCCC,
GCUCCG, GCUCGA, GCUCGC, GCUCGU, GCUCUA, GCUCUC, GCUCUU, GCUGAA, GCUGAC, GCUGAU,
GCUGCA, GCUGCC, GCUGCG, GCUGCU, GCUGUG, GCUGUU, GCUUAC, GCUUAG, GCUUAU, GCUUCA,
GCUUCG, GCUUGA, GCUUGG, GCUUGU, GCUUUA, GCUUUG, GGAAAG, GGAACA, GGAACC, GGAACG,
GGAACU, GGAAGU, GGAAUA, GGAAUC, GGAAUU, GGACAA, GGACAC, GGACAG, GGACAU, GGACCG,
GGACGA, GGACGC, GGACGU, GGACUA, GGACUC, GGACUU, GGAGAC, GGAGCA, GGAGCG, GGAGGG,
GGAGUA, GGAUAA, GGAUAC, GGAUCA, GGAUCC, GGAUCG, GGAUCU, GGAUGC, GGAUUA, GGAUUG,
GGCAAU, GGCACA, GGCACU, GGCAGA, GGCAUA, GGCAUC, GGCCAC, GGCCAG, GGCCCC, GGCCGA,
GGCCGC, GGCCGU, GGCCUA, GGCCUG, GGCCUU, GGCGAA, GGCGAG, GGCGAU, GGCGCA, GGCGCU,
GGCGGU, GGCGUA, GGCGUC, GGCGUG, GGCGUU, GGCUAA, GGCUAC, GGCUAG, GGCUAU, GGCUCC,
GGCUCG, GGCUGA, GGCUUA, GGCUUC, GGCUUG, GGGAAU, GGGACA, GGGAGA, GGGAGU, GGGAUA,

TABLE 1-continued

Hexamers that are not seed sequences of human miRNAs

GGGAUU, GGGCAA, GGGCAC, GGGCAG, GGGCCG, GGGCGG, GGGGCC, GGGGGG, GGGGGU, GGGGUA,
GGGUAC, GGGUAU, GGGUCA, GGGUCC, GGGUCG, GGGUGA, GGGUGC, GGGUUA, GGGUUG, GGUAAA,
GGUAAC, GGUAAG, GGUAAU, GGUACA, GGUACC, GGUACG, GGUACU, GGUAGC, GGUAGG, GGUAGU,
GGUAUA, GGUAUC, GGUAUG, GGUCAA, GGUCAC, GGUCAG, GGUCAU, GGUCCA, GGUCCG, GGUCCU,
GGUCGA, GGUCGC, GGUCGG, GGUCGU, GGUCUC, GGUCUU, GGUGAA, GGUGAC, GGUGAU, GGUGCA,
GGUGCC, GGUGGC, GGUGUA, GGUGUC, GGUUAA, GGUUAG, GGUUAU, GGUUCA, GGUUCC, GGUUCG,
GGUUGC, GGUUUC, GGUUUU, GUAAAA, GUAAAG, GUAAAU, GUAACC, GUAACG, GUAACU, GUAAGA,
GUAAGC, GUAAGG, GUAAGU, GUAAUA, GUAAUC, GUAAUG, GUAAUU, GUACAA, GUACAC, GUACAG,
GUACAU, GUACCA, GUACCC, GUACCG, GUACCU, GUACGA, GUACGC, GUACGG, GUACGU, GUACUA,
GUACUC, GUACUG, GUACUU, GUAGAA, GUAGAC, GUAGCA, GUAGCC, GUAGCG, GUAGCU, GUAGGA,
GUAGGC, GUAGGG, GUAGGU, GUAGUA, GUAGUC, GUAUAA, GUAUAC, GUAUAG, GUAUAU, GUAUCA,
GUAUCG, GUAUCU, GUAUGA, GUAUGC, GUAUGG, GUAUUA, GUAUUG, GUAUUU, GUCAAA, GUCAAG,
GUCAAU, GUCACA, GUCACC, GUCACG, GUCAGA, GUCAGC, GUCAGG, GUCAUA, GUCAUC, GUCAUG,
GUCCAA, GUCCAC, GUCCAU, GUCCCC, GUCCCU, GUCCGA, GUCCGC, GUCCGG, GUCCGU, GUCCUA,
GUCCUG, GUCCUU, GUCGAA, GUCGAC, GUCGAG, GUCGAU, GUCGCA, GUCGCC, GUCGCG, GUCGCU,
GUCGGA, GUCGGC, GUCGGG, GUCGGU, GUCGUA, GUCGUC, GUCGUU, GUCUAA, GUCUAG, GUCUCA,
GUCUCC, GUCUCG, GUCUGA, GUCUGG, GUCUGU, GUCUUC, GUCUUU, GUGAAA, GUGAAC, GUGAAG,
GUGACC, GUGACG, GUGAGA, GUGAGC, GUGAGU, GUGAUC, GUGAUG, GUGAUU, GUGCAC, GUGCAU,
GUGCCC, GUGCCG, GUGCGA, GUGCGG, GUGCGU, GUGCUA, GUGCUC, GUGCUG, GUGGAG, GUGGCG,
GUGGCU, GUGGGU, GUGGUC, GUGGUG, GUGUAA, GUGUAG, GUGUCG, GUGUGA, GUGUGC, GUGUGU,
GUGUUG, GUGUUU, GUUAAA, GUUAAC, GUUAAG, GUUACA, GUUACC, GUUACG, GUUACU, GUUAGA,
GUUAGC, GUUAGU, GUUAUA, GUUAUC, GUUAUG, GUUAUU, GUUCAA, GUUCAC, GUUCAG, GUUCCA,
GUUCCG, GUUCGA, GUUCGC, GUUCGG, GUUCGU, GUUCUA, GUUCUG, GUUGAA, GUUGAC, GUUGAG,
GUUGAU, GUUGCG, GUUGCU, GUUGGA, GUUGGC, GUUGGU, GUUGUC, GUUGUG, GUUGUU, GUUUAA,
GUUUAC, GUUUAG, GUUUAU, GUUUCA, GUUUCC, GUUUCU, GUUUGA, GUUUGC, GUUUGG, GUUUGU,
GUUUUA, GUUUUC, GUUUUU, UAAAAA, UAAAAC, UAAAAG, UAAAAU, UAAACA, UAAACC, UAAACG,
UAAACU, UAAGA, UAAAGG, UAAAGU, UAAAUA, UAAAUC, UAAAUG, UAAAUU, UACAA, UAACAC,
UAACAG, UAACCA, UAACCC, UAACCG, UAACCU, UAACGA, UAACGC, UAACGG, UAACGU, UAACUA,
UAACUG, UAACUU, UAAGAG, UAAGAU, UAAGCA, UAAGCC, UAAGCG, UAAGCU, UAAGGA, UAAGGC,
UAAGGG, UAAGGU, UAAGUA, UAAGUC, UAAGUG, UAAGUU, UAAUAA, UAAUCA, UAAUCC, UAAUCG,
UAAUCU, UAAUGA, UAAUGG, UAAUGU, UAAUUA, UAAUUC, UAAUUG, UACAAC, UACAAG, UACAAU,
UACACC, UACACG, UACACU, UACAGA, UACAGC, UACAUA, UACAUC, UACAUU, UACCAA, UACCAC,
UACCAG, UACCAU, UACCCC, UACCCG, UACCCU, UACCGA, UACCGC, UACCGG, UACCGU, UACCUA,
UACCUG, UACGAA, UACGAC, UACGAG, UACGAU, UACGCA, UACGCC, UACGCG, UACGCU, UACGGC,
UACGGG, UACGGU, UACGUA, UACGUC, UACGUG, UACGUU, UACUAA, UACUAC, UACUAG, UACUAU,
UACUCA, UACUCC, UACUCG, UACUCU, UACUGA, UACUGC, UACUGG, UACUUA, UACUUG, UACUUU,
UAGAAA, UAGAAG, UAGAAU, UAGACA, UAGACG, UAGAGA, UAGAGC, UAGAGU, UAGAUA, UAGAUC,
UAGAUG, UAGCAU, UAGCCC, UAGCCG, UAGCCU, UAGCGA, UAGCGC, UAGCGU, UAGCUA, UAGCUC,
UAGCUG, UAGGAA, UAGGAU, UAGGCG, UAGGCU, UAGGGU, UAGGUC, UAGGUG, UAGGUU, UAGUAA,

TABLE 1-continued

Hexamers that are not seed sequences of human miRNAs

UAGUAC, UAGUAG, UAGUAU, UAGUCA, UAGUCG, UAGUGU, UAGUUA, UAGUUC, UAGUUG, UAGUUU,
UAUAAC, UAUAAG, UAUACU, UAUAGA, UAUAGC, UAUAGG, UAUAGU, UAUAUA, UAUAUC, UAUAUG,
UAUAUU, UAUCAA, UAUCAC, UAUCAU, UAUCCA, UAUCCC, UAUCCG, UAUCCU, UAUCGA, UAUCGC,
UAUCGG, UAUCGU, UAUCUA, UAUCUC, UAUCUG, UAUCUU, UAUGAA, UAUGAC, UAUGAG, UAUGAU,
UAUGCA, UAUGCG, UAUGCU, UAUGGA, UAUGGC, UAUGUC, UAUGUG, UAUGUU, UAUUAG, UAUUCA,
UAUUCC, UAUUCG, UAUUCU, UAUUGA, UAUUGG, UAUUUA, UAUUUC, UAUUUG, UAUUUU, UCAAAA,
UCAAAC, UCAAAG, UCAACC, UCAACU, UCAAGA, UCAAGC, UCAAUA, UCAAUC, UCAAUG, UCAAUU,
UCACCC, UCACCG, UCACCU, UCACGA, UCACGC, UCACGG, UCACGU, UCACUA, UCACUC, UCACUU,
UCAGAA, UCAGAC, UCAGAG, UCAGCG, UCAGCU, UCAGGA, UCAGGC, UCAGGU, UCAGUC, UCAGUU,
UCAUAA, UCAUCA, UCAUCC, UCAUCG, UCAUGC, UCAUGG, UCAUGU, UCAUUA, UCAUUG, UCCAAA,
UCCAAC, UCCAAG, UCCAAU, UCCACA, UCCACC, UCCACG, UCCAGC, UCCAGG, UCCAUA, UCCAUC,
UCCAUU, UCCCAA, UCCCAG, UCCCAU, UCCCCC, UCCCCG, UCCCCU, UCCCGA, UCCCGC, UCCCGG,
UCCCGU, UCCCUA, UCCCUC, UCCGAA, UCCGAC, UCCGAG, UCCGAU, UCCGCA, UCCGCC, UCCGGA,
UCCGGC, UCCGGU, UCCGUA, UCCGUC, UCCGUG, UCCUAA, UCCUCA, UCCUCG, UCCUCU, UCCUGC,
UCCUGU, UCCUUA, UCCUUC, UCCUUU, UCGAAA, UCGAAC, UCGAAG, UCGAAU, UCGACA, UCGACC,
UCGACG, UCGACU, UCGAGA, UCGAGC, UCGAGG, UCGAUA, UCGAUC, UCGAUG, UCGAUU, UCGCAA,
UCGCAC, UCGCAG, UCGCAU, UCGCCA, UCGCCC, UCGCCG, UCGCCU, UCGCGA, UCGCGC, UCGCGU,
UCGCUA, UCGCUC, UCGGAA, UCGGAC, UCGGAG, UCGGAU, UCGGCA, UCGGCU, UCGGGG, UCGGGU,
UCGGUC, UCGGUG, UCGGUU, UCGUAA, UCGUAC, UCGUAG, UCGUAU, UCGUCA, UCGUCC, UCGUCG,
UCGUCU, UCGUGA, UCGUGU, UCGUUA, UCGUUC, UCGUUG, UCGUUU, UCUAAC, UCUAAG, UCUAAU,
UCUACA, UCUACC, UCUACG, UCUACU, UCUAGC, UCUAGG, UCUAGU, UCUAUA, UCUAUC, UCUAUG,
UCUAUU, UCUCAG, UCUCAU, UCUCCG, UCUCGC, UCUCGG, UCUCGU, UCUCUC, UCUGAA, UCUGAU,
UCUGCA, UCUGCG, UCUGCU, UCUGGC, UCUGGU, UCUGUC, UCUGUG, UCUGUU, UCUUAA, UCUUAC,
UCUUAG, UCUUAU, UCUUCA, UCUUCC, UCUUCG, UCUUCU, UCUUGC, UCUUGG, UCUUGU, UCUUUA,
UCUUUC, UCUUUG, UCUUUU, UGAAAA, UGAAAC, UGAACA, UGAACC, UGAAGG, UGAAUC, UGAAUG,
UGACAA, UGACAC, UGACAG, UGACCA, UGACCC, UGACCG, UGACGA, UGACGC, UGACGG, UGACGU,
UGACUA, UGACUC, UGACUU, UGAGAG, UGAGAU, UGAGCA, UGAGCC, UGAGCU, UGAGGC, UGAGGU,
UGAGUA, UGAGUU, UGAUAC, UGAUAG, UGAUAU, UGAUCA, UGAUCG, UGAUCU, UGAUGA, UGAUGC,
UGAUGG, UGAUGU, UGAUUA, UGAUUC, UGAUUG, UGAUUU, UGCAAC, UGCAAG, UGCACA, UGCACG,
UGCAGG, UGCAGU, UGCAUC, UGCCCA, UGCCCC, UGCCCG, UGCCGA, UGCCGC, UGCCGG, UGCCGU,
UGCCUA, UGCCUC, UGCCUG, UGCCUU, UGCGAA, UGCGAC, UGCGAU, UGCGCC, UGCGCG, UGCGCU,
UGCGGC, UGCGGG, UGCGGU, UGCGUA, UGCGUC, UGCGUG, UGCGUU, UGCUAC, UGCUAU, UGCUCC,
UGCUCG, UGCUGC, UGCUGG, UGCUGU, UGCUUA, UGCUUU, UGGAAC, UGGAAG, UGGAGC, UGGAUC,
UGGAUU, UGGCAA, UGGCAC, UGGCAG, UGGCCG, UGGCCU, UGGCGA, UGGCGC, UGGCGU, UGGCUA,
UGGCUC, UGGCUU, UGGGAA, UGGGCA, UGGGCC, UGGGGC, UGGGUC, UGGUAA, UGGUAG, UGGUAU,
UGGUCC, UGGUCG, UGGUCU, UGGUGA, UGGUGC, UGGUGG, UGGUGU, UGGUUA, UGGUUG, UGUAAA,
UGUAAC, UGUAAG, UGUACC, UGUACG, UGUACU, UGUAGA, UGUAGC, UGUAGU, UGUAUC, UGUAUU,
UGUCAA, UGUCAC, UGUCAG, UGUCAU, UGUCCA, UGUCCC, UGUCCG, UGUCGA, UGUCGC, UGUCGG,
UGUCGU, UGUCUA, UGUCUC, UGUGAC, UGUGAG, UGUGAU, UGUGCA, UGUGGU, UGUGUA, UGUGUU,

TABLE 1-continued

Hexamers that are not seed sequences of human miRNAs

UGUUAC, UGUUAG, UGUUAU, UGUUCA, UGUUCC, UGUUCG, UGUUGG, UGUUGU, UGUUUA, UGUUUC, UGUUUG, UGUUUU, UUAAAA, UUAAAC, UUAAAG, UUAAAU, UUAACC, UUAACG, UUAACU, UUAAGU, UUAAUA, UUAAUC, UUAAUG, UUAAUU, UUACAA, UUACAC, UUACAG, UUACAU, UUACCA, UUACCC, UUACCG, UUACCU, UUACGA, UUACGC, UUACGG, UUACGU, UUACUA, UUACUC, UUACUG, UUACUU, UUAGAA, UUAGAC, UUAGCC, UUAGCG, UUAGCU, UUAGGC, UUAGGU, UUAGUA, UUAGUC, UUAGUU, UUAUAA, UUAUAC, UUAUAG, UUAUAU, UUAUCC, UUAUCG, UUAUCU, UUAUGA, UUAUGG, UUAUGU, UUAUUA, UUAUUC, UUAUUG, UUAUUU, UUCAAC, UUCAAU, UUCACA, UUCACC, UUCACG, UUCACU, UUCAGC, UUCAGG, UUCAGU, UUCAUA, UUCAUC, UUCAUG, UUCAUU, UUCCAA, UUCCCA, UUCCCG, UUCCGA, UUCCGU, UUCCUU, UUCGAA, UUCGAC, UUCGAG, UUCGAU, UUCGCA, UUCGCC, UUCGCG, UUCGCU, UUCGGA, UUCGGC, UUCGGG, UUCGGU, UUCGUA, UUCGUC, UUCGUG, UUCGUU, UUCUAC, UUCUAG, UUCUCA, UUCUCG, UUCUGG, UUCUUA, UUCUUU, UUGAAA, UUGAAC, UUGAAG, UUGAAU, UUGACC, UUGACG, UUGACU, UUGAGA, UUGAGC, UUGAGU, UUGAUA, UUGAUC, UUGAUG, UUGAUU, UUGCAA, UUGCAC, UUGCAG, UUGCAU, UUGCCC, UUGCCG, UUGCGA, UUGCGC, UUGCGG, UUGCGU, UUGCUA, UUGCUC, UUGCUG, UUGCUU, UUGGAA, UUGGAG, UUGGCC, UUGGCG, UUGGCU, UUGGGC, UUGGGU, UUGGUA, UUGGUG, UUGUAA, UUGUAC, UUGUCA, UUGUCG, UUGUCU, UUGUGC, UUGUGG, UUGUUA, UUGUUG, UUGUUU, UUUAAA, UUUAAC, UUUAAG, UUUAAU, UUUACA, UUUACC, UUUACG, UUUACU, UUUAGA, UUUAGC, UUUAGG, UUUAGU, UUUAUA, UUUAUC, UUUAUG, UUUAUU, UUUCAU, UUUCCA, UUUCCG, UUUCCU, UUUCGA, UUUCGC, UUUCGG, UUUCGU, UUUCUA, UUUCUC, UUUCUG, UUUCUU, UUUGAA, UUUGAC, UUUGAG, UUUGAU, UUUGCC, UUUGCU, UUUGGA, UUUGGC, UUUGGG, UUUGGU, UUUGUA, UUUGUC, UUUGUU, UUUUAA, UUUUAG, UUUUAU, UUUUCC, UUUUCG, UUUUCU, UUUUGA, UUUUGC, UUUUGG, UUUUGU, UUUUUA, UUUUUC, UUUUUU

TABLE 2

A listing of oligonucleotide modifications.

| Symbol | Feature Description |
|---|---|
| bio | 5' biotin |
| dAs | DNA w/3'thiophosphate |
| dCs | DNA w/3'thiophosphate |
| dGs | DNA w/3'thiophosphate |
| dTs | DNA w/3'thiophosphate |
| dG | DNA w/3'phosphate |
| dT | DNA w/3'phosphate |
| dU | deoxyuridine w/3'phosphate |
| d5mCs | deoxy-5-methylcytidine w/3'thiophosphate |
| enaAs | ENA w/3'thiophosphate |
| enaCs | ENA w/3'thiophosphate |
| enaGs | ENA w/3'thiophosphate |
| enaTs | ENA w/3'thiophosphate |
| fluAs | 2'-fluoro w/3'thiophosphate |
| fluCs | 2'-fluoro w/3'thiophosphate |
| fluGs | 2'-fluoro w/3'thiophosphate |
| fluUs | 2'-fluoro w/3'thiophosphate |
| lnaAs | LNA w/3'thiophosphate |
| lnaCs | LNA w/3'thiophosphate |
| lnaGs | LNA w/3'thiophosphate |
| lnaTs | LNA w/3'thiophosphate |
| omeAs | 2'-OMe w/3'thiophosphate |
| omeCs | 2'-OMe w/3'thiophosphate |
| omeGs | 2'-OMe w/3'thiophosphate |
| omeTs | 2'-OMe w/3'thiophosphate |
| lnaAs-Sup | LNA w/3'thiophosphate at 3'terminus |
| lnaCs-Sup | LNA w/3'thiophosphate at 3'terminus |
| lnaGs-Sup | LNA w/3'thiophosphate at 3'terminus |
| lnaTs-Sup | LNA w/3'thiophosphate at 3'terminus |
| lnaA-Sup | LNA w/3'OH at 3'terminus |
| lnaC-Sup | LNA w/3'OH at 3'terminus |
| lnaG-Sup | LNA w/3'OH at 3'terminus |
| lnaT-Sup | LNA w/3'OH at 3'terminus |
| omeA-Sup | 2'-OMe w/3'OH at 3'terminus |
| omeC-Sup | 2'-OMe w/3'OH at 3'terminus |
| omeG-Sup | 2'-OMe w/3'OH at 3'terminus |
| omeU-Sup | 2'-OMe w/3'OH at 3'terminus |
| dAs-Sup | DNA w/3'thiophosphate at 3'terminus |
| dCs-Sup | DNA w/3'thiophosphate at 3'terminus |
| dGs-Sup | DNA w/3'thiophosphate at 3'terminus |
| dTs-Sup | DNA w/3'thiophosphate at 3'terminus |
| dA-Sup | DNA w/3'OH at 3'terminus |
| dC-Sup | DNA w/3'OH at 3'terminus |
| dG-Sup | DNA w/3'OH at 3'terminus |
| dT-Sup | DNA w/3'OH at 3'terminus |
| dU | deoxyuridine w/3'OH at 3'terminus |
| rA | RNA w/3'phosphate |
| rC | RNA w/3'phosphate |
| rG | RNA w/3'phosphate |
| rU | RNA w/3'phosphate |

TABLE 3

Formatted oligonucleotide sequences made for testing in the lab showing nucleotide modifications.

| OligoID | Base Sequence | Formatted Sequence | SeqID |
|---|---|---|---|
| HBB-01 G7A m01 | GCTATTACCTTAACC CAG | InaGs; omeCs; InaTs; omeAs; InaTs; omeUs; InaAs; omeCs; InaCs; omeUs; InaTs; omeAs; InaAs; omeCs; InaCs; omeCs; InaAs; omeG-Sup | 3789 |
| HBB-02 m01 | GCTATTACCTTAACC | InaGs; omeCs; InaTs; omeAs; InaTs; omeUs; InaAs; omeCs; InaCs; omeUs; InaTs; omeAs; InaAs; omeCs; InaC-Sup | 3790 |
| HBB-03 m01 | CTATTACCTTAACCC | InaCs; omeUs; InaAs; omeUs; InaTs; omeAs; InaCs; omeCs; InaTs; omeUs; InaAs; omeAs; InaCs; omeCs; InaC-Sup | 3791 |
| HBB-04 m01 | TATTACCTTAACCCA | InaTs; omeAs; InaTs; omeUs; InaAs; omeCs; InaCs; omeUs; InaTs; omeAs; InaAs; omeCs; InaCs; omeCs; InaA-Sup | 3792 |
| HBB-05 m01 | ATTACCTTAACCCAG | InaAs; omeUs; InaTs; omeAs; InaCs; omeCs; InaTs; omeUs; InaAs; omeAs; InaCs; omeCs; InaCs; omeAs; InaG-Sup | 3793 |
| HBB-06 705 control m01 | CCTCTTACCTCAGTT ACA | InaCs; omeCs; InaTs; omeCs; InaTs; omeUs; InaAs; omeCs; InaCs; omeUs; InaCs; omeAs; InaGs; omeUs; InaTs; omeAs; InaCs; omeA-Sup | 3794 |
| HBB-01_G7A m01 | GCTATTACCTTAACC CAG | InaGs; omeCs; InaTs; omeAs; InaTs; omeUs; InaAs; omeCs; InaCs; omeUs; InaTs; omeAs; InaAs; omeCs; InaCs; omeCs; InaAs; omeG-Sup | 3789 |
| HBB-06 705 control m02 + bioTEGs + heg | CCTCTTACCTCAGTT ACA | InaCs; omeCs; InaTs; omeCs; InaTs; omeUs; InaAs; omeCs; InaCs; omeUs; InaCs; omeAs; InaGs; omeUs; InaTs; omeAs; InaCs; omeA-Sup | 3794 |
| HBB-01_G7A m01 | GCTATTACCTTAACC CAG | InaGs; omeCs; InaTs; omeAs; InaTs; omeUs; InaAs; omeCs; InaCs; omeUs; InaTs; omeAs; InaAs; omeCs; InaCs; omeCs; InaAs; omeG-Sup | 3789 |
| HBB-01_G7A dimer m1000 | GCTATTACCTTAACC CAGTTTTGCTATTAC CTTAACCCAG | InaGs; omeCs; InaTs; omeAs; InaTs; omeUs; InaAs; omeCs; InaCs; omeUs; InaTs; omeAs; InaAs; omeCs; InaCs; omeCs; InaAs; omeG; dT; dT; dT; dT; InaGs; omeCs; InaTs; omeAs; InaTs; omeUs; InaAs; omeCs; InaCs; omeCs; InaAs; omeG-Sup | 3795 |
| HBB-06 705 control m1000 | CCTCTTACCTCAGTT ACA | InaCs; omeCs; InaTs; omeCs; InaTs; omeUs; InaAs; omeCs; InaCs; omeUs; InaCs; omeAs; InaGs; omeUs; InaTs; omeAs; InaCs; omeA-Sup | 3794 |
| HBB-06 705 control dimer m1000 | CCTCTTACCTCAGTT ACATTTTCCTCTTAC CTCAGTTACA | InaCs; omeCs; InaTs; omeCs; InaTs; omeUs; InaAs; omeCs; InaCs; omeUs; InaCs; omeAs; InaGs; omeUs; InaTs; omeAs; InaCs; omeA; dT; dT; dT; dT; InaCs; omeCs; InaTs; omeCs; InaTs; omeUs; InaAs; omeCs; InaCs; omeUs; InaCs; omeAs; InaGs; omeUs; InaTs; omeAs; InaCs; omeA-Sup | 3796 |
| HBB-28 m08 | ACTTTTATGCCCAGC | InaAs; InaCs; InaTs; dTs; dTs; dTs; dAs; dTs; dGs; dCs; dCs; dCs; InaAs; InaGs; InaC-Sup | 3797 |
| HBB-29 m08 | TTTTATGCCCAGCCC | InaTs; InaTs; InaTs; dTs; dAs; dTs; dGs; dCs; dCs; dCs; dAs; dGs; InaCs; InaCs; InaC-Sup | 3798 |
| HBB-30 m08 | GTAGATTGGCCAACC | InaGs; InaTs; InaAs; dGs; dAs; dTs; dTs; dGs; dGs; dCs; dCs; dAs; InaAs; InaCs; InaC-Sup | 3799 |
| HBB-31 m08 | TAGATTGGCCAACCC | InaTs; InaAs; InaGs; dAs; dTs; dTs; dGs; dGs; dCs; dCs; dAs; dAs; InaCs; InaCs; InaC-Sup | 3800 |
| HBB-32 m08 | GATTGGCCAACCCTA | InaGs; InaAs; InaTs; dTs; dGs; dGs; dCs; dCs; dAs; dAs; dCs; dCs; InaCs; InaTs; InaA-Sup | 3801 |

TABLE 3-continued

Formatted oligonucleotide sequences made for testing
in the lab showing nucleotide modifications.

| OligoID | Base Sequence | Formatted Sequence | SeqID |
|---|---|---|---|
| HBB-33 m08 | ATTGGCCAACCCTAG | InaAs; InaTs; InaTs; dGs; dGs; dCs; dCs; dAs; dAs; dCs; dCs; dCs; InaTs; InaAs; InaG-Sup | 3802 |
| HBB-34 m08 | TGATGACAGCCGTAC | InaTs; InaGs; InaAs; dTs; dGs; dAs; dCs; dAs; dGs; dCs; dCs; dGs; InaTs; InaAs; InaC-Sup | 3803 |
| HBB-35 m08 | CAGCCGTACCTGTCC | InaCs; InaAs; InaGs; dCs; dCs; dGs; dTs; dAs; dCs; dCs; dTs; dGs; InaTs; InaCs; InaC-Sup | 3804 |
| HBB-36 m08 | CCGTACCTGTCCTTG | InaCs; InaCs; InaGs; dTs; dAs; dCs; dCs; dTs; dGs; dTs; dCs; dCs; InaTs; InaTs; InaG-Sup | 3805 |
| HBB-37 m08 | CGTACCTGTCCTTGG | InaCs; InaGs; InaTs; dAs; dCs; dCs; dTs; dGs; dTs; dCs; dCs; dTs; InaTs; InaGs; InaG-Sup | 3806 |
| HBB-38 m08 | TTCTGGCACTGGCTT | InaTs; InaTs; InaCs; dTs; dGs; dGs; dCs; dAs; dCs; dTs; dGs; dGs; InaCs; InaTs; InaT-Sup | 3807 |
| HBB-39 m08 | GCACTGGCTTAGGAG | InaGs; InaCs; InaAs; dCs; dTs; dGs; dGs; dCs; dTs; dTs; dAs; dGs; InaGs; InaAs; InaG-Sup | 3808 |
| HBB-40 m08 | GCTCTTCTGGCACTG GCTTAGGAGT | InaGs; InaCs; InaTs; dCs; dTs; dTs; dCs; dTs; dGs; dGs; dCs; dAs; dCs; dTs; dGs; dGs; dCs; dTs; dTs; dAs; dGs; dGs; InaAs; InaGs; InaT-Sup | 3809 |
| HBB-41 m08 | TCTGGCACTGGCTTA GGAGTTGGAC | InaTs; InaCs; InaTs; dGs; dGs; dCs; dAs; dCs; dTs; dGs; dGs; dCs; dTs; dTs; dAs; dGs; dGs; dAs; dGs; dTs; dTs; dGs; InaGs; InaAs; InaC-Sup | 3810 |
| HBB-42 m08 | GCACTGGCTTAGGAG TTGGACTTCA | InaGs; InaCs; InaAs; dCs; dTs; dGs; dGs; dCs; dTs; dTs; dAs; dGs; dGs; dAs; dGs; dTs; dTs; dGs; dGs; dAs; dCs; dTs; InaTs; InaCs; InaA-Sup | 3811 |
| HBB-43 m08 | ATCGTTTTCCCAATT | InaAs; InaTs; InaCs; dGs; dTs; dTs; dTs; dTs; dCs; dCs; dCs; dAs; InaAs; InaTs; InaT-Sup | 3812 |
| HBB-44 m08 | AAAACTCTACCTCGG | InaAs; InaAs; InaAs; dAs; dCs; dTs; dCs; dTs; dAs; dCs; dCs; dTs; InaCs; InaGs; InaG-Sup | 3813 |
| HBB-45 m08 | ACCTCGGTTCTAAGC | InaAs; InaCs; InaCs; dTs; dCs; dGs; dGs; dTs; dTs; dCs; dTs; dAs; InaAs; InaGs; InaC-Sup | 3814 |
| HBB-46 m08 | GCTCTGTGCATTAGT | InaGs; InaCs; InaTs; dCs; dTs; dGs; dTs; dGs; dCs; dAs; dTs; dTs; InaAs; InaGs; InaT-Sup | 3815 |
| HBB-47 m08 | AATAGGAGGTTAACT | InaAs; InaAs; InaTs; dAs; dGs; dGs; dAs; dGs; dGs; dTs; dTs; dAs; InaAs; InaCs; InaT-Sup | 3816 |
| HBB-48 m08 | GGTCTTCTACTTGGC | InaGs; InaGs; InaTs; dCs; dTs; dTs; dCs; dTs; dAs; dCs; dTs; dTs; InaGs; InaGs; InaC-Sup | 3817 |
| HBB-49 m08 | GCTGCAAGCTATACT | InaGs; InaCs; InaTs; dGs; dCs; dAs; dAs; dGs; dCs; dTs; dAs; dTs; InaAs; InaCs; InaT-Sup | 3818 |
| HBB-50 m08 | GGTGCAGGTCTATTC | InaGs; InaGs; InaTs; dGs; dCs; dAs; dGs; dGs; dTs; dCs; dTs; dAs; InaTs; InaTs; InaC-Sup | 3819 |

TABLE 3-continued

Formatted oligonucleotide sequences made for testing
in the lab showing nucleotide modifications.

| OligoID | Base Sequence | Formatted Sequence | SeqID |
|---|---|---|---|
| HBB-51 m08 | CCTCTAAGTATACCC | InaCs; InaCs; InaTs; dCs; dTs; dAs; dAs; dGs; dTs; dAs; dTs; dAs; InaCs; InaCs; InaC-Sup | 3820 |
| HBB-52 m08 | GCTTGACCTAGGAAC | InaGs; InaCs; InaTs; dTs; dGs; dAs; dCs; dCs; dTs; dAs; dGs; dGs; InaAs; InaAs; InaC-Sup | 3821 |
| HBB-53 m08 | AACCAGAACCCATAG | InaAs; InaAs; InaCs; dCs; dAs; dGs; dAs; dAs; dCs; dCs; dCs; dAs; InaTs; InaAs; InaG-Sup | 3822 |
| HBB-54 m08 | GAAACAAACCGCACA | InaGs; InaAs; InaAs; dAs; dCs; dAs; dAs; dAs; dCs; dCs; dGs; dCs; InaAs; InaCs; InaA-Sup | 3823 |
| HBB-55 m08 | CGAATACCACACAAG | InaCs; InaGs; InaAs; dAs; dTs; dAs; dCs; dCs; dAs; dCs; dAs; dCs; InaAs; InaAs; InaG-Sup | 3824 |
| HBB-56 m08 | TACTTGTGACCTCTC | InaTs; InaAs; InaCs; dTs; dTs; dGs; dTs; dGs; dAs; dCs; dCs; dTs; InaCs; InaTs; InaC-Sup | 3825 |
| HBB-57 m08 | CTATACCCCATCAAG | InaCs; InaTs; InaAs; dTs; dAs; dCs; dCs; dCs; dCs; dAs; dTs; dCs; InaAs; InaAs; InaG-Sup | 3826 |
| HBB-58 m08 | GTTGGAGTTTAATCG | InaGs; InaTs; InaTs; dGs; dGs; dAs; dGs; dTs; dTs; dTs; dAs; dAs; InaTs; InaCs; InaG-Sup | 3827 |
| HBB-59 m08 | TTGGAGTTTAATCGT | InaTs; InaTs; InaGs; dGs; dAs; dGs; dTs; dTs; dTs; dAs; dAs; dTs; InaCs; InaGs; InaT-Sup | 3828 |
| HBB-60 m08 | GGAGTTTAATCGTAG | InaGs; InaGs; InaAs; dGs; dTs; dTs; dTs; dAs; dAs; dTs; dCs; dGs; InaTs; InaAs; InaG-Sup | 3829 |
| HBB-61 m08 | GAGTTTAATCGTAGC | InaGs; InaAs; InaGs; dTs; dTs; dTs; dAs; dAs; dTs; dCs; dGs; dTs; InaAs; InaGs; InaC-Sup | 3830 |
| HBB-62 m08 | AGTTTAATCGTAGCA | InaAs; InaGs; InaTs; dTs; dTs; dAs; dAs; dTs; dCs; dGs; dTs; dAs; InaGs; InaCs; InaA-Sup | 3831 |
| HBB-63 m08 | GTTTAATCGTAGCAT | InaGs; InaTs; InaTs; dTs; dAs; dAs; dTs; dCs; dGs; dTs; dAs; dGs; InaCs; InaAs; InaT-Sup | 3832 |
| HBB-64 m08 | TTAATCGTAGCATTA | InaTs; InaTs; InaAs; dAs; dTs; dCs; dGs; dTs; dAs; dGs; dCs; dAs; InaTs; InaTs; InaA-Sup | 3833 |
| HBB-65 m08 | TAATCGTAGCATTAC | InaTs; InaAs; InaAs; dTs; dCs; dGs; dTs; dAs; dGs; dCs; dAs; dTs; InaTs; InaAs; InaC-Sup | 3834 |
| HBB-65 m08 | AATCGTAGCATTACC | InaAs; InaAs; InaTs; dCs; dGs; dTs; dAs; dGs; dCs; dAs; dTs; dTs; InaAs; InaCs; InaC-Sup | 3835 |
| HBB-67 m08 | ATCGTAGCATTACCC | InaAs; InaTs; InaCs; dGs; dTs; dAs; dGs; dCs; dAs; dTs; dTs; dAs; InaCs; InaCs; InaC-Sup | 3836 |
| HBB-68 m08 | CGTAGCATTACCCTT | InaCs; InaGs; InaTs; dAs; dGs; dCs; dAs; dTs; dTs; dAs; dCs; dCs;l naCs; InaTs; InaT-Sup | 3837 |
| HBB-69 m08 | GTAGCATTACCCTTG | InaGs; InaTs; InaAs; dGs; dCs; dAs; dTs; dTs; dAs; dCs; dCs; dCs; InaTs; InaTs; InaG-Sup | 3838 |

TABLE 3-continued

Formatted oligonucleotide sequences made for testing in the lab showing nucleotide modifications.

| OligoID | Base Sequence | Formatted Sequence | SeqID |
|---|---|---|---|
| HBB-70 m08 | GTTGAGGTCTTCCCT | InaGs; InaTs; InaTs; dGs; dAs; dGs; dGs; dTs; dCs; dTs; dTs; dCs; InaCs; InaCs; InaT-Sup | 3839 |
| HBB-71 m08 | TTAATGCCTTGTACG | InaTs; InaTs; InaAs; dAs; dTs; dGs; dCs; dCs; dTs; dTs; dGs; dTs; InaAs; InaCs; InaG-Sup | 3840 |
| HBB-72 m08 | TAATGCCTTGTACGG | InaTs; InaAs; InaAs; dTs; dGs; dCs; dCs; dTs; dTs; dGs; dTs; dAs; InaCs; InaGs; InaG-Sup | 3841 |
| HBB-73 m08 | TGCCTTGTACGGTTC | InaTs; InaGs; InaCs; dCs; dTs; dTs; dGs; dTs; dAs; dCs; dGs; dGs; InaTs; InaTs; InaC-Sup | 3842 |
| HBB-74 m08 | GCCTTGTACGGTTCC | InaGs; InaCs; InaCs; dTs; dTs; dGs; dTs; dAs; dCs; dGs; dGs; dTs; InaTs; InaCs; InaC-Sup | 3843 |
| HBB-75 m08 | CCTTGTACGGTTCCC | InaCs; InaCs; InaTs; dTs; dGs; dTs; dAs; dCs; dGs; dGs; dTs; dTs; InaCs; InaCs; InaC-Sup | 3844 |
| HBB-76 m08 | CTTGTACGGTTCCCT | InaCs; InaTs; InaTs; dGs; dTs; dAs; dCs; dGs; dGs; dTs; dTs; dCs; InaCs; InaCs; InaT-Sup | 3845 |
| HBB-77 m08 | TGTACGGTTCCCTTG | InaTs; InaGs; InaTs; dAs; dCs; dGs; dGs; dTs; dTs; dCs; dCs; dCs; InaTs; InaTs; InaG-Sup | 3846 |
| HBB-78 m08 | GTACGGTTCCCTTGC | InaGs; InaTs; InaAs; dCs; dGs; dGs; dTs; dTs; dCs; dCs; dCs; dTs; InaTs; InaGs; InaC-Sup | 3847 |
| HBB-79 m08 | CAAGTGCTCCCTATC | InaCs; InaAs; InaAs; dGs; dTs; dGs; dCs; dTs; dCs; dCs; dCs; dTs; InaAs; InaTs; InaC-Sup | 3848 |
| HBB-80 m08 | GCTCCCTATCTGTAG | InaGs; InaCs; InaTs; dCs; dCs; dCs; dTs; dAs; dTs; dCs; dTs; dGs; InaTs; InaAs; InaG-Sup | 3849 |
| HBB-07 m13 | GCCATCTATTGCTTACATT | rG; rC; rC; rA; rU; rC; rU; rA; rU; rU; rG; rC; rU; rU; rA7C; rA; rU; rU; dU; dU-Sup | 3850 |
| HBB-08 m13 | CCATCTATTGCTTACATTT | rC; rC; rA; rU; rC; rU; rA; rU; rU; rG; rC; rU; rU; rA7C; rA; rU; rU; rU; dU; dU-Sup | 3851 |
| HBB-09 m13 | CATCTATTGCTTACATTTG | rC; rA; rU; rC; rU; rA; rU; rU; rG; rC; rU; rU; rA; rC; rA; rU; rU; rU; rG; dU; dU-Sup | 3852 |
| HBB-10 m13 | ATCTATTGCTTACATTTGC | rA; rU; rC; rU; rA; rU; rU; rG; rC; rU; rU; rA; rC; rA; rU; rU; rU; rG; rC; dU; dU-Sup | 3853 |
| HBB-11 m13 | TCTATTGCTTACATTTGCT | rU; rC; rU; rA; rU; rU; rG; rC; rU; rU; rA; rC; rA; rU; rU; rU; rG; rC; rU; dU; dU-Sup | 3854 |
| HBB-12 m13 | CTATTGCTTACATTTGCTT | rC; rU; rA; rU; rU; rG; rC; rU; rU; rA; rC; rA; rU; rU; rU; rG; rC; rU; rU; dU; dU-Sup | 3855 |
| HBB-13 m13 | TATTGCTTACATTTGCTTC | rU; rA; rU; rU; rG; rC; rU; rU; rA; rC; rA; rU; rU; rU; rG; rC; rU; rU; rC; dU; dU-Sup | 3856 |
| HBB-14 m13 | ATTGCTTACATTTGCTTCT | rA; rU; rU; rG; rC; rU; rU; rA; rC; rA; rU; rU; rU; rG; rC; rU; rU; rC; rU; dU; dU-Sup | 3857 |

TABLE 3-continued

Formatted oligonucleotide sequences made for testing
in the lab showing nucleotide modifications.

| OligoID | Base Sequence | Formatted Sequence | SeqID |
|---|---|---|---|
| HBB-15 m13 | TTGCTTACATTTGCT TCTG | rU; rU; rG; rC; rU; rU; rA; rC; rA; rU; rU; rU; rG; rC; rU; rU; rC; rU; rG; dU; dU-Sup | 3858 |
| HBB-16 m13 | TGCTTACATTTGCTT CTGA | rU; rG; rC; rU; rU; rA; rC; rA; rU; rU; rU; rG; rC; rU; rU; rC; rU; rG; rA; dU; dU-Sup | 3859 |
| HBB-17 m13 | GCTTACATTTGCTTC TGAC | rG; rC; rU; rU; rA; rC; rA; rU; rU; rU; rG; rC; rU; rU; rC; rU; rG; rA; rC; dU; dU-Sup | 3860 |
| HBB-18 m13 | CTTACATTTGCTTCT GACA | rC; rU; rU; rA; rC; rA; rU; rU; rU; rG; rC; rU; rU; rC; rU; rG; rA; rC; rA; dU; dU-Sup | 3861 |
| HBB-19 m13 | TTACATTTGCTTCTG ACAC | rU; rU; rA; rC; rA; rU; rU; rU; rG; rC; rU; rU; rC; rU; rG; rA; rC; rA; rC; dU; dU-Sup | 3862 |
| HBB-20 m13 | TACATTTGCTTCTGA CACA | rU; rA; rC; rA; rU; rU; rU; rG; rC; rU; rU; rC; rU; rG; rA7C; rA; rC; rA; dU; dU-Sup | 3863 |
| HBB-21 m13 | ACATTTGCTTCTGAC ACAA | rA; rC; rA; rU; rU; rU; rG; rC; rU; rU; rC; rU; rG; rA; rC; rA; rC; rA; rA; dU; dU-Sup | 3864 |
| HBB-22 m13 | CATTTGCTTCTGACA CAAC | rC; rA; rU; rU; rU; rG; rC; rU; rU; rC; rU; rG; rA; rC; rA7C; rA; rA; rC; dU; dU-Sup | 3865 |
| HBB-23 m13 | ATTTGCTTCTGACAC AACT | rA; rU; rU; rU; rG; rC; rU; rU; rC; rU; rG; rA; rC; rA; rC; rA; rA; rC; rU; dU; dU-Sup | 3866 |
| HBB-24 m13 | TTTGCTTCTGACACA ACTG | rU; rU; rU; rG; rC; rU; rU; rC; rU; rG; rA; rC; rA7C; rA; rA; rC; rU; rG; dU; dU-Sup | 3867 |
| HBB-25 m13 | TTGCTTCTGACACAA CTGT | rU; rU; rG; rC; rU; rU; rC; rU; rG; rA; rC; rA; rC; rA; rA; rC; rU; rG; rU; dU; dU-Sup | 3868 |
| HBB-26 m13 | TGCTTCTGACACAAC TGTG | rU; rG; rC; rU; rU; rC; rU; rG; rA; rC; rA; rC; rA; rA; rC; rU; rG; rU; rG; dU; dU-Sup | 3869 |
| HBB-27 m13 | CACAACTGTGTTCAC TAGC | rC; rA; rC; rA; rA; rC; rU; rG; rU; rG; rU; rU; rC; rA; rC; rU; rA; rG; rC; dU; dU-Sup | 3870 |
| HBG2-01 m13 | AGGGCAAAGAACAGG TGGG | rA; rG; rG; rG; rC; rA; rA; rA; rG; rA; rA; rC; rA; rG; rG; rU; rG; rG; rG; dU; dU-Sup | 3871 |
| HBG2-02 m13 | GGCAAAGAACAGGTG GAA | rG; rG; rC; rA; rA; rA; rG; rA; rA; rC; rA; rG; rG; rU; rG; rG; rA; rA; dU; dU-Sup | 3872 |
| HBG2-03 m13 | GCAAAGAACAGGTGG GAAT | rG; rC; rA; rA; rA; rG; rA; rA; rC; rA; rG; rG; rU; rG; rG; rG; rA; rA; rU; dU; dU-Sup | 3873 |
| HBG2-04 m13 | AGAACAGGTGGGAAT GTAT | rA; rG; rA; rA; rC; rA; rG; rG; rU; rG; rG; rG; rA; rA; rU; rG; rU; rA; rU; dU; dU-Sup | 3874 |
| HBG2-05 m13 | GGGAATGTATCCAGA GAAT | rG; rG; rG; rA; rA; rU; rG; rU; rA; rU; rC; rC; rA; rG; rA; rG; rA; rA; rU; dU; dU-Sup | 3875 |
| HBG2-06 m13 | GGAATGTATCCAGAG AATC | rG; rG; rA; rA; rU; rG; rU; rA; rU; rC; rC; rA; rG; rA; rG; rA; rA; rU; rC; dU; dU-Sup | 3876 |

TABLE 3-continued

Formatted oligonucleotide sequences made for testing
in the lab showing nucleotide modifications.

| OligoID | Base Sequence | Formatted Sequence | SeqID |
|---|---|---|---|
| HBG2-07 m13 | GAATGTATCCAGAGAATCA | rG; rA; rA; rU; rG; rU; rA; rU; rC; rC; rA; rG; rA; rG; rA; rA; rU; rC; rA; dU; dU-Sup | 3877 |
| HBG2-08 m13 | AATGTATCCAGAGAATCAA | rA; rA; rU; rG; rU; rA; rU; rC; rC; rA; rG; rA; rG; rA; rA; rU; rC; rA; rA; dU; dU-Sup | 3878 |
| HBG2-09 m13 | ATGTATCCAGAGAATCAAC | rA; rU; rG; rU; rA; rU; rC; rC; rA; rG; rA; rG; rA; rA; rU; rC; rA; rA; rC; dU; dU-Sup | 3879 |
| HBG2-10 m13 | TGTATCCAGAGAATCAACA | rU; rG; rU; rA; rU; rC; rC; rA; rG; rA; rG; rA; rA; rU; rC; rA; rA; rC; rA; dU; dU-Sup | 3880 |
| HBG2-11 m13 | GTATCCAGAGAATCAACAT | rG; rU; rA; rU; rC; rC; rA; rG; rA; rG; rA; rA; rU; rC; rA; rA; rC; rA; rU; dU; dU-Sup | 3881 |
| HBG2-12 m13 | TATCCAGAGAATCAACATA | rU; rA; rU; rC; rC; rA; rG; rA; rG; rA; rA; rU; rC; rA; rA; rC; rA; rU; rA; dU; dU-Sup | 3882 |
| HBG2-13 m13 | ATCCAGAGAATCAACATAC | rA; rU; rC; rC; rA; rG; rA; rG; rA; rA; rU; rC; rA; rA; rC; rA; rU; rA; rC; dU; dU-Sup | 3883 |
| HBG2-14 m13 | TCCAGAGAATCAACATACA | rU; rC; rC; rA; rG; rA; rG; rA; rA; rU; rC; rA; rA; rC; rA; rU; rA; rC; rA; dU; dU-Sup | 3884 |
| HBG2-15 m13 | AGAGAATCAACATACAATG | rA; rG; rA; rG; rA; rA; rU; rC; rA; rA; rC; rA; rU; rA; rC; rA; rA; rU; rG; dU; dU-Sup | 3885 |
| HBG2-16 m13 | AGAATCAACATACAATGAG | rA; rG; rA; rA; rU; rC; rA; rA; rC; rA; rU; rA; rC; rA; rA; rU; rG; rA; rG; dU; dU-Sup | 3886 |
| HBG2-17 m13 | GAATCAACATACAATGAGC | rG; rA; rA; rU; rC; rA; rA; rC; rA; rU; rA; rC; rA; rA; rU; rG; rA; rG; rC; dU; dU-Sup | 3887 |
| HBG2-18 m13 | AATCAACATACAATGAGCA | rA; rA; rU; rC; rA; rA; rC; rA; rU; rA; rC; rA; rA; rU; rG; rA; rG; rC; rA; dU; dU-Sup | 3888 |
| HBG2-19 m13 | ATCAACATACAATGAGCAA | rA; rU; rC; rA; rA; rC; rA; rU; rA; rC; rA; rA; rU; rG; rA; rG; rC; rA; rA; dU; dU-Sup | 3889 |
| HBG2-20 m13 | TCAACATACAATGAGCAAA | rU; rC; rA; rA; rC; rA; rU; rA; rC; rA; rA; rU; rG; rA; rG; rC; rA; rA; rA; dU; dU-Sup | 3890 |
| HBG2-21 m13 | CAACATACAATGAGCAAAA | rC; rA; rA; rC; rA; rU; rA; rC; rA; rA; rU; rG; rA; rG; rC; rA; rA; rA; rA; dU; dU-Sup | 3891 |
| HBG2-22 m13 | AACATACAATGAGCAAAAG | rA; rA; rC; rA; rU; rA; rC; rA; rA; rU; rG; rA; rG; rC; rA; rA; rA; rA; rG; dU; dU-Sup | 3892 |
| HBG2-23 m13 | GGAAGCACCCTTCAGCAGT | rG; rG; rA; rA; rG; rC; rA; rC; rC; rC; rU; rU; rC; rA; rG; rC; rA; rG; rU; dU; dU-Sup | 3893 |
| HBG2-24 m13 | GAAGCACCCTTCAGCAGTT | rG; rA; rA; rG; rC; rA; rC; rC; rC; rU; rU; rC; rA; rG; rC; rA; rG; rU; rU; dU; dU-Sup | 3894 |
| HBG2-25 m13 | AGCACCCTTCAGCAGTTCC | rA; rG; rC; rA; rC; rC; rC; rU; rU; rC; rA; rG; rC; rA; rG; rU; rU; rC; rC; dU; dU-Sup | 3895 |

TABLE 3-continued

Formatted oligonucleotide sequences made for testing in the lab showing nucleotide modifications.

| OligoID | Base Sequence | Formatted Sequence | SeqID |
|---|---|---|---|
| HBG2-26 m13 | GCACCCTTCAGCAGT TCCA | rG; rC; rA; rC; rC; rC; rU; rU; rC; rA; rG; rC; rA; rG; rU; rU; rC; rC; rA; dU; dU-Sup | 3896 |
| HBG2-27 m13 | CACCCTTCAGCAGTT CCAC | rC; rA; rC; rC; rC; rU; rU; rC; rA; rG; rC; rA; rG; rU; rU; rC; rC; rA; rC; dU; dU-Sup | 3897 |
| HBG2-28 m13 | ACCCTTCAGCAGTTC CACA | rA; rC; rC; rC; rU; rU; rC; rA; rG; rC; rA; rG; rU; rU; rC; rC; rA; rC; rA; dU; dU-Sup | 3898 |
| HBG2-29 m13 | CCCTTCAGCAGTTCC ACAC | rC; rC; rC; rU; rU; rC; rA; rG; rC; rA; rG; rU; rU; rC; rC; rA; rC; rA; rC; dU; dU-Sup | 3899 |
| HBG2-30 m13 | CCTTCAGCAGTTCCA CACA | rC; rC; rU; rU; rC; rA; rG; rC; rA; rG; rU; rC; rC; rA; rC; rA; rC; rA; rC; dU; dU-Sup | 3900 |
| HBG2-31 m13 | CTTCAGCAGTTCCAC ACAC | rC; rU; rU; rC; rA; rG; rC; rA; rG; rU; rU; rC; rC; rA; rC; rA; rC; rA; rC; dU; dU-Sup | 3901 |
| HBG2-32 m13 | TTCAGCAGTTCCACA CACT | rU; rU; rC; rA; rG; rC; rA; rG; rU; rU; rC; rC; rA; rC; rA; rC; rA; rC; rU; dU; dU-Sup | 3902 |
| HBG2-33 m13 | CAGCAGTTCCACACA CTCG | rC; rA; rG; rC; rA; rG; rU; rU; rC; rC; rA; rC; rA; rC; rA; rC; rU; rC; rG; dU; dU-Sup | 3903 |
| HBG2-34 m13 | AGCAGTTCCACACAC TCGC | rA; rG; rC; rA; rG; rU; rU; rC; rC; rA; rC; rA; rC; rA; rC; rU; rC; rG; rC; dU; dU-Sup | 3904 |
| HBG2-35 m13 | GCAGTTCCACACACT CGCT | rG; rC; rA; rG; rU; rU; rC; rC; rA; rC; rA; rC; rA; rC; rU; rC; rG; rC; rU; dU; dU-Sup | 3905 |
| HBG2-36 m13 | CAGTTCCACACACTC GCTT | rC; rA; rG; rU; rU; rC; rC; rA; rC; rA; rC; rA; rC; rU; rC; rG; rC; rU; rU; dU; dU-Sup | 3906 |
| HBG2-37 m13 | AGTTCCACACACTCG CTTC | rA; rG; rU; rU; rC; rC; rA; rC; rA; rC; rA; rC; rU; rC; rG; rC; rU; rU; rC; dU; dU-Sup | 3907 |
| HBG2-38 m13 | GTTCCACACACTCGC TTCT | rG; rU; rU; rC; rC; rA; rC; rA; rC; rA; rC; rU; rC; rG; rC; rU; rU; rC; rU; dU; dU-Sup | 3908 |
| HBG2-39 m13 | TTCCACACACTCGCT TCTG | rU; rU; rC; rC; rA; rC; rA; rC; rA; rC; rU; rC; rG; rC; rU; rU; rC; rU; rG; dU; dU-Sup | 3909 |
| HBG2-40 m13 | TCCACACACTCGCTT CTGG | rU; rC; rC; rA; rC; rA; rC; rA; rC; rU; rC; rG; rC; rU; rU; rC; rU; rG; rG; dU; dU-Sup | 3910 |
| HBG2-41 m13 | CCACACACTCGCTTC TGGA | rC; rC; rA; rC; rA; rC; rA; rC; rU; rC; rG; rC; rU; rU; rC; rU; rG; rG; rA; dU; dU-Sup | 3911 |
| HBG2-42 m13 | ACACACTCGCTTCTG GAAC | rA; rC; rA; rC; rA; rC; rU; rC; rG; rC; rU; rU; rC; rU; rG; rG; rA; rA; rC; dU; dU-Sup | 3912 |
| HBG2-43 m13 | CACACTCGCTTCTGG AACG | rC; rA; rC; rA; rC; rU; rC; rG; rC; rU; rU; rC; rU; rG; rG; rA; rA; rC; rG; dU; dU-Sup | 3913 |
| HBG2-44 m13 | ACACTCGCTTCTGGA ACGT | rA; rC; rA; rC; rU; rC; rG; rC; rU; rU; rC; rU; rG; rG; rA; rA; rC; rG; rU; dU; dU-Sup | 3914 |

TABLE 3-continued

Formatted oligonucleotide sequences made for testing in the lab showing nucleotide modifications.

| OligoID | Base Sequence | Formatted Sequence | SeqID |
|---|---|---|---|
| HBG2-45 m13 | CACTCGCTTCTGGAA CGTC | rC; rA; rC; rU; rC; rG; rC; rU; rU; rC; rU; rG; rG; rA; rA; rC; rG; rU; rC; dU; dU-Sup | 3915 |
| HBG2-46 m13 | ACTCGCTTCTGGAAC GTCT | rA; rC; rU; rC; rG; rC; rU; rU; rC; rU; rG; rG; rA; rA; rC; rG; rU; rC; rU; dU; dU-Sup | 3916 |
| HBB-01_G7A dimer m1000 | GCTATTACCTTAACC CAGTTTTGCTATTAC CTTAACCCAG | InaGs; omeCs; InaTs; omeAs; InaTs; omeUs; InaAs; omeCs; InaCs; omeUs; InaTs; omeAs; InaAs; omeCs; InaCs; omeCs; InaAs; omeG; dT; dT; dT; dT; InaGs; omeCs; InaTs; omeAs; InaTs; omeUs; InaAs; omeCs; InaCs; omeUs; InaTs; omeAs; InaAs; omeCs; InaCs; omeCs; InaAs; omeG-Sup | 3795 |
| HBB-06 705 control dimer | CCTCTTACCTCAGTT ACATTTTCCTCTTAC CTCAGTTACA | InaCs; omeCs; InaTs; omeCs; InaTs; omeUs; InaAs; omeCs; InaCs; omeUs; InaCs; omeAs; InaGs; omeUs; InaTs; omeAs; InaCs; omeA; dT; dT; dT; dT; InaCs; omeCs; InaTs; omeCs; InaTs; omeUs; InaAs; omeCs; InaCs; omeUs; InaCs; omeAs; InaGs; omeUs; InaTs; omeAs; InaCs; omeA-Sup | 3796 |

BRIEF DESCRIPTION OF THE SEQUENCE LISTING

| SEQ ID | Chrom | Gene | Chr. Start | Chr. End | Strand |
|---|---|---|---|---|---|
| 1 | chr11 | HBB | 5234695 | 5260301 | − |
| 2 | chr11 | HBB | 5234695 | 5260301 | + |
| 3 | chr11 | HBD | 5242058 | 5267858 | − |
| 4 | chr11 | HBD | 5242058 | 5267858 | + |
| 5 | chr11 | HBE1 | 5277579 | 5303373 | − |
| 6 | chr11 | HBE1 | 5277579 | 5303373 | + |
| 7 | chr11 | HBG1 | 5257501 | 5283087 | − |
| 8 | chr11 | HBG1 | 5257501 | 5283087 | + |
| 9 | chr11 | HBG2 | 5262420 | 5288011 | − |
| 10 | chr11 | HBG2 | 5262420 | 5288011 | + |
| 11 | chr7 | Hbb-b1 | 110949041 | 110974437 | − |
| 12 | chr7 | Hbb-b1 | 110949041 | 110974437 | + |
| 13 | chr7 | Hbb-bh1 | 110978151 | 111003676 | − |
| 14 | chr7 | Hbb-bh1 | 110978151 | 111003676 | + |
| 15 | chr7 | Hbb-y | 110988267 | 111013721 | − |
| 16 | chr7 | Hbb-y | 110988267 | 111013721 | + |
| 17 | chr11 | HBB/HBD | 5246366 | 5246414 | + |
| 18 | chr11 | HBB/HBD | 5244366 | 5248414 | + |

Single Strand Oligonucleotides (Sense Strand of Target Gene)
SeqID range: 19-3788, 3820-3821, 3825-3826, 3850-3916
SeqIDs w/o G Runs:
19-50, 64-77, 112, 126-187, 201-253, 266-322, 327-358, 368-382, 401-445, 473-475, 489-808, 822-856, 870-955, 969-1021, 1035-1148, 1162-1232, 1246-1402, 1431-1508, 1530-1568, 1582-1956, 1971-2079, 2093-2481, 2495-2511, 2525-2580, 2594-3075, 3101-3114, 3128-3136, 3150-3309, 3323-3344, 3358-3399, 3414-3443, 3461-3467, 3481-3532, 3546-3788, 3820-3821, 3825-3826, 3850-3870, 3876-3916
SeqIDs w/o miR Seeds:
19, 22-26, 28-29, 31-32, 34-37, 39, 44, 46-47, 49, 51-52, 54, 56-60, 62, 64-65, 68-76, 78, 90, 99, 109, 111-113, 115, 119-120, 125, 128-136, 138-141, 143-149, 156, 160-162, 164-165, 172, 175-176, 178, 181-189, 194, 199, 204-206, 208-211, 215-216, 221-224, 227, 230-234, 237, 239, 242-243, 245, 247, 251-252, 254-258, 261, 263, 266, 270, 275-276, 279, 281-284, 286, 288-294, 296, 299, 301-303, 305, 308, 310-315, 318, 320, 326-332, 334, 336, 338-340, 342, 345-348, 352-353, 355-356, 358-361, 363-364, 366, 368-370, 372-373, 376-381, 383, 385-387, 389, 392, 394-395, 397, 400-408, 410-415, 419, 421, 424-428, 430-431, 434-438, 442-447, 449-451, 456, 458-463, 466-473, 475, 477-482, 485-486, 490-502, 504-505, 507, 516-517, 519-521, 523-524, 526-550, 552, 554-579, 581, 583-586, 588-599, 601, 604-610, 612-613, 615-619, 621-628, 632-635, 639, 641, 643, 646-649, 651-655, 658-662, 668-673, 675-679, 681-684, 686-691, 694-699, 701, 703, 705, 708-709, 711, 713-716, 718-722, 724, 726-727, 729-730, 733-736, 738, 741-746, 748, 750, 753, 755-759, 761, 764, 766, 768-801, 803, 805-806, 808-809, 812-816, 818, 820-824, 828, 830-831, 834-838, 841-844, 847, 850, 853-860, 864, 866-867, 869-870, 873-874, 876, 878-882, 884, 887-892, 895-898, 900-901, 903, 905-910, 913-916, 918-919, 921-928, 930-935, 937-938, 941-943, 947-951, 956-961, 963, 967-977, 979-986, 988-989, 991, 995-996, 998, 1001, 1003-1005, 1009, 1012-1016, 1018, 1023-1024, 1026-1029, 1031, 1033-1035, 1037, 1039-1044, 1047, 1049-1051, 1054-1055, 1058-1059, 1062-1069, 1071, 1074-1075, 1078-1088, 1090, 1093-1097, 1100-1103, 1106, 1108-1109, 1111-1112, 1114-1115, 1120, 1123-1126, 1131-1134, 1136-1137, 1141-1142, 1144-1152, 1155, 1160-1165, 1170-1172, 1174-1175, 1181-1189, 1195-1200, 1202-1205, 1207-1210, 1212, 1214, 1217, 1219-1223, 1225-1226, 1229, 1232-1237, 1243-1244, 1247-1252, 1255, 1257-1259, 1261, 1263-1264, 1270-1272, 1274-1276, 1278, 1280, 1282-1283, 1286-1287, 1289-1293, 1296, 1298, 1304-1306, 1308, 1311-

1314, 1316, 1318-1319, 1322, 1330-1332, 1334, 1336-1339, 1341-1345, 1347-1349, 1353-1354, 1356-1359, 1361-1369, 1371-1372, 1374-1376, 1378-1380, 1382-1383, 1385-1386, 1388, 1391-1401, 1403-1408, 1411, 1416, 1421-1424, 1427, 1430, 1432-1439, 1443, 1445, 1449-1455, 1457-1458, 1460-1461, 1463, 1465-1469, 1471-1473, 1476, 1478-1480, 1482, 1484-1492, 1495-1498, 1500, 1503-1507, 1509-1517, 1522-1523, 1530-1532, 1537, 1539, 1541-1546, 1548-1549, 1551, 1553, 1555, 1557-1558, 1560-1562, 1564-1567, 1569, 1573-1574, 1579, 1582-1587, 1589, 1591-1594, 1596, 1598-1601, 1605-1607, 1609, 1611, 1615, 1618, 1622, 1625-1629, 1631-1633, 1637, 1639-1642, 1644, 1646, 1648-1649, 1655, 1657-1658, 1661-1663, 1666-1671, 1673-1675, 1677-1679, 1681-1686, 1690, 1699, 1701-1707, 1709-1710, 1715-1718, 1720-1721, 1723-1726, 1728-1729, 1731, 1734-1737, 1739-1741, 1743-1749, 1751-1759, 1761, 1764, 1766, 1768-1772, 1775-1777, 1780-1781, 1783-1784, 1787-1800, 1802-1804, 1806-1809, 1811, 1814-1818, 1820, 1822-1823, 1826, 1832-1838, 1840-1851, 1855, 1859, 1865, 1867-1868, 1870, 1874, 1876-1877, 1879-1882, 1884-1886, 1888-1889, 1892-1894, 1897-1901, 1907, 1909-1910, 1912, 1914, 1916-1924, 1927-1928, 1930-1932, 1935-1938, 1941-1943, 1946, 1948-1949, 1951, 1954, 1957, 1960, 1962-1967, 1969-1973, 1977-1979, 1981-1983, 1985-1986, 1989-1991, 1995, 1999-2000, 2003, 2005-2010, 2014-2015, 2020, 2022-2025, 2027-2028, 2030-2032, 2034, 2036, 2040, 2042, 2045-2046, 2048-2058, 2060, 2062, 2064-2065, 2067, 2070, 2072, 2075-2077, 2079-2080, 2084, 2087-2088, 2092-2102, 2105-2106, 2113, 2120-2125, 2130, 2132-2133, 2136, 2138-2139, 2141-2142, 2145-2148, 2151-2154, 2156-2157, 2159, 2163-2165, 2167-2169, 2173-2175, 2177, 2182, 2184-2187, 2189, 2192, 2195-2197, 2200-2204, 2206-2207, 2209-2210, 2212-2213, 2216, 2218-2220, 2222-2226, 2228, 2230-2231, 2233-2234, 2238-2241, 2245, 2247-2249, 2254, 2257-2259, 2262-2264, 2266, 2268-2272, 2274-2277, 2279-2280, 2286-2287, 2289, 2292-2293, 2295-2296, 2299-2302, 2304-2309, 2312-2315, 2317-2334, 2336-2345, 2347-2350, 2352-2355, 2358-2359, 2364-2366, 2369-2370, 2372-2373, 2375, 2380, 2382, 2384-2386, 2388-2390, 2393-2394, 2396, 2399, 2401-2404, 2406, 2411, 2413-2415, 2418-2420, 2422-2423, 2425, 2430, 2432-2438, 2440, 2442, 2445-2448, 2451, 2454, 2456-2457, 2461-2464, 2467-2468, 2473-2479, 2481-2482, 2484-2488, 2491-2492, 2494-2500, 2504-2505, 2507-2510, 2512, 2514-2516, 2518-2528, 2530-2532, 2534, 2538-2539, 2541, 2543-2544, 2546, 2550-2552, 2554, 2556, 2558, 2561, 2563-2572, 2574, 2577, 2579-2581, 2583-2587, 2590, 2592-2596, 2599-2605, 2607-2608, 2611-2613, 2615-2616, 2619-2622, 2624, 2629-2634, 2636, 2638, 2640-2644, 2646, 2649-2651, 2655, 2657-2658, 2660, 2662-2668, 2670, 2672-2679, 2681-2683, 2685-2690, 2692-2693, 2697-2699, 2701-2702, 2705, 2707, 2710-2714, 2717, 2719, 2721, 2723, 2725-2726, 2728, 2731, 2733-2734, 2736-2737, 2739-2740, 2742-2743, 2745-2748, 2752-2754, 2756-2758, 2761, 2763, 2765-2766, 2768, 2770-2778, 2780, 2783-2784, 2789-2798, 2800, 2805-2806, 2808-2810, 2812, 2814, 2817-2828, 2830-2838, 2840-2841, 2843, 2845-2850, 2852-2853, 2856, 2858-2859, 2861-2862, 2864-2867, 2870, 2872-2874, 2876-2881, 2883-2885, 2887, 2889, 2892-2896, 2898, 2900-2902, 2905-2906, 2908, 2910-2912, 2915-2921, 2923, 2926-2928, 2932-2933, 2937-2938, 2940-2943, 2945-2946, 2948-2949, 2951-2958, 2962, 2970-2972, 2974, 2976-2977, 2979-2981, 2983, 2985-2988, 2990-2991, 2993, 2997, 2999-3000, 3003-3007, 3009-3012, 3016, 3018, 3021-3022, 3024-3025, 3027-3029, 3032-3033, 3035, 3037-3038, 3040-3042, 3046, 3048, 3050-3054, 3060-3062, 3071, 3074-3075, 3079-3081, 3083, 3085-3086, 3088, 3093, 3099, 3101-3102, 3105-3106, 3111-3114, 3116-3118, 3121-3125, 3127-3128, 3131, 3134, 3137-3138, 3141-3143, 3150-3151, 3153-3156, 3159-3160, 3162-3164, 3166-3173, 3175-3176, 3179-3184, 3187, 3190, 3192-3193, 3195-3201, 3205-3217, 3220-3221, 3223, 3225-3226, 3228-3229, 3231-3232, 3236-3250, 3252-3253, 3258-3259, 3261-3263, 3265-3271, 3273, 3275, 3281-3282, 3285, 3288, 3290-3296, 3298, 3301, 3304-3305, 3308-3310, 3312, 3314, 3319, 3322-3323, 3325-3327, 3329, 3331, 3333, 3335-3337, 3339-3344, 3346-3352, 3356-3358, 3360, 3364, 3366-3369, 3371-3381, 3384-3385, 3389-3391, 3393-3401, 3404-3406, 3408-3410, 3413-3415, 3421-3423, 3426-3428, 3431, 3433, 3437-3440, 3443-3448, 3450-3453, 3459-3461, 3463, 3466-3471, 3473-3475, 3477-3478, 3480, 3484-3488, 3490-3491, 3494-3496, 3498, 3500-3502, 3504, 3506, 3509-3511, 3513, 3515-3521, 3524-3531, 3533-3536, 3538-3540, 3542, 3545, 3547-3548, 3551-3555, 3558-3561, 3563-3565, 3567-3571, 3574, 3577, 3584-3585, 3587-3588, 3590, 3592, 3595-3600, 3602, 3604-3605, 3607, 3609, 3611-3616, 3618-3620, 3623-3624, 3627-3629, 3631-3637, 3642-3647, 3650-3655, 3657, 3660-3662, 3666-3668, 3670-3671, 3673-3676, 3679-3684, 3687-3688, 3691-3693, 3695-3700, 3703, 3705-3708, 3710, 3712, 3714-3716, 3719, 3722-3725, 3727-3729, 3731-3737, 3741, 3743-3745, 3748-3753, 3758-3760, 3763-3775, 3777, 3779-3785, 3787-3788, 3820-3821, 3825, 3850-3854, 3856-3859, 3861-3867, 3870-3874, 3876-3879, 3881, 3884-3885, 3887-3888, 3890, 3892-3895, 3897-3898, 3900-3901, 3904, 3906-3907, 3909-3916

Single Strand Oligonucleotides (Antisense Strand of Target Gene)
SeqID range: 3797-3819, 3822-3824, 3827-3849
SeqIDs w/o G Runs:
3797-3819, 3822-3824, 3827-3849
SeqIDs w/o miR Seeds:
3797-3798, 3800-3804, 3806-3808, 3811-3817, 3822-3824, 3827, 3829-3834, 3836-3838, 3843, 3845-3847

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10174315B2). An electronic copy of the "Sequence Listing" will also be available from the USPTO upon request and payment of the fee set forth in 37 CFR 1.19(b)(3).

What is claimed is:

1. A single stranded oligonucleotide produced by a process comprising:
synthesizing a single stranded oligonucleotide that:
(a) has a sequence 5'-X-Y-Z, wherein X is any nucleotide, Y is a nucleotide sequence of 6 nucleotides in length that is not a seed sequence of a human microRNA, and Z is a nucleotide sequence of 4-9 nucleotides in length,
(b) is complementary with at least 8 consecutive nucleotides of a PRC2-associated region of a human hemoglobin gene, wherein the PRC2-associated region is a region of the hemoglobin gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the hemoglobin gene compared to a control sequencing reaction of products of a control RNA-immunoprecipitation assay that employs a control antibody; and
(c) is 11 to 16 nucleotides in length, wherein, during the synthesis, at least one nucleotide incorporated into the oligonucleotide is a nucleotide analogue.

2. The single stranded oligonucleotide of claim 1, wherein the oligonucleotide does not comprise three or more consecutive guanosine nucleotides.

3. The single stranded oligonucleotide of claim 1, wherein the oligonucleotide does not comprise four or more consecutive guanosine nucleotides.

4. The single stranded oligonucleotide of claim 1, wherein the at least one nucleotide analogue results in an increase in Tm of the oligonucleotide in a range of 1 to 5 ° C. compared with an oligonucleotide that does not have the at least one nucleotide analogue.

5. The single stranded oligonucleotide of claim 1, wherein at least one nucleotide of the oligonucleotide comprises a 2' O-methyl.

6. The single stranded oligonucleotide of claim 1, wherein each nucleotide of the oligonucleotide comprises a 2' O-methyl.

7. The single stranded oligonucleotide of claim 1, wherein the oligonucleotide comprises at least one ribonucleotide, at least one deoxyribonucleotide, or at least one bridged nucleotide.

8. The single strand oligonucleotide of claim 7, wherein the bridged nucleotide is a LNA nucleotide, a cEt nucleotide or a ENA modified nucleotide.

9. The single stranded oligonucleotide of claim 1, wherein each nucleotide of the oligonucleotide is a LNA nucleotide.

10. The single stranded oligonucleotide of claim 1, wherein the nucleotides of the oligonucleotide comprise alternating deoxyribonucleotides and 2'-fluoro-deoxyribonucleotides.

11. The single stranded oligonucleotide of claim 1, wherein the nucleotides of the oligonucleotide comprise alternating deoxyribonucleotides and 2'-O-methyl nucleotides.

12. The single stranded oligonucleotide of claim 1, wherein the nucleotides of the oligonucleotide comprise alternating deoxyribonucleotides and ENA nucleotide analogues.

13. The single stranded oligonucleotide of claim 1, wherein the nucleotides of the oligonucleotide comprise alternating deoxyribonucleotides and LNA nucleotides.

14. The single stranded oligonucleotide of claim 10, wherein the 5' nucleotide of the oligonucleotide is a deoxyribonucleotide.

15. The single stranded oligonucleotide of claim 1, wherein the nucleotides of the oligonucleotide comprise alternating LNA nucleotides and 2'-O-methyl nucleotides.

16. The single stranded oligonucleotide of claim 15, wherein the 5' nucleotide of the oligonucleotide is a LNA nucleotide.

17. The single stranded oligonucleotide of claim 1, wherein the nucleotides of the oligonucleotide comprise deoxyribonucleotides flanked by at least one LNA nucleotide on each of the 5' and 3' ends of the deoxyribonucleotides.

18. The single stranded oligonucleotide of claim 1, further comprising phosphorothioate internucleotide linkages between at least two nucleotides.

19. The single stranded oligonucleotide of claim 18, further comprising phosphorothioate internucleotide linkages between all nucleotides.

20. The single stranded oligonucleotide of claim 1, wherein the nucleotide at the 3' position of the oligonucleotide has a 3' hydroxyl group.

21. The single stranded oligonucleotide of claim 1, wherein the nucleotide at the 3' position of the oligonucleotide has a 3' thiophosphate.

22. The single stranded oligonucleotide of claim 1, further comprising a biotin moiety conjugated to the 5' nucleotide.

23. A single stranded oligonucleotide produced by a process comprising:
synthesizing a single stranded oligonucleotide that:
(a) comprises a region of complementarity that is complementary with at least 8 consecutive nucleotides of a PRC2-associated region of a human hemoglobin gene, wherein the PRC2-associated region is a region of the hemoglobin gene that has a sequence that occurs at a higher frequency in a sequencing reaction of products of an RNA-immunoprecipitation assay that employs an antibody that targets Ezh2 to immunoprecipitate RNA-associated PRC2 complexes from cells comprising the hemoglobin gene compared to a control sequencing reaction of products of a control RNA-immunoprecipitation assay that employs a control antibody;

(b) is between 11 and 16 nucleotides in length and has at least one of:
  i) a sequence that is 5'X-Y-Z, wherein X is any nucleotide and wherein X is anchored at the 5' end of the oligonucleotide, Y is a nucleotide sequence of 6 nucleotides in length that is not a human seed sequence of a microRNA, and Z is a nucleotide sequence of 4 to 9 nucleotides in length;
  ii) a sequence that does not comprise three or more consecutive guanosine nucleotides;
  iii) a sequence that is complementary to a PRC2-associated region that encodes an RNA that forms a secondary structure comprising at least two single stranded loops; and/or
  iv) a sequence that has greater than 60% G-C content;
wherein, during the synthesis, at least one nucleotide incorporated into the oligonucleotide is a nucleotide analogue.

24. The single stranded oligonucleotide of claim 23, wherein the oligonucleotide has the sequence 5'X-Y-Z.

25. A composition comprising a single stranded oligonucleotide of claim 1 and a carrier.

26. A composition comprising a single stranded oligonucleotide of claim 1 in a buffered solution.

27. A composition of claim 26, wherein the oligonucleotide is conjugated to the carrier.

28. The composition of claim 27, wherein the carrier is a peptide.

29. The composition of claim 27, wherein the carrier is a steroid.

30. A pharmaceutical composition comprising a composition of claim 25 and a pharmaceutically acceptable carrier.

31. A kit comprising a container housing the composition of claim 25.

* * * * *